US008889130B2

(12) United States Patent
Kamath

(10) Patent No.: US 8,889,130 B2
(45) Date of Patent: Nov. 18, 2014

(54) TREATMENT OF OSTEOARTHRITIS AND PAIN

(75) Inventor: Rajesh V. Kamath, Shrewsbury, MA (US)

(73) Assignee: Abbvie Inc., North Chicago, IL (US)

(*) Notice: Subject to any disclaimer, the term of this patent is extended or adjusted under 35 U.S.C. 154(b) by 0 days.

(21) Appl. No.: 13/369,177

(22) Filed: Feb. 8, 2012

(65) Prior Publication Data

US 2012/0201781 A1 Aug. 9, 2012

Related U.S. Application Data

(60) Provisional application No. 61/440,853, filed on Feb. 8, 2011.

(51) Int. Cl.
| | | |
|---|---|---|
| *A61K 39/395* | (2006.01) | |
| *A61K 39/40* | (2006.01) | |
| *C07K 16/24* | (2006.01) | |
| *C07K 16/00* | (2006.01) | |
| *A61K 39/00* | (2006.01) | |

(52) U.S. Cl.
CPC ........... *C07K 16/244* (2013.01); *C07K 2317/51* (2013.01); *C07K 2317/24* (2013.01); *C07K 2317/31* (2013.01); *A61K 2039/507* (2013.01); *C07K 2317/76* (2013.01); *C07K 2317/94* (2013.01); *C07K 2317/515* (2013.01); *C07K 2317/92* (2013.01); *A61K 2039/505* (2013.01)
USPC ................... 424/130.1; 424/132.1; 424/133.1; 424/136.1; 424/141.1; 424/142.1; 424/145.1

(58) Field of Classification Search
None
See application file for complete search history.

(56) References Cited

U.S. PATENT DOCUMENTS

| | | | |
|---|---|---|---|
| 7,491,516 B2 | 2/2009 | Collinson et al. | |
| 7,612,181 B2 * | 11/2009 | Wu et al. ...................... | 530/387.3 |
| 8,258,268 B2 | 9/2012 | Wu et al. | |
| 8,324,350 B2 | 12/2012 | Hsieh et al. | |
| 8,383,778 B2 | 2/2013 | Hsieh et al. | |
| 8,398,966 B2 | 3/2013 | Wu et al. | |
| 8,475,766 B2 | 7/2013 | Collinson et al. | |
| 2008/0292640 A1 | 11/2008 | Solinger et al. | |
| 2009/0060923 A1 | 3/2009 | Masat et al. | |
| 2009/0215992 A1 | 8/2009 | Wu et al. | |
| 2009/0226461 A1 | 9/2009 | Masat et al. | |
| 2010/0303807 A1 | 12/2010 | Solinger et al. | |
| 2011/0008766 A1 | 1/2011 | Ghayur et al. | |
| 2011/0165063 A1 | 7/2011 | Hsieh et al. | |
| 2011/0280800 A1 | 11/2011 | Wu et al. | |
| 2012/0275996 A1 | 11/2012 | Hsieh et al. | |
| 2013/0195754 A1 | 8/2013 | Wu et al. | |

FOREIGN PATENT DOCUMENTS

WO  WO2012/09373 A2  8/2012

OTHER PUBLICATIONS

Jotanovic et al. Drugs Aging 2012;29;5:343-358.*
Wu et al. Nature biotechnology 2007 25;1:1290-1297.*
Pelletier et al. Arthritis Research & Therapy, 2006, 8;2:1-14.*
International Search Report and Written Opinion, PCT/US2012/024356, dated Aug. 23, 2012, 10 pages.
International Preliminary Report on Patentability, PCT/US2012/024356, dated Mar. 6, 2013, 5 pages.
Chevalier: Upregulation of enzymatic activity by interleukin-1 in osteoarthritis; Biomed Pharmacother; 1997, vol. 51, No. 2, pp. 58-62.
Chevalier et al: Desperately looking for the right target in osteoarthritis: the anti-IL-1 strategy; Arthritis Res Ther; 2011, vol. 13, No. 4, pp. 124-125.
Joosten et al: IL-1 alpha/beta blockade prevents cartilage and bone destruction in murine type II collagen-induced arthritis, whereas TNF-alpha blockade only ameliorates joint inflammation; J Immunol; 1999, vol. 163, No. 9, pp. 5049-5055.
Joosten et al: Anticytokine treatment of established type II collagen-induced arthritis in DBA/1 mice; A comparative study using anti-TNF alpha, anti-IL-1 alpha/beta, and IL-1Ra; Arthritis Rheum; 1996, vol. 39, No. 5, pp. 797-809.
Malemud: Anticytokine Therapy for Osteoarthritis, Evidence to Date; Drugs Aging; 2010, vol. 27, No. 2, pp. 95-115.
Niger et al: Interleukin-1beta Increases Gap Junctional Communication among Synovial Fibroblasts via the Extracellular Signal Regulated Kinase Pathway; Biol Cell; 2009, vol. 102, No. 1, pp. 37-49.

* cited by examiner

*Primary Examiner* — Chun Dahle
(74) *Attorney, Agent, or Firm* — Lathrop & Gage LLP; James H. Velema, Esq.; Peter Dini

(57) ABSTRACT

The present invention relates to the treatment of osteoarthritis and pain using IL-1α and IL-1β binding proteins, including anti-IL-1α and anti-IL-1β antibodies and engineered multivalent and multispecific IL-1α and IL-1β binding proteins.

14 Claims, 13 Drawing Sheets

SEQUENCE LISTING

```
<160> NUMBER OF SEQ ID NOS: 151

<210> SEQ ID NO 1
<211> LENGTH: 271
<212> TYPE: PRT
<213> ORGANISM: Homo sapiens

<400> SEQUENCE: 1

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205
```

```
Glu Ile Pro Lys Thr Ile Thr Gly Ser Glu Thr Asn Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 2
<211> LENGTH: 153
<212> TYPE: PRT
<213> ORGANISM: Homo sapiens

<400> SEQUENCE: 2

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
```

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 106
<212> TYPE: PRT
<213> ORGANISM: Homo sapiens

<400> SEQUENCE: 5

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 6
<211> LENGTH: 105
<212> TYPE: PRT
<213> ORGANISM: Homo sapiens

<400> SEQUENCE: 6

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
```

```
                35                  40                  45
Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 7
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa can be any amino acid

<400> SEQUENCE: 7

Phe Gly Xaa Gly
 1

<210> SEQ ID NO 8
<211> LENGTH: 5
<212> TYPE: PRT
<213> ORGANISM: Homo sapiens

<400> SEQUENCE: 8

Leu Glu Trp Ile Gly
 1               5

<210> SEQ ID NO 9
<211> LENGTH: 4
<212> TYPE: PRT
<213> ORGANISM: Homo sapiens

<400> SEQUENCE: 9

Trp Gly Trp Gly
 1

<210> SEQ ID NO 10
<211> LENGTH: 30
<212> TYPE: PRT
<213> ORGANISM: Homo sapiens

<400> SEQUENCE: 10

Glu Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser
             20                  25                  30

<210> SEQ ID NO 11
<211> LENGTH: 14
<212> TYPE: PRT
<213> ORGANISM: Homo sapiens

<400> SEQUENCE: 11

Trp Ile Arg Gln Pro Pro Gly Lys Ala Leu Glu Trp Leu Ala
 1               5                  10

<210> SEQ ID NO 12
<211> LENGTH: 32
```

<212> TYPE: PRT
<213> ORGANISM: Homo sapiens

<400> SEQUENCE: 12

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 13
<211> LENGTH: 11
<212> TYPE: PRT
<213> ORGANISM: Homo sapiens

<400> SEQUENCE: 13

Trp Gly Gln Gly Thr Thr Val Thr Val Ser Ser
1               5                   10

<210> SEQ ID NO 14
<211> LENGTH: 30
<212> TYPE: PRT
<213> ORGANISM: Homo sapiens

<400> SEQUENCE: 14

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 15
<211> LENGTH: 14
<212> TYPE: PRT
<213> ORGANISM: Homo sapiens

<400> SEQUENCE: 15

Trp Ile Arg Gln Pro Pro Gly Lys Ala Leu Glu Trp Leu Ala
1               5                   10

<210> SEQ ID NO 16
<211> LENGTH: 32
<212> TYPE: PRT
<213> ORGANISM: Homo sapiens

<400> SEQUENCE: 16

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 17
<211> LENGTH: 11
<212> TYPE: PRT
<213> ORGANISM: Homo sapiens

<400> SEQUENCE: 17

Trp Gly Gln Gly Thr Thr Val Thr Val Ser Ser
1               5                   10

<210> SEQ ID NO 18
<211> LENGTH: 30
<212> TYPE: PRT
<213> ORGANISM: Homo sapiens

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 19
<211> LENGTH: 14
<212> TYPE: PRT
<213> ORGANISM: Homo sapiens

<400> SEQUENCE: 19

Trp Val Arg Gln Ala Pro Gly Lys Gly Leu Glu Trp Val Gly
1               5                   10

<210> SEQ ID NO 20
<211> LENGTH: 32
<212> TYPE: PRT
<213> ORGANISM: Homo sapiens

<400> SEQUENCE: 20

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 21
<211> LENGTH: 11
<212> TYPE: PRT
<213> ORGANISM: Homo sapiens

<400> SEQUENCE: 21

Trp Gly Gln Gly Thr Thr Val Thr Val Ser Ser
1               5                   10

<210> SEQ ID NO 22
<211> LENGTH: 30
<212> TYPE: PRT
<213> ORGANISM: Homo sapiens

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 23
<211> LENGTH: 14
<212> TYPE: PRT
<213> ORGANISM: Homo sapiens

<400> SEQUENCE: 23

Trp Val Arg Gln Ala Pro Gly Lys Gly Leu Glu Trp Val Ser
1               5                   10

<210> SEQ ID NO 24
<211> LENGTH: 32
<212> TYPE: PRT
<213> ORGANISM: Homo sapiens

<400> SEQUENCE: 24

Arg Phe Thr Ile Ser Arg Asp Asn Ala Lys Asn Ser Leu Tyr Leu Gln
1               5                   10                  15
```

Met Asn Ser Leu Arg Ala Glu Asp Thr Ala Val Tyr Tyr Cys Ala Arg
            20                  25                  30

<210> SEQ ID NO 25
<211> LENGTH: 11
<212> TYPE: PRT
<213> ORGANISM: Homo sapiens

<400> SEQUENCE: 25

Trp Gly Gln Gly Thr Thr Val Thr Val Ser Ser
1               5                   10

<210> SEQ ID NO 26
<211> LENGTH: 30
<212> TYPE: PRT
<213> ORGANISM: Homo sapiens

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 27
<211> LENGTH: 14
<212> TYPE: PRT
<213> ORGANISM: Homo sapiens

<400> SEQUENCE: 27

Trp Val Arg Gln Ala Pro Gly Gln Gly Leu Glu Trp Met Gly
1               5                   10

<210> SEQ ID NO 28
<211> LENGTH: 32
<212> TYPE: PRT
<213> ORGANISM: Homo sapiens

<400> SEQUENCE: 28

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 29
<211> LENGTH: 11
<212> TYPE: PRT
<213> ORGANISM: Homo sapiens

<400> SEQUENCE: 29

Trp Gly Gln Gly Thr Thr Val Thr Val Ser Ser
1               5                   10

<210> SEQ ID NO 30
<211> LENGTH: 30
<212> TYPE: PRT
<213> ORGANISM: Homo sapiens

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

```
<210> SEQ ID NO 31
<211> LENGTH: 14
<212> TYPE: PRT
<213> ORGANISM: Homo sapiens

<400> SEQUENCE: 31

Trp Val Arg Gln Ala Pro Gly Gln Gly Leu Glu Trp Met Gly
1               5                   10

<210> SEQ ID NO 32
<211> LENGTH: 32
<212> TYPE: PRT
<213> ORGANISM: Homo sapiens

<400> SEQUENCE: 32

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 33
<211> LENGTH: 11
<212> TYPE: PRT
<213> ORGANISM: Homo sapiens

<400> SEQUENCE: 33

Trp Gly Gln Gly Thr Thr Val Thr Val Ser Ser
1               5                   10

<210> SEQ ID NO 34
<211> LENGTH: 30
<212> TYPE: PRT
<213> ORGANISM: Homo sapiens

<400> SEQUENCE: 34

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 35
<211> LENGTH: 14
<212> TYPE: PRT
<213> ORGANISM: Homo sapiens

<400> SEQUENCE: 35

Trp Val Arg Gln Ala Pro Gly Gln Gly Leu Glu Trp Met Gly
1               5                   10

<210> SEQ ID NO 36
<211> LENGTH: 32
<212> TYPE: PRT
<213> ORGANISM: Homo sapiens

<400> SEQUENCE: 36

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 37
<211> LENGTH: 11
<212> TYPE: PRT
<213> ORGANISM: Homo sapiens
```

<400> SEQUENCE: 37

Trp Gly Gln Gly Thr Thr Val Thr Val Ser Ser
1               5                   10

<210> SEQ ID NO 38
<211> LENGTH: 23
<212> TYPE: PRT
<213> ORGANISM: Homo sapiens

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 39
<211> LENGTH: 15
<212> TYPE: PRT
<213> ORGANISM: Homo sapiens

<400> SEQUENCE: 39

Trp Tyr Gln Gln Lys Pro Gly Gln Pro Pro Lys Leu Leu Ile Tyr
1               5                   10                  15

<210> SEQ ID NO 40
<211> LENGTH: 32
<212> TYPE: PRT
<213> ORGANISM: Homo sapiens

<400> SEQUENCE: 40

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 41
<211> LENGTH: 11
<212> TYPE: PRT
<213> ORGANISM: Homo sapiens

<400> SEQUENCE: 41

Phe Gly Gly Gly Thr Lys Val Glu Ile Lys Arg
1               5                   10

<210> SEQ ID NO 42
<211> LENGTH: 23
<212> TYPE: PRT
<213> ORGANISM: Homo sapiens

<400> SEQUENCE: 42

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 43
<211> LENGTH: 15
<212> TYPE: PRT
<213> ORGANISM: Homo sapiens

<400> SEQUENCE: 43

Trp Tyr Gln Gln Lys Pro Gly Gln Ala Pro Arg Leu Leu Ile Tyr

<210> SEQ ID NO 44
<211> LENGTH: 32
<212> TYPE: PRT
<213> ORGANISM: Homo sapiens

<400> SEQUENCE: 44

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 45
<211> LENGTH: 11
<212> TYPE: PRT
<213> ORGANISM: Homo sapiens

<400> SEQUENCE: 45

Phe Gly Gly Gly Thr Lys Val Glu Ile Lys Arg
1               5                   10

<210> SEQ ID NO 46
<211> LENGTH: 23
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 47
<211> LENGTH: 15
<212> TYPE: PRT
<213> ORGANISM: Homo sapiens

<400> SEQUENCE: 47

Trp Tyr Gln Gln Lys Pro Glu Lys Ala Pro Lys Ser Leu Ile Tyr
1               5                   10                  15

<210> SEQ ID NO 48
<211> LENGTH: 32
<212> TYPE: PRT
<213> ORGANISM: Homo sapiens

<400> SEQUENCE: 48

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 49
<211> LENGTH: 11
<212> TYPE: PRT
<213> ORGANISM: Homo sapiens

<400> SEQUENCE: 49

Phe Gly Gly Gly Thr Lys Val Glu Ile Lys Arg
1               5                   10

<210> SEQ ID NO 50

```
<211> LENGTH: 23
<212> TYPE: PRT
<213> ORGANISM: Homo sapiens

<400> SEQUENCE: 50

Asp Ile Gln Met Thr Gln Ser Pro Ser Val Ser Ala Ser Val Gly
1               5                   10                  15

Asp Arg Val Thr Ile Thr Cys
            20

<210> SEQ ID NO 51
<211> LENGTH: 15
<212> TYPE: PRT
<213> ORGANISM: Homo sapiens

<400> SEQUENCE: 51

Trp Tyr Gln Gln Lys Pro Gly Lys Ala Pro Lys Leu Leu Ile Tyr
1               5                   10                  15

<210> SEQ ID NO 52
<211> LENGTH: 32
<212> TYPE: PRT
<213> ORGANISM: Homo sapiens

<400> SEQUENCE: 52

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 53
<211> LENGTH: 11
<212> TYPE: PRT
<213> ORGANISM: Homo sapiens

<400> SEQUENCE: 53

Phe Gly Gly Gly Thr Lys Val Glu Ile Lys Arg
1               5                   10

<210> SEQ ID NO 54
<211> LENGTH: 23
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 55
<211> LENGTH: 15
<212> TYPE: PRT
<213> ORGANISM: Homo sapiens

<400> SEQUENCE: 55

Trp Tyr Gln Gln Lys Pro Gly Lys Ala Pro Lys Leu Leu Ile Tyr
1               5                   10                  15

<210> SEQ ID NO 56
<211> LENGTH: 32
<212> TYPE: PRT
<213> ORGANISM: Homo sapiens
```

```
<400> SEQUENCE: 56

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 57
<211> LENGTH: 11
<212> TYPE: PRT
<213> ORGANISM: Homo sapiens

<400> SEQUENCE: 57

Phe Gly Gln Gly Thr Lys Leu Glu Ile Lys Arg
1               5                   10

<210> SEQ ID NO 58
<211> LENGTH: 11
<212> TYPE: PRT
<213> ORGANISM: Homo sapiens

<400> SEQUENCE: 58

Phe Gly Gly Gly Thr Lys Val Glu Ile Lys Arg
1               5                   10

<210> SEQ ID NO 59
<211> LENGTH: 16
<212> TYPE: PRT
<213> ORGANISM: Artificial Sequence
<220> FEATURE:
<223> OTHER INFORMATION: peptide linker sequence

<400> SEQUENCE: 59

Ala Lys Thr Thr Pro Lys Leu Glu Glu Gly Glu Phe Ser Glu Ala Arg
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: peptide linker sequence

<400> SEQUENCE: 60

Ala Lys Thr Thr Pro Lys Leu Glu Glu Gly Glu Phe Ser Glu Ala Arg
1               5                   10                  15

Val

<210> SEQ ID NO 61
<211> LENGTH: 9
<212> TYPE: PRT
<213> ORGANISM: Artificial Sequence
<220> FEATURE:
<223> OTHER INFORMATION: peptide linker sequence

<400> SEQUENCE: 61

Ala Lys Thr Thr Pro Lys Leu Gly Gly
1               5

<210> SEQ ID NO 62
<211> LENGTH: 10
<212> TYPE: PRT
<213> ORGANISM: Artificial Sequence
<220> FEATURE:
<223> OTHER INFORMATION: peptide linker sequence
```

```
<400> SEQUENCE: 62

Ser Ala Lys Thr Thr Pro Lys Leu Gly Gly
1               5                   10

<210> SEQ ID NO 63
<211> LENGTH: 6
<212> TYPE: PRT
<213> ORGANISM: Artificial Sequence
<220> FEATURE:
<223> OTHER INFORMATION: peptide linker sequence

<400> SEQUENCE: 63

Ser Ala Lys Thr Thr Pro
1               5

<210> SEQ ID NO 64
<211> LENGTH: 6
<212> TYPE: PRT
<213> ORGANISM: Artificial Sequence
<220> FEATURE:
<223> OTHER INFORMATION: peptide linker sequence

<400> SEQUENCE: 64

Arg Ala Asp Ala Ala Pro
1               5

<210> SEQ ID NO 65
<211> LENGTH: 9
<212> TYPE: PRT
<213> ORGANISM: Artificial Sequence
<220> FEATURE:
<223> OTHER INFORMATION: peptide linker sequence

<400> SEQUENCE: 65

Arg Ala Asp Ala Ala Pro Thr Val Ser
1               5

<210> SEQ ID NO 66
<211> LENGTH: 12
<212> TYPE: PRT
<213> ORGANISM: Artificial Sequence
<220> FEATURE:
<223> OTHER INFORMATION: peptide linker sequence

<400> SEQUENCE: 66

Arg Ala Asp Ala Ala Ala Ala Gly Gly Pro Gly Ser
1               5                   10

<210> SEQ ID NO 67
<211> LENGTH: 27
<212> TYPE: PRT
<213> ORGANISM: Artificial Sequence
<220> FEATURE:
<223> OTHER INFORMATION: peptide linker sequence

<400> SEQUENCE: 67

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 68
<211> LENGTH: 18
<212> TYPE: PRT
<213> ORGANISM: Artificial Sequence
<220> FEATURE:
```

<223> OTHER INFORMATION: peptide linker sequence

<400> SEQUENCE: 68

Ser Ala Lys Thr Thr Pro Lys Leu Glu Glu Gly Glu Phe Ser Glu Ala
1               5                   10                  15

Arg Val

<210> SEQ ID NO 69
<211> LENGTH: 5
<212> TYPE: PRT
<213> ORGANISM: Artificial Sequence
<220> FEATURE:
<223> OTHER INFORMATION: peptide linker sequence

<400> SEQUENCE: 69

Ala Asp Ala Ala Pro
1               5

<210> SEQ ID NO 70
<211> LENGTH: 12
<212> TYPE: PRT
<213> ORGANISM: Artificial Sequence
<220> FEATURE:
<223> OTHER INFORMATION: peptide linker sequence

<400> SEQUENCE: 70

Ala Asp Ala Ala Pro Thr Val Ser Ile Phe Pro Pro
1               5                   10

<210> SEQ ID NO 71
<211> LENGTH: 5
<212> TYPE: PRT
<213> ORGANISM: Artificial Sequence
<220> FEATURE:
<223> OTHER INFORMATION: peptide linker sequence

<400> SEQUENCE: 71

Thr Val Ala Ala Pro
1               5

<210> SEQ ID NO 72
<211> LENGTH: 12
<212> TYPE: PRT
<213> ORGANISM: Artificial Sequence
<220> FEATURE:
<223> OTHER INFORMATION: peptide linker sequence

<400> SEQUENCE: 72

Thr Val Ala Ala Pro Ser Val Phe Ile Phe Pro Pro
1               5                   10

<210> SEQ ID NO 73
<211> LENGTH: 6
<212> TYPE: PRT
<213> ORGANISM: Artificial Sequence
<220> FEATURE:
<223> OTHER INFORMATION: peptide linker sequence

<400> SEQUENCE: 73

Gln Pro Lys Ala Ala Pro
1               5

<210> SEQ ID NO 74
<211> LENGTH: 13
<212> TYPE: PRT
<213> ORGANISM: Artificial Sequence
<220> FEATURE:
<223> OTHER INFORMATION: peptide linker sequence

<400> SEQUENCE: 74

Gln Pro Lys Ala Ala Pro Ser Val Thr Leu Phe Pro Pro
1               5                   10

<210> SEQ ID NO 75
<211> LENGTH: 6
<212> TYPE: PRT
<213> ORGANISM: Artificial Sequence
<220> FEATURE:
<223> OTHER INFORMATION: peptide linker sequence

<400> SEQUENCE: 75

Ala Lys Thr Thr Pro Pro
1               5

<210> SEQ ID NO 76
<211> LENGTH: 13
<212> TYPE: PRT
<213> ORGANISM: Artificial Sequence
<220> FEATURE:
<223> OTHER INFORMATION: peptide linker sequence

<400> SEQUENCE: 76

Ala Lys Thr Thr Pro Pro Ser Val Thr Pro Leu Ala Pro
1               5                   10

<210> SEQ ID NO 77
<211> LENGTH: 6
<212> TYPE: PRT
<213> ORGANISM: Artificial Sequence
<220> FEATURE:
<223> OTHER INFORMATION: peptide linker sequence

<400> SEQUENCE: 77

Ala Lys Thr Thr Ala Pro
1               5

<210> SEQ ID NO 78
<211> LENGTH: 13
<212> TYPE: PRT
<213> ORGANISM: Artificial Sequence
<220> FEATURE:
<223> OTHER INFORMATION: peptide linker sequence

<400> SEQUENCE: 78

Ala Lys Thr Thr Ala Pro Ser Val Tyr Pro Leu Ala Pro
1               5                   10

<210> SEQ ID NO 79
<211> LENGTH: 6
<212> TYPE: PRT
<213> ORGANISM: Artificial Sequence
<220> FEATURE:
<223> OTHER INFORMATION: peptide linker sequence

<400> SEQUENCE: 79

Ala Ser Thr Lys Gly Pro
1               5

<210> SEQ ID NO 80
<211> LENGTH: 13
<212> TYPE: PRT
<213> ORGANISM: Artificial Sequence
<220> FEATURE:

<223> OTHER INFORMATION: peptide linker sequence

<400> SEQUENCE: 80

Ala Ser Thr Lys Gly Pro Ser Val Phe Pro Leu Ala Pro
1               5                   10

<210> SEQ ID NO 81
<211> LENGTH: 9
<212> TYPE: PRT
<213> ORGANISM: Artificial Sequence
<220> FEATURE:
<223> OTHER INFORMATION: peptide linker sequence

<400> SEQUENCE: 81

Gly Gly Ser Gly Gly Gly Gly Ser Gly
1               5

<210> SEQ ID NO 82
<211> LENGTH: 15
<212> TYPE: PRT
<213> ORGANISM: Artificial Sequence
<220> FEATURE:
<223> OTHER INFORMATION: peptide linker sequence

<400> SEQUENCE: 82

Gly Gly Gly Gly Ser Gly Gly Gly Ser Gly Gly Gly Gly Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: peptide linker sequence

<400> SEQUENCE: 83

Gly Glu Asn Lys Val Glu Tyr Ala Pro Ala Leu Met Ala Leu Ser
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: peptide linker sequence

<400> SEQUENCE: 84

Gly Pro Ala Lys Glu Leu Thr Pro Leu Lys Glu Ala Lys Val Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: peptide linker sequence

<400> SEQUENCE: 85

Gly His Glu Ala Ala Ala Val Met Gln Val Gln Tyr Pro Ala Ser
1               5                   10                  15

<210> SEQ ID NO 86
<211> LENGTH: 24
<212> TYPE: PRT
<213> ORGANISM: Artificial Sequence
<220> FEATURE:
<223> OTHER INFORMATION: peptide linker sequence

<400> SEQUENCE: 86

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 87
<211> LENGTH: 26
<212> TYPE: PRT
<213> ORGANISM: Artificial Sequence
<220> FEATURE:
<223> OTHER INFORMATION: peptide linker sequence

<400> SEQUENCE: 87

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25

<210> SEQ ID NO 88
<211> LENGTH: 5
<212> TYPE: PRT
<213> ORGANISM: Artificial Sequence
<220> FEATURE:
<223> OTHER INFORMATION: peptide linker sequence

<400> SEQUENCE: 88

Gly Gly Gly Gly Ser
1               5

<210> SEQ ID NO 89
<211> LENGTH: 122
<212> TYPE: PRT
<213> ORGANISM: Mus musculus

<400> SEQUENCE: 89

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg Asn Tyr
            20                  25                  30

Gly Met Asn Trp Val Lys Gln Ala Pro Gly Lys Asp Leu Lys Arg Met
        35                  40                  45

Ala Trp Ile Asn Thr Tyr Thr Gly Glu Ser Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ile Tyr Tyr Tyr Gly Ser Ser Tyr Ala Met Asp Tyr Trp
            100                 105                 110

Gly Gln Gly Thr Ser Val Thr Val Ser Ser
        115                 120

<210> SEQ ID NO 90
<211> LENGTH: 108
<212> TYPE: PRT
<213> ORGANISM: Mus musculus

<400> SEQUENCE: 90

Asn Ile Gln Met Thr Gln Thr Thr Ser Ser Leu Ser Ala Ser Leu Gly

```
                1               5                  10                 15
           Asp Arg Val Thr Ile Ser Cys Arg Ala Ser Gln Asp Ile Ser Asn Cys
                            20                  25                  30

Leu Asn Trp Tyr Gln Gln Lys Pro Asp Gly Thr Val Lys Leu Leu Ile
                            35                  40                  45

Tyr Tyr Thr Ser Arg Leu His Ser Gly Val Pro Ser Arg Phe Ser Gly
                            50                  55                  60

Ser Gly Ser Gly Thr Asp Tyr Ser Leu Thr Ile Ser Asn Leu Glu Gln
            65                  70                  75                  80

Glu Asp Ile Ala Thr Tyr Phe Cys Gln Gln Gly Lys Thr Leu Pro Tyr
                            85                  90                  95

Ala Phe Gly Gly Gly Thr Lys Leu Glu Ile Asn Arg
                            100                 105

<210> SEQ ID NO 91
<211> LENGTH: 118
<212> TYPE: PRT
<213> ORGANISM: Mus musculus

<400> SEQUENCE: 91

Glu Val Gln Leu Gln Gln Ser Gly Ala Glu Leu Val Lys Pro Gly Ala
            1               5                  10                  15

Ser Val Lys Leu Ser Cys Thr Ala Ser Gly Leu Asn Ile Lys Asp Thr
                            20                  25                  30

Tyr Met His Trp Leu Lys Gln Arg Pro Glu Gln Gly Leu Glu Trp Ile
                            35                  40                  45

Gly Arg Ile Asp Pro Ala Asn Gly Asn Ala Lys Tyr Asp Pro Arg Phe
            50                  55                  60

Leu Gly Lys Ala Thr Ile Thr Ala Asp Thr Ser Ser Asn Thr Ala Tyr
            65                  70                  75                  80

Leu Gln Leu Ser Ser Leu Thr Ser Glu Asp Thr Ala Val Tyr Tyr Cys
                            85                  90                  95

Ala Arg Gly Asp Gly Asn Phe His Phe Asp Tyr Trp Gly Gln Gly Thr
                            100                 105                 110

Thr Leu Thr Val Ser Ser
                            115

<210> SEQ ID NO 92
<211> LENGTH: 108
<212> TYPE: PRT
<213> ORGANISM: Mus musculus

<400> SEQUENCE: 92

Asp Ile Val Met Thr Gln Ser Gln Arg Phe Met Ser Thr Ser Val Gly
            1               5                  10                  15

Asp Arg Val Ser Val Thr Cys Lys Ala Ser Gln Asn Val Gly Thr Asn
                            20                  25                  30

Ile Ala Trp Tyr Gln Gln Lys Pro Gly Gln Ser Pro Arg Ala Leu Ile
                            35                  40                  45

Tyr Ser Ala Ser Tyr Arg Tyr Ser Gly Val Pro Asp Arg Phe Thr Gly
                            50                  55                  60

Ser Gly Ser Gly Thr Asp Phe Thr Leu Thr Ile Ser Asn Val Gln Ser
            65                  70                  75                  80

Val Asp Leu Ala Glu Tyr Phe Cys Gln Gln Tyr Thr Arg Tyr Pro Leu
                            85                  90                  95

Thr Phe Gly Gly Gly Thr Lys Leu Glu Ile Lys Arg
```

<210> SEQ ID NO 93
<211> LENGTH: 114
<212> TYPE: PRT
<213> ORGANISM: Mus musculus

<400> SEQUENCE: 93

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr Leu Tyr Ser Gln Lys Phe
    50                  55                  60

Lys Asp Thr Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
            100                 105                 110

Ser Ser

<210> SEQ ID NO 94
<211> LENGTH: 107
<212> TYPE: PRT
<213> ORGANISM: Mus musculus

<400> SEQUENCE: 94

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Met Lys Arg
            100                 105

<210> SEQ ID NO 95
<211> LENGTH: 121
<212> TYPE: PRT
<213> ORGANISM: Mus musculus

<400> SEQUENCE: 95

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

```
Gly Gln Ile Tyr Pro Gly Asp Gly Asp Thr Asn Tyr Asn Gly Lys Phe
 50                  55                  60
Lys Gly Lys Ala Thr Leu Thr Ala Asp Lys Ser Ser Thr Ser Tyr
 65                  70                  75                  80
Met Gln Leu Ser Gly Leu Thr Ser Glu Asp Ser Ala Met Tyr Phe Cys
                 85                  90                  95
Val Arg Phe Pro Thr Gly Asn Asp Tyr Tyr Ala Met Asp Tyr Trp Gly
            100                 105                 110
Gln Gly Thr Ser Val Thr Val Ser Ser
            115                 120
```

<210> SEQ ID NO 96
<211> LENGTH: 112
<212> TYPE: PRT
<213> ORGANISM: Mus musculus

<400> SEQUENCE: 96

```
Asn Ile Val Leu Thr Gln Ser Pro Ala Ser Leu Ala Val Ser Leu Gly
 1               5                  10                  15
Gln Arg Ala Thr Ile Ser Cys Arg Ala Ser Glu Ser Val Asp Ser Tyr
                 20                  25                  30
Gly Asn Ser Tyr Met His Trp Tyr Gln Gln Lys Pro Gly Gln Pro Pro
             35                  40                  45
Lys Leu Leu Ile Tyr Leu Ala Ser Asn Leu Glu Ser Gly Val Pro Ala
 50                  55                  60
Arg Phe Ser Gly Ser Gly Ser Arg Thr Asp Phe Thr Leu Thr Ile Asp
 65                  70                  75                  80
Pro Val Glu Ala Asp Asp Ala Ala Thr Tyr Tyr Cys Gln Gln Asn Asn
                 85                  90                  95
Glu Asp Pro Phe Thr Phe Gly Ser Gly Thr Lys Leu Glu Ile Lys Arg
            100                 105                 110
```

<210> SEQ ID NO 97
<211> LENGTH: 122
<212> TYPE: PRT
<213> ORGANISM: Mus musculus

<400> SEQUENCE: 97

```
Gln Val His Leu Lys Glu Ser Gly Pro Gly Leu Val Ala Pro Ser Gln
 1               5                  10                  15
Ser Leu Ser Ile Thr Cys Thr Val Ser Gly Phe Ser Leu Thr Asp Tyr
                 20                  25                  30
Gly Val Ser Trp Ile Arg Gln Pro Pro Gly Lys Gly Leu Glu Trp Leu
             35                  40                  45
Gly Leu Ile Trp Gly Gly Gly Asp Thr Tyr Tyr Asn Ser Pro Leu Lys
 50                  55                  60
Ser Arg Leu Ser Ile Arg Lys Asp Asn Ser Lys Ser Gln Val Phe Leu
 65                  70                  75                  80
Lys Met Asn Ser Leu Gln Thr Asp Asp Thr Ala Val Tyr Tyr Cys Ala
                 85                  90                  95
Lys Gln Arg Thr Leu Trp Gly Tyr Asp Leu Tyr Gly Met Asp Tyr Trp
            100                 105                 110
Gly Gln Gly Thr Ser Val Thr Val Ser Ser
            115                 120
```

<210> SEQ ID NO 98
<211> LENGTH: 108

<212> TYPE: PRT
<213> ORGANISM: Mus musculus

<400> SEQUENCE: 98

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
            20                  25                  30

Met Asn Trp Tyr Gln Gln Lys Pro Gly Glu Pro Pro Lys Leu Leu Ile
        35                  40                  45

Ser Gln Gly Asn Thr Leu Arg Pro Gly Val Pro Ser Arg Phe Ser Ser
50                  55                  60

Ser Gly Ser Gly Thr Asp Phe Val Phe Ile Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg
            100                 105

<210> SEQ ID NO 99
<211> LENGTH: 118
<212> TYPE: PRT
<213> ORGANISM: Mus musculus

<400> SEQUENCE: 99

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30

Tyr Met His Trp Val Arg Gln Ser His Gly Lys Ser Leu Glu Trp Ile
        35                  40                  45

Gly Tyr Ile Ser Cys Tyr Asn Gly Phe Thr Ser Tyr Asn Pro Lys Phe
50                  55                  60

Lys Gly Lys Ala Thr Phe Thr Val Asp Thr Ser Ser Ser Thr Ala Tyr
65                  70                  75                  80

Ile Gln Phe Ser Arg Leu Thr Ser Glu Asp Ser Ala Val Tyr Tyr Cys
                85                  90                  95

Ala Arg Ser Asp Tyr Tyr Gly Thr Asn Asp Tyr Trp Gly Gln Gly Thr
            100                 105                 110

Thr Leu Thr Val Ser Ser
        115

<210> SEQ ID NO 100
<211> LENGTH: 107
<212> TYPE: PRT
<213> ORGANISM: Mus musculus

<400> SEQUENCE: 100

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Ala Ser Pro Lys Leu Trp Ile Tyr
        35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Val Ser Arg Met Glu Ala Glu

```
                65                  70                  75                  80
Asp Ala Ala Thr Tyr Tyr Cys Gln Gln Arg Ser Thr Tyr Pro Tyr Thr
                        85                  90                  95

Phe Gly Gly Gly Thr Lys Leu Glu Ile Lys Arg
            100                 105

<210> SEQ ID NO 101
<211> LENGTH: 22
<212> TYPE: DNA
<213> ORGANISM: Artificial Sequence
<220> FEATURE:
<223> OTHER INFORMATION: PCR primer for light chain variable domain
      3D12.E3

<400> SEQUENCE: 101
atggtgtcca cagctcagtt cc                                                  22

<210> SEQ ID NO 102
<211> LENGTH: 29
<212> TYPE: DNA
<213> ORGANISM: Artificial Sequence
<220> FEATURE:
<223> OTHER INFORMATION: PCR primer for light chain variable domain of
      3D12.E3

<400> SEQUENCE: 102
gcagccaccg tacgccggtt tatttccag                                           29

<210> SEQ ID NO 103
<211> LENGTH: 24
<212> TYPE: DNA
<213> ORGANISM: Artificial Sequence
<220> FEATURE:
<223> OTHER INFORMATION: PCR primer for human Ckappa gene

<400> SEQUENCE: 103
cgtacggtgg ctgcaccatc tgtc                                                24

<210> SEQ ID NO 104
<211> LENGTH: 23
<212> TYPE: DNA
<213> ORGANISM: Artificial Sequence
<220> FEATURE:
<223> OTHER INFORMATION: PCR primer for human Ckappa gene

<400> SEQUENCE: 104
tcaacactct cccctgttga agc                                                 23

<210> SEQ ID NO 105
<211> LENGTH: 22
<212> TYPE: DNA
<213> ORGANISM: Artificial Sequence
<220> FEATURE:
<223> OTHER INFORMATION: PCR primer for heavy chain variable domain of
      3D12.E3

<400> SEQUENCE: 105
atggcttggg tgtggacctt gc                                                  22

<210> SEQ ID NO 106
<211> LENGTH: 37
<212> TYPE: DNA
<213> ORGANISM: Artificial Sequence
<220> FEATURE:
<223> OTHER INFORMATION: PCR primer for heavy chain variable domain of
      3D12.E3
```

```
<400> SEQUENCE: 106
gggcccttgg tcgacgctga ggagacggtg actgagg                          37

<210> SEQ ID NO 107
<211> LENGTH: 28
<212> TYPE: DNA
<213> ORGANISM: Artificial Sequence
<220> FEATURE:
<223> OTHER INFORMATION: PCR primer for human Cgamma1 gene

<400> SEQUENCE: 107
gcgtcgacca agggcccatc ggtcttcc                                    28

<210> SEQ ID NO 108
<211> LENGTH: 26
<212> TYPE: DNA
<213> ORGANISM: Artificial Sequence
<220> FEATURE:
<223> OTHER INFORMATION: PCR primer for human Cgamma1 gene

<400> SEQUENCE: 108
tcatttaccc ggagacaggg agaggc                                      26

<210> SEQ ID NO 109
<211> LENGTH: 24
<212> TYPE: DNA
<213> ORGANISM: Artificial Sequence
<220> FEATURE:
<223> OTHER INFORMATION: PCR primer for heavy chain variable domain of
      13F5.G5

<400> SEQUENCE: 109
atagaatgga gctgggtttt cctc                                        24

<210> SEQ ID NO 110
<211> LENGTH: 35
<212> TYPE: DNA
<213> ORGANISM: Artificial Sequence
<220> FEATURE:
<223> OTHER INFORMATION: PCR primer for heavy chain variable domain of
      13F5.G5

<400> SEQUENCE: 110
gggcccttgg tcgacgctga ggagacggtg actga                            35

<210> SEQ ID NO 111
<211> LENGTH: 24
<212> TYPE: DNA
<213> ORGANISM: Artificial Sequence
<220> FEATURE:
<223> OTHER INFORMATION: PCR primer for light chain variable domain of
      13F5.G5

<400> SEQUENCE: 111
atggtcctca tgtccttgct gttc                                        24

<210> SEQ ID NO 112
<211> LENGTH: 34
<212> TYPE: DNA
<213> ORGANISM: Artificial Sequence
<220> FEATURE:
<223> OTHER INFORMATION: PCR primer for light chain variable domain of
      13F5.G5

<400> SEQUENCE: 112
```
gcagccaccg tacgccgttt tatttccagc tttg                                34

<210> SEQ ID NO 113
<211> LENGTH: 23
<212> TYPE: DNA
<213> ORGANISM: Artificial Sequence
<220> FEATURE:
<223> OTHER INFORMATION: PCR primer for heavy chain variable domain of
      3D12.E3

<400> SEQUENCE: 113
cagatccagt tggtgcagtc tgg                                            23

<210> SEQ ID NO 114
<211> LENGTH: 35
<212> TYPE: DNA
<213> ORGANISM: Artificial Sequence
<220> FEATURE:
<223> OTHER INFORMATION: PCR primer for heavy chain variable domain of
      13F5.G5

<400> SEQUENCE: 114
caccaactgg atctgtgagg agacggtgac tgagg                               35

<210> SEQ ID NO 115
<211> LENGTH: 27
<212> TYPE: DNA
<213> ORGANISM: Artificial Sequence
<220> FEATURE:
<223> OTHER INFORMATION: PCR primer for light chain variable domain of
      3D12.E3

<400> SEQUENCE: 115
aatatccaga tgacacagac tacatcc                                        27

<210> SEQ ID NO 116
<211> LENGTH: 36
<212> TYPE: DNA
<213> ORGANISM: Artificial Sequence
<220> FEATURE:
<223> OTHER INFORMATION: PCR primer for light chain variable domain of
      13F5.G5

<400> SEQUENCE: 116
gtgtcatctg gatattccgt tttatttcca gctttg                              36

<210> SEQ ID NO 117
<211> LENGTH: 23
<212> TYPE: DNA
<213> ORGANISM: Artificial Sequence
<220> FEATURE:
<223> OTHER INFORMATION: PCR primer for heavy chain variable domain of
      13F5.G5

<400> SEQUENCE: 117
tgggggtgtc gttttggctg agg                                            23

<210> SEQ ID NO 118
<211> LENGTH: 36
<212> TYPE: DNA
<213> ORGANISM: Artificial Sequence
<220> FEATURE:
<223> OTHER INFORMATION: PCR primer for heavy chain variable domain of
      3D12.E3

<400> SEQUENCE: 118
gccaaaacga caccccacaa gatccagttg gtgcag                              36

<210> SEQ ID NO 119
<211> LENGTH: 27
<212> TYPE: DNA
<213> ORGANISM: Artificial Sequence
<220> FEATURE:
<223> OTHER INFORMATION: PCR primer for light chain variable domain of 13F5.G5

<400> SEQUENCE: 119
tggtgcagca tcagcccgtt ttatttc                                          27

<210> SEQ ID NO 120
<211> LENGTH: 33
<212> TYPE: DNA
<213> ORGANISM: Artificial Sequence
<220> FEATURE:
<223> OTHER INFORMATION: PCR primer for light chain variable domain of 3D12.E3

<400> SEQUENCE: 120
gctgatgctg caccaaatat ccagatgaca cag                                   33

<210> SEQ ID NO 121
<211> LENGTH: 243
<212> TYPE: PRT
<213> ORGANISM: Artificial Sequence
<220> FEATURE:
<223> OTHER INFORMATION: IL-1alpha/beta DVD-Ig tandem heavy variable domains

<400> SEQUENCE: 121

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ser Tyr
65                  70                  75                  80

Met Gln Leu Ser Gly Leu Thr Ser Glu Asp Ser Ala Met Tyr Phe Cys
                85                  90                  95

Val Arg Phe Pro Thr Gly Asn Asp Tyr Tyr Ala Met Asp Tyr Trp Gly
            100                 105                 110

Gln Gly Thr Ser Val Thr Val Ser Ser Gln Ile Gln Leu Val Gln Ser
        115                 120                 125

Gly Pro Glu Leu Lys Lys Pro Gly Glu Thr Val Lys Ile Ser Cys Lys
    130                 135                 140

Ala Ser Gly Tyr Thr Phe Arg Asn Tyr Gly Met Asn Trp Val Lys Gln
145                 150                 155                 160

Ala Pro Gly Lys Asp Leu Lys Arg Met Ala Trp Ile Asn Thr Tyr Thr
                165                 170                 175

Gly Glu Ser Thr Tyr Ala Asp Asp Phe Lys Gly Arg Phe Ala Phe Ser
            180                 185                 190

Leu Glu Thr Ser Ala Ser Thr Ala Tyr Leu Gln Ile Asn Asn Leu Lys
        195                 200                 205

Asn Glu Asp Thr Ala Thr Tyr Phe Cys Ala Arg Gly Ile Tyr Tyr Tyr
    210                 215                 220

```
Gly Ser Ser Tyr Ala Met Asp Tyr Trp Gly Gln Gly Thr Ser Val Thr
225                 230                 235                 240

Val Ser Ser

<210> SEQ ID NO 122
<211> LENGTH: 330
<212> TYPE: PRT
<213> ORGANISM: Homo sapiens

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 123
```

<211> LENGTH: 221
<212> TYPE: PRT
<213> ORGANISM: Artificial Sequence
<220> FEATURE:
<223> OTHER INFORMATION: IL-1alpha/beta DVD-Ig tandem light chain variable domains

<400> SEQUENCE: 123

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Phe Thr Phe Gly Ser Gly Thr Lys Leu Glu Ile Lys Arg
            100                 105                 110

Asn Ile Gln Met Thr Gln Thr Thr Ser Ser Leu Ser Ala Ser Leu Gly
        115                 120                 125

Asp Arg Val Thr Ile Ser Cys Arg Ala Ser Gln Asp Ile Ser Asn Cys
    130                 135                 140

Leu Asn Trp Tyr Gln Gln Lys Pro Asp Gly Thr Val Lys Leu Leu Ile
145                 150                 155                 160

Tyr Tyr Thr Ser Arg Leu His Ser Gly Val Pro Ser Arg Phe Ser Gly
                165                 170                 175

Ser Gly Ser Gly Thr Asp Tyr Ser Leu Thr Ile Ser Asn Leu Glu Gln
            180                 185                 190

Glu Asp Ile Ala Thr Tyr Phe Cys Gln Gln Gly Lys Thr Leu Pro Tyr
        195                 200                 205

Ala Phe Gly Gly Gly Thr Lys Leu Glu Ile Asn Arg Arg
    210                 215                 220

<210> SEQ ID NO 124
<211> LENGTH: 106
<212> TYPE: PRT
<213> ORGANISM: Homo sapiens

<400> SEQUENCE: 124

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 125
<211> LENGTH: 249
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 125

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Thr Ser Thr Tyr
65                  70                  75                  80

Met Gln Leu Ser Gly Leu Thr Ser Glu Asp Ser Ala Met Tyr Phe Cys
                85                  90                  95

Val Arg Phe Pro Thr Gly Asn Asp Tyr Tyr Ala Met Asp Tyr Trp Gly
                100                 105                 110

Gln Gly Thr Ser Val Thr Val Ser Ser Ala Lys Thr Thr Pro Pro Gln
            115                 120                 125

Ile Gln Leu Val Gln Ser Gly Pro Glu Leu Lys Lys Pro Gly Glu Thr
        130                 135                 140

Val Lys Ile Ser Cys Lys Ala Ser Gly Tyr Thr Phe Arg Asn Tyr Gly
145                 150                 155                 160

Met Asn Trp Val Lys Gln Ala Pro Gly Lys Asp Leu Lys Arg Met Ala
                165                 170                 175

Trp Ile Asn Thr Tyr Thr Gly Glu Ser Thr Tyr Ala Asp Asp Phe Lys
                180                 185                 190

Gly Arg Phe Ala Phe Ser Leu Glu Thr Ser Ala Ser Thr Ala Tyr Leu
            195                 200                 205

Gln Ile Asn Asn Leu Lys Asn Glu Asp Thr Ala Thr Tyr Phe Cys Ala
        210                 215                 220

Arg Gly Ile Tyr Tyr Tyr Gly Ser Ser Tyr Ala Met Asp Tyr Trp Gly
225                 230                 235                 240

Gln Gly Thr Ser Val Thr Val Ser Ser
                245

<210> SEQ ID NO 126
<211> LENGTH: 225
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 126

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Ser Tyr Met His Trp Tyr Gln Gln Lys Pro Gly Gln Pro Pro
            35                  40                  45

```
Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Phe Thr Phe Gly Ser Gly Thr Lys Leu Glu Ile Lys Arg
            100                 105                 110

Ala Asp Ala Ala Pro Asn Ile Gln Met Thr Gln Thr Thr Ser Ser Leu
            115                 120                 125

Ser Ala Ser Leu Gly Asp Arg Val Thr Ile Ser Cys Arg Ala Ser Gln
        130                 135                 140

Asp Ile Ser Asn Cys Leu Asn Trp Tyr Gln Gln Lys Pro Asp Gly Thr
145                 150                 155                 160

Val Lys Leu Leu Ile Tyr Tyr Thr Ser Arg Leu His Ser Gly Val Pro
                165                 170                 175

Ser Arg Phe Ser Gly Ser Gly Ser Gly Thr Asp Tyr Ser Leu Thr Ile
            180                 185                 190

Ser Asn Leu Glu Gln Glu Asp Ile Ala Thr Tyr Phe Cys Gln Gln Gly
        195                 200                 205

Lys Thr Leu Pro Tyr Ala Phe Gly Gly Gly Thr Lys Leu Glu Ile Asn
    210                 215                 220

Arg
225

<210> SEQ ID NO 127
<211> LENGTH: 246
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 127

Glu Val Gln Leu Gln Gln Ser Gly Ala Glu Leu Val Lys Pro Gly Ala
  1               5                  10                  15

Ser Val Lys Leu Ser Cys Thr Ala Ser Gly Leu Asn Ile Lys Asp Thr
             20                  25                  30

Tyr Met His Trp Leu Lys Gln Arg Pro Glu Gln Gly Leu Glu Trp Ile
         35                  40                  45

Gly Arg Ile Asp Pro Ala Asn Gly Asn Ala Lys Tyr Asp Pro Arg Phe
     50                  55                  60

Leu Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Arg Gly Asp Gly Asn Phe His Phe Asp Tyr Trp Gly Gln Gly Thr
            100                 105                 110

Thr Leu Thr Val Ser Ser Ala Ser Thr Lys Gly Pro Gln Val His Leu
            115                 120                 125

Lys Glu Ser Gly Pro Gly Leu Val Ala Pro Ser Gln Ser Leu Ser Ile
        130                 135                 140

Thr Cys Thr Val Ser Gly Phe Ser Leu Thr Asp Tyr Gly Val Ser Trp
145                 150                 155                 160

Ile Arg Gln Pro Pro Gly Lys Gly Leu Glu Trp Leu Gly Leu Ile Trp
```

```
                    165                 170                 175
Gly Gly Gly Asp Thr Tyr Tyr Asn Ser Pro Leu Lys Ser Arg Leu Ser
            180                 185                 190

Ile Arg Lys Asp Asn Ser Lys Ser Gln Val Phe Leu Lys Met Asn Ser
            195                 200                 205

Leu Gln Thr Asp Asp Thr Ala Val Tyr Tyr Cys Ala Lys Gln Arg Thr
            210                 215                 220

Leu Trp Gly Tyr Asp Leu Tyr Gly Met Asp Tyr Trp Gly Gln Gly Thr
225                 230                 235                 240

Ser Val Thr Val Ser Ser
                245

<210> SEQ ID NO 128
<211> LENGTH: 222
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 128

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Arg Ala Leu Ile
            35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Val Asp Leu Ala Glu Tyr Phe Cys Gln Gln Tyr Thr Arg Tyr Pro Leu
                85                  90                  95

Thr Phe Gly Gly Gly Thr Lys Leu Glu Ile Lys Arg Thr Val Ala Ala
            100                 105                 110

Pro Glu Thr Thr Val Thr Gln Ser Pro Ala Ser Leu Ser Met Ala Ile
            115                 120                 125

Gly Glu Lys Val Thr Ile Arg Cys Ile Thr Ser Thr Asp Ile Asp Val
130                 135                 140

Asp Met Asn Trp Tyr Gln Gln Lys Pro Gly Glu Pro Pro Lys Leu Leu
145                 150                 155                 160

Ile Ser Gln Gly Asn Thr Leu Arg Pro Gly Val Pro Ser Arg Phe Ser
                165                 170                 175

Ser Ser Gly Ser Gly Thr Asp Phe Val Phe Ile Ile Glu Asn Met Leu
            180                 185                 190

Ser Glu Asp Val Ala Asp Tyr Tyr Cys Leu Gln Ser Asp Asn Leu Pro
            195                 200                 205

Leu Thr Phe Gly Ala Gly Thr Lys Leu Glu Leu Lys Arg Arg
210                 215                 220

<210> SEQ ID NO 129
<211> LENGTH: 246
<212> TYPE: PRT
<213> ORGANISM: Artificial Sequence
<220> FEATURE:
<223> OTHER INFORMATION: IL-1alpha/beta DVD-Ig tandem heavy chain
      variable domains
```

```
<400> SEQUENCE: 129

Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Asp Thr Tyr Tyr Asn Ser Pro Leu Lys
    50                  55                  60

Ser Arg Leu Ser Ile Arg Lys Asp Asn Ser Lys Ser Gln Val Phe Leu
65              70                  75                  80

Lys Met Asn Ser Leu Gln Thr Asp Asp Thr Ala Val Tyr Tyr Cys Ala
            85                  90                  95

Lys Gln Arg Thr Leu Trp Gly Tyr Asp Leu Tyr Gly Met Asp Tyr Trp
            100                 105                 110

Gly Gln Gly Thr Ser Val Thr Val Ser Ser Ala Ser Thr Lys Gly Pro
        115                 120                 125

Glu Val Gln Leu Gln Gln Ser Gly Ala Glu Leu Val Lys Pro Gly Ala
    130                 135                 140

Ser Val Lys Leu Ser Cys Thr Ala Ser Gly Leu Asn Ile Lys Asp Thr
145             150                 155                 160

Tyr Met His Trp Leu Lys Gln Arg Pro Glu Gln Gly Leu Glu Trp Ile
            165                 170                 175

Gly Arg Ile Asp Pro Ala Asn Gly Asn Ala Lys Tyr Asp Pro Arg Phe
        180                 185                 190

Leu Gly Lys Ala Thr Ile Thr Ala Asp Thr Ser Ser Asn Thr Ala Tyr
    195                 200                 205

Leu Gln Leu Ser Ser Leu Thr Ser Glu Asp Thr Ala Val Tyr Tyr Cys
    210                 215                 220

Ala Arg Gly Asp Gly Asn Phe His Phe Asp Tyr Trp Gly Gln Gly Thr
225                 230                 235                 240

Thr Leu Thr Val Ser Ser
                245

<210> SEQ ID NO 130
<211> LENGTH: 221
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 130

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
            20                  25                  30

Met Asn Trp Tyr Gln Gln Lys Pro Gly Glu Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Val Phe Ile Ile Glu Asn Met Leu Ser
65              70                  75                  80

Glu Asp Val Ala Asp Tyr Tyr Cys Leu Gln Ser Asp Asn Leu Pro Leu
            85                  90                  95
```

```
Thr Phe Gly Ala Gly Thr Lys Leu Glu Leu Lys Arg Thr Val Ala Ala
                100                 105                 110

Pro Asp Ile Val Met Thr Gln Ser Gln Arg Phe Met Ser Thr Ser Val
            115                 120                 125

Gly Asp Arg Val Ser Val Thr Cys Lys Ala Ser Gln Asn Val Gly Thr
        130                 135                 140

Asn Ile Ala Trp Tyr Gln Gln Lys Pro Gly Gln Ser Pro Arg Ala Leu
145                 150                 155                 160

Ile Tyr Ser Ala Ser Tyr Arg Tyr Ser Gly Val Pro Asp Arg Phe Thr
                165                 170                 175

Gly Ser Gly Ser Gly Thr Asp Phe Thr Leu Thr Ile Ser Asn Val Gln
            180                 185                 190

Ser Val Asp Leu Ala Glu Tyr Phe Cys Gln Gln Tyr Thr Arg Tyr Pro
        195                 200                 205

Leu Thr Phe Gly Gly Gly Thr Lys Leu Glu Ile Lys Arg
    210                 215                 220

<210> SEQ ID NO 131
<211> LENGTH: 253
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 131

Glu Val Gln Leu Gln Gln Ser Gly Ala Glu Leu Val Lys Pro Gly Ala
1               5                   10                  15

Ser Val Lys Leu Ser Cys Thr Ala Ser Gly Leu Asn Ile Lys Asp Thr
            20                  25                  30

Tyr Met His Trp Leu Lys Gln Arg Pro Glu Gln Gly Leu Glu Trp Ile
        35                  40                  45

Gly Arg Ile Asp Pro Ala Asn Gly Asn Ala Lys Tyr Asp Pro Arg Phe
    50                  55                  60

Leu Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Asp Gly Asn Phe His Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Gln Val His Leu Lys Glu Ser Gly Pro Gly Leu Val Ala
    130                 135                 140

Pro Ser Gln Ser Leu Ser Ile Thr Cys Thr Val Ser Gly Phe Ser Leu
145                 150                 155                 160

Thr Asp Tyr Gly Val Ser Trp Ile Arg Gln Pro Pro Gly Lys Gly Leu
                165                 170                 175

Glu Trp Leu Gly Leu Ile Trp Gly Gly Gly Asp Thr Tyr Tyr Asn Ser
            180                 185                 190

Pro Leu Lys Ser Arg Leu Ser Ile Arg Lys Asp Asn Ser Lys Ser Gln
    195                 200                 205

Val Phe Leu Lys Met Asn Ser Leu Gln Thr Asp Asp Thr Ala Val Tyr
210                 215                 220

Tyr Cys Ala Lys Gln Arg Thr Leu Trp Gly Tyr Asp Leu Tyr Gly Met
225                 230                 235                 240
```

Asp Tyr Trp Gly Gln Gly Thr Ser Val Thr Val Ser Ser
            245                 250

<210> SEQ ID NO 132
<211> LENGTH: 228
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 132

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Arg Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Val Asp Leu Ala Glu Tyr Phe Cys Gln Gln Tyr Thr Arg Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Glu Thr Thr Val Thr Gln Ser Pro
        115                 120                 125

Ala Ser Leu Ser Met Ala Ile Gly Glu Lys Val Thr Ile Arg Cys Ile
    130                 135                 140

Thr Ser Thr Asp Ile Asp Val Asp Met Asn Trp Tyr Gln Gln Lys Pro
145                 150                 155                 160

Gly Glu Pro Pro Lys Leu Leu Ile Ser Gln Gly Asn Thr Leu Arg Pro
                165                 170                 175

Gly Val Pro Ser Arg Phe Ser Ser Ser Gly Ser Gly Thr Asp Phe Val
            180                 185                 190

Phe Ile Ile Glu Asn Met Leu Ser Glu Asp Val Ala Asp Tyr Tyr Cys
        195                 200                 205

Leu Gln Ser Asp Asn Leu Pro Leu Thr Phe Gly Ala Gly Thr Lys Leu
    210                 215                 220

Glu Leu Lys Arg
225

<210> SEQ ID NO 133
<211> LENGTH: 253
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 133

Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

```
Gly Leu Ile Trp Gly Gly Asp Thr Tyr Tyr Asn Ser Pro Leu Lys
    50                  55                  60

Ser Arg Leu Ser Ile Arg Lys Asp Asn Ser Lys Ser Gln Val Phe Leu
 65                  70                  75                  80

Lys Met Asn Ser Leu Gln Thr Asp Asp Thr Ala Val Tyr Tyr Cys Ala
                 85                  90                  95

Lys Gln Arg Thr Leu Trp Gly Tyr Asp Leu Tyr Gly Met Asp Tyr Trp
                100                 105                 110

Gly Gln Gly Thr Ser Val Thr Val Ser Ser Ala Ser Thr Lys Gly Pro
            115                 120                 125

Ser Val Phe Pro Leu Ala Pro Glu Val Gln Leu Gln Gln Ser Gly Ala
130                 135                 140

Glu Leu Val Lys Pro Gly Ala Ser Val Lys Leu Ser Cys Thr Ala Ser
145                 150                 155                 160

Gly Leu Asn Ile Lys Asp Thr Tyr Met His Trp Leu Lys Gln Arg Pro
                165                 170                 175

Glu Gln Gly Leu Glu Trp Ile Gly Arg Ile Asp Pro Ala Asn Gly Asn
            180                 185                 190

Ala Lys Tyr Asp Pro Arg Phe Leu Gly Lys Ala Thr Ile Thr Ala Asp
        195                 200                 205

Thr Ser Ser Asn Thr Ala Tyr Leu Gln Leu Ser Ser Leu Thr Ser Glu
    210                 215                 220

Asp Thr Ala Val Tyr Tyr Cys Ala Arg Gly Asp Gly Asn Phe His Phe
225                 230                 235                 240

Asp Tyr Trp Gly Gln Gly Thr Thr Leu Thr Val Ser Ser
                245                 250
```

<210> SEQ ID NO 134
<211> LENGTH: 228
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 134

```
Glu Thr Thr Val Thr Gln Ser Pro Ala Ser Leu Ser Met Ala Ile Gly
 1               5                  10                  15

Glu Lys Val Thr Ile Arg Cys Ile Thr Ser Thr Asp Ile Asp Val Asp
                 20                  25                  30

Met Asn Trp Tyr Gln Gln Lys Pro Gly Glu Pro Pro Lys Leu Leu Ile
             35                  40                  45

Ser Gln Gly Asn Thr Leu Arg Pro Gly Val Pro Ser Arg Phe Ser Ser
     50                  55                  60

Ser Gly Ser Gly Thr Asp Phe Val Phe Ile Ile Glu Asn Met Leu Ser
 65                  70                  75                  80

Glu Asp Val Ala Asp Tyr Tyr Cys Leu Gln Ser Asp Asn Leu Pro Leu
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Asp Ile Val Met Thr Gln Ser Gln
            115                 120                 125

Arg Phe Met Ser Thr Ser Val Gly Asp Arg Val Ser Val Thr Cys Lys
        130                 135                 140

Ala Ser Gln Asn Val Gly Thr Asn Ile Ala Trp Tyr Gln Gln Lys Pro
```

```
145                 150                 155                 160
Gly Gln Ser Pro Arg Ala Leu Ile Tyr Ser Ala Ser Tyr Arg Tyr Ser
                165                 170                 175

Gly Val Pro Asp Arg Phe Thr Gly Ser Gly Ser Gly Thr Asp Phe Thr
                180                 185                 190

Leu Thr Ile Ser Asn Val Gln Ser Val Asp Leu Ala Glu Tyr Phe Cys
                195                 200                 205

Gln Gln Tyr Thr Arg Tyr Pro Leu Thr Phe Gly Gly Gly Thr Lys Leu
                210                 215                 220

Glu Ile Lys Arg
225

<210> SEQ ID NO 135
<211> LENGTH: 238
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 135

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
                20                  25                  30

Trp Met Asn Trp Val Lys Gln Arg Pro Glu Gln Gly Leu Glu Trp Ile
                35                  40                  45

Gly Arg Ile Asp Pro Tyr Asp Ser Glu Thr Leu Tyr Ser Gln Lys Phe
            50                  55                  60

Lys Asp Thr Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
                100                 105                 110

Ser Ser Ala Ser Thr Lys Gly Pro Glu Val Gln Leu Gln Gln Ser Gly
                115                 120                 125

Pro Glu Leu Val Lys Thr Gly Thr Ser Val Lys Ile Ser Cys Lys Ala
            130                 135                 140

Ser Gly Tyr Ser Phe Thr Gly Tyr Tyr Met His Trp Val Arg Gln Ser
145                 150                 155                 160

His Gly Lys Ser Leu Glu Trp Ile Gly Tyr Ile Ser Cys Tyr Asn Gly
                165                 170                 175

Phe Thr Ser Tyr Asn Pro Lys Phe Lys Gly Lys Ala Thr Phe Thr Val
                180                 185                 190

Asp Thr Ser Ser Ser Thr Ala Tyr Ile Gln Phe Ser Arg Leu Thr Ser
                195                 200                 205

Glu Asp Ser Ala Val Tyr Tyr Cys Ala Arg Ser Asp Tyr Tyr Gly Thr
                210                 215                 220

Asn Asp Tyr Trp Gly Gln Gly Thr Thr Leu Thr Val Ser Ser
225                 230                 235

<210> SEQ ID NO 136
<211> LENGTH: 219
<212> TYPE: PRT
<213> ORGANISM: Artificial Sequence
<220> FEATURE:
```

<223> OTHER INFORMATION: IL-1alpha/beta DVD-Ig tandem light chain
    variable domains

<400> SEQUENCE: 136

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Met Lys Arg Thr Val Ala Ala Pro
            100                 105                 110

Gln Ile Val Leu Thr Gln Ser Pro Ala Ile Met Ser Ala Ser Pro Gly
        115                 120                 125

Glu Lys Val Thr Ile Thr Cys Ser Ala Ser Ser Ser Val Ser Tyr Met
    130                 135                 140

His Trp Phe Gln Gln Lys Pro Gly Ala Ser Pro Lys Leu Trp Ile Tyr
145                 150                 155                 160

Ser Thr Ser Asn Leu Ala Ser Gly Val Pro Ala Arg Phe Ser Gly Ser
                165                 170                 175

Gly Ser Gly Thr Ser Tyr Ser Leu Thr Val Ser Arg Met Glu Ala Glu
            180                 185                 190

Asp Ala Ala Thr Tyr Tyr Cys Gln Gln Arg Ser Thr Tyr Pro Tyr Thr
        195                 200                 205

Phe Gly Gly Gly Thr Lys Leu Glu Ile Lys Arg
    210                 215

<210> SEQ ID NO 137
<211> LENGTH: 238
<212> TYPE: PRT
<213> ORGANISM: Artificial Sequence
<220> FEATURE:
<223> OTHER INFORMATION: IL-1alpha/beta DVD-Ig tandem heavy chain
    variable domains

<400> SEQUENCE: 137

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30

Tyr Met His Trp Val Arg Gln Ser His Gly Lys Ser Leu Glu Trp Ile
        35                  40                  45

Gly Tyr Ile Ser Cys Tyr Asn Gly Phe Thr Ser Tyr Asn Pro Lys Phe
    50                  55                  60

Lys Gly Lys Ala Thr Phe Thr Val Asp Thr Ser Ser Ser Thr Ala Tyr
65                  70                  75                  80

Ile Gln Phe Ser Arg Leu Thr Ser Glu Asp Ser Ala Val Tyr Tyr Cys
                85                  90                  95

Ala Arg Ser Asp Tyr Tyr Gly Thr Asn Asp Tyr Trp Gly Gln Gly Thr
            100                 105                 110

```
Thr Leu Thr Val Ser Ser Ala Ser Thr Lys Gly Pro Gln Val Gln Leu
            115                 120                 125

Gln Gln Pro Gly Ala Glu Leu Val Arg Pro Gly Ala Ser Val Lys Leu
130                 135                 140

Ser Cys Lys Ala Ser Gly Tyr Thr Phe Thr Tyr Trp Met Asn Trp
145                 150                 155                 160

Val Lys Gln Arg Pro Glu Gln Gly Leu Glu Trp Ile Gly Arg Ile Asp
                165                 170                 175

Pro Tyr Asp Ser Glu Thr Leu Tyr Ser Gln Lys Phe Lys Asp Thr Ala
            180                 185                 190

Ile Leu Thr Val Asp Lys Ser Ser Thr Ala Tyr Met Gln Leu Ser
        195                 200                 205

Ser Leu Thr Ser Glu Asp Ser Ala Val Tyr Tyr Cys Ala Arg Tyr Gly
    210                 215                 220

Phe Asp Tyr Trp Gly Gln Gly Thr Thr Leu Thr Val Ser Ser
225                 230                 235
```

```
<210> SEQ ID NO 138
<211> LENGTH: 219
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 138

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Ala Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95

Phe Gly Gly Gly Thr Lys Leu Glu Ile Lys Arg Thr Val Ala Ala Pro
            100                 105                 110

Gln Ile Val Leu Thr Gln Ser Pro Ala Leu Met Ser Ala Ser Pro Gly
        115                 120                 125

Glu Lys Val Thr Met Thr Cys Ser Ala Ser Ser Ser Val Asn Tyr Met
130                 135                 140

Tyr Trp Tyr Gln Gln Lys Pro Arg Ser Ser Pro Lys Pro Trp Ile Tyr
145                 150                 155                 160

Leu Thr Ser Asn Leu Ala Ser Gly Val Pro Ala Arg Phe Ser Gly Ser
                165                 170                 175

Gly Ser Gly Thr Ser Tyr Ser Leu Thr Ile Ser Ser Met Glu Ala Glu
            180                 185                 190

Asp Ala Ala Thr Tyr Tyr Cys Gln Gln Trp Asn Ser Asn Pro Tyr Thr
        195                 200                 205

Phe Gly Gly Gly Thr Lys Leu Glu Met Lys Arg
210                 215
```

```
<210> SEQ ID NO 139
```

<211> LENGTH: 245
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 139

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr Leu Tyr Ser Gln Lys Phe
50                  55                  60

Lys Asp Thr Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
            100                 105                 110

Ser Ser Ala Ser Thr Lys Gly Pro Ser Val Phe Pro Leu Ala Pro Glu
        115                 120                 125

Val Gln Leu Gln Gln Ser Gly Pro Glu Leu Val Lys Thr Gly Thr Ser
130                 135                 140

Val Lys Ile Ser Cys Lys Ala Ser Gly Tyr Ser Phe Thr Gly Tyr Tyr
145                 150                 155                 160

Met His Trp Val Arg Gln Ser His Gly Lys Ser Leu Glu Trp Ile Gly
                165                 170                 175

Tyr Ile Ser Cys Tyr Asn Gly Phe Thr Ser Tyr Asn Pro Lys Phe Lys
            180                 185                 190

Gly Lys Ala Thr Phe Thr Val Asp Thr Ser Ser Ser Thr Ala Tyr Ile
        195                 200                 205

Gln Phe Ser Arg Leu Thr Ser Glu Asp Ser Ala Val Tyr Tyr Cys Ala
    210                 215                 220

Arg Ser Asp Tyr Tyr Gly Thr Asn Asp Tyr Trp Gly Gln Gly Thr Thr
225                 230                 235                 240

Leu Thr Val Ser Ser
            245

<210> SEQ ID NO 140
<211> LENGTH: 227
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 140

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
50                  55                  60

```
Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Asn Ser Asn Pro Tyr Thr
                 85                  90                  95

Phe Gly Gly Gly Thr Lys Leu Glu Met Lys Arg Thr Val Ala Ala Pro
            100                 105                 110

Ser Val Phe Ile Phe Pro Pro Gln Ile Val Leu Thr Gln Ser Pro Ala
            115                 120                 125

Ile Met Ser Ala Ser Pro Gly Glu Lys Val Thr Ile Thr Cys Ser Ala
        130                 135                 140

Ser Ser Ser Val Ser Tyr Met His Trp Phe Gln Gln Lys Pro Gly Ala
145                 150                 155                 160

Ser Pro Lys Leu Trp Ile Tyr Ser Thr Ser Asn Leu Ala Ser Gly Val
                165                 170                 175

Pro Ala Arg Phe Ser Gly Ser Gly Ser Gly Thr Ser Tyr Ser Leu Thr
            180                 185                 190

Val Ser Arg Met Glu Ala Glu Asp Ala Ala Thr Tyr Tyr Cys Gln Gln
        195                 200                 205

Arg Ser Thr Tyr Pro Tyr Thr Phe Gly Gly Gly Thr Lys Leu Glu Ile
    210                 215                 220

Lys Arg Arg
225

<210> SEQ ID NO 141
<211> LENGTH: 245
<212> TYPE: PRT
<213> ORGANISM: Artificial Sequence
<220> FEATURE:
<223> OTHER INFORMATION: IL-1alpha/beta DVD-Ig tandem heavy chain
      variable domains

<400> SEQUENCE: 141

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30

Tyr Met His Trp Val Arg Gln Ser His Gly Lys Ser Leu Glu Trp Ile
        35                  40                  45

Gly Tyr Ile Ser Cys Tyr Asn Gly Phe Thr Ser Tyr Asn Pro Lys Phe
    50                  55                  60

Lys Gly Lys Ala Thr Phe Thr Val Asp Thr Ser Ser Thr Ala Tyr
 65                  70                  75                  80

Ile Gln Phe Ser Arg Leu Thr Ser Glu Asp Ser Ala Val Tyr Tyr Cys
                 85                  90                  95

Ala Arg Ser Asp Tyr Tyr Gly Thr Asn Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Gln Val Gln Leu Gln Gln Pro Gly Ala Glu Leu Val Arg
    130                 135                 140

Pro Gly Ala Ser Val Lys Leu Ser Cys Lys Ala Ser Gly Tyr Thr Phe
145                 150                 155                 160

Thr Thr Tyr Trp Met Asn Trp Val Lys Gln Arg Pro Glu Gln Gly Leu
                165                 170                 175

Glu Trp Ile Gly Arg Ile Asp Pro Tyr Asp Ser Glu Thr Leu Tyr Ser
```

```
            180             185               190
Gln Lys Phe Lys Asp Thr Ala Ile Leu Thr Val Asp Lys Ser Ser Ser
            195                 200             205

Thr Ala Tyr Met Gln Leu Ser Ser Leu Thr Ser Glu Asp Ser Ala Val
        210                 215             220

Tyr Tyr Cys Ala Arg Tyr Gly Phe Asp Tyr Trp Gly Gln Gly Thr Thr
225                 230                 235                 240

Leu Thr Val Ser Ser
                245

<210> SEQ ID NO 142
<211> LENGTH: 227
<212> TYPE: PRT
<213> ORGANISM: Artificial Sequence
<220> FEATURE:
<223> OTHER INFORMATION: IL-1alpha/beta DVD-Ig tandem light chain
      variable domains

<400> SEQUENCE: 142

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Ala Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Gln Ile Val Leu Thr Gln Ser Pro Ala
            115                 120                 125

Leu Met Ser Ala Ser Pro Gly Glu Lys Val Thr Met Thr Cys Ser Ala
        130                 135                 140

Ser Ser Ser Val Asn Tyr Met Tyr Trp Tyr Gln Gln Lys Pro Arg Ser
145                 150                 155                 160

Ser Pro Lys Pro Trp Ile Tyr Leu Thr Ser Asn Leu Ala Ser Gly Val
                165                 170                 175

Pro Ala Arg Phe Ser Gly Ser Gly Ser Gly Thr Ser Tyr Ser Leu Thr
            180                 185                 190

Ile Ser Ser Met Glu Ala Glu Asp Ala Ala Thr Tyr Tyr Cys Gln Gln
            195                 200                 205

Trp Asn Ser Asn Pro Tyr Thr Phe Gly Gly Gly Thr Lys Leu Glu Met
        210                 215                 220

Lys Arg Arg
225

<210> SEQ ID NO 143
<211> LENGTH: 249
<212> TYPE: PRT
<213> ORGANISM: Artificial Sequence
<220> FEATURE:
<223> OTHER INFORMATION: mIL-1alpha/beta DVD-Ig tandem heavy chain
      variable domains
```

```
<400> SEQUENCE: 143

Glu Val Gln Leu Gln Gln Ser Gly Pro Glu Leu Val Lys Pro Gly Thr
1               5                   10                  15

Ser Val Lys Met Ser Cys Lys Thr Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Asn Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Asn Glu Tyr Tyr Gly Ser Ser Phe Phe Asp Tyr Trp Gly
            100                 105                 110

Gln Gly Thr Thr Leu Thr Val Ser Ser Ala Lys Thr Thr Ala Pro Ser
        115                 120                 125

Val Tyr Pro Leu Ala Pro Gln Val Ile Leu Lys Glu Ser Gly Pro Gly
    130                 135                 140

Ile Leu Gln Pro Ser Gln Thr Leu Ser Leu Thr Cys Ser Phe Ser Gly
145                 150                 155                 160

Phe Ser Leu Ser Thr Tyr Gly Thr Ala Val Asn Trp Ile Arg Gln Pro
                165                 170                 175

Ser Gly Lys Gly Leu Glu Trp Leu Ala Gln Ile Gly Ser Asp Asp Arg
            180                 185                 190

Lys Leu Tyr Asn Pro Phe Leu Lys Ser Arg Ile Thr Leu Ser Glu Asp
        195                 200                 205

Thr Ser Asn Ser Gln Val Phe Leu Lys Ile Thr Ser Val Asp Thr Glu
    210                 215                 220

Asp Ser Ala Thr Tyr Tyr Cys Ala Asn Gly Val Met Glu Tyr Trp Gly
225                 230                 235                 240

Leu Gly Thr Ser Val Thr Val Ser Ser
                245

<210> SEQ ID NO 144
<211> LENGTH: 121
<212> TYPE: PRT
<213> ORGANISM: Artificial Sequence
<220> FEATURE:
<223> OTHER INFORMATION: heavy chain variable domain of 10G11

<400> SEQUENCE: 144

Glu Val Gln Leu Gln Gln Ser Gly Pro Glu Leu Val Lys Pro Gly Thr
1               5                   10                  15

Ser Val Lys Met Ser Cys Lys Thr Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Asn Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Asn Glu Tyr Tyr Gly Ser Ser Phe Phe Asp Tyr Trp Gly
```

```
                100              105              110
Gln Gly Thr Thr Leu Thr Val Ser Ser
        115             120

<210> SEQ ID NO 145
<211> LENGTH: 115
<212> TYPE: PRT
<213> ORGANISM: Artificial Sequence
<220> FEATURE:
<223> OTHER INFORMATION: heavy chain variable domain of 9H10

<400> SEQUENCE: 145

Gln Val Ile Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Thr Ala Val Asn Trp Ile Arg Gln Pro Ser Gly Lys Gly Leu Glu
        35                  40                  45

Trp Leu Ala Gln Ile Gly Ser Asp Asp Arg Lys Leu Tyr Asn Pro Phe
    50                  55                  60

Leu Lys Ser Arg Ile Thr Leu Ser Glu Asp Thr Ser Asn Ser Gln Val
65                  70                  75                  80

Phe Leu Lys Ile Thr Ser Val Asp Thr Glu Asp Ser Ala Thr Tyr Tyr
                85                  90                  95

Cys Ala Asn Gly Val Met Glu Tyr Trp Gly Leu Gly Thr Ser Val Thr
            100                 105                 110

Val Ser Ser
        115

<210> SEQ ID NO 146
<211> LENGTH: 330
<212> TYPE: PRT
<213> ORGANISM: Mus musculus

<400> SEQUENCE: 146

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175
```

```
Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
                290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 147
<211> LENGTH: 228
<212> TYPE: PRT
<213> ORGANISM: Artificial Sequence
<220> FEATURE:
<223> OTHER INFORMATION: mIL-1alpha/beta DVD-Ig tandem light chain
      variable domains

<400> SEQUENCE: 147

Asp Ile Gln Met Thr Gln Ser Pro Ala Ser Leu Ser Ala Ser Val Gly
1               5                   10                  15

Glu Thr Val Thr Ile Thr Cys Arg Gly Ser Gly Ile Leu His Asn Tyr
                20                  25                  30

Leu Val Trp Tyr Gln Gln Lys Gln Gly Lys Ser Pro Gln Leu Leu Val
            35                  40                  45

Tyr Ser Ala Lys Ile Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ile Val Met Thr Gln Thr Pro
        115                 120                 125

Lys Phe Leu Leu Val Ser Ala Gly Asp Arg Val Thr Ile Thr Cys Lys
                130                 135                 140

Ala Ser Gln Ser Val Asn His Asp Val Ala Trp Tyr Gln Gln Met Pro
145                 150                 155                 160

Gly Gln Ser Pro Lys Leu Leu Ile Tyr Phe Ala Ser Asn Arg Tyr Thr
                165                 170                 175

Gly Val Pro Asp Arg Phe Thr Gly Ser Gly Tyr Gly Thr Asp Phe Thr
            180                 185                 190

Phe Thr Ile Ser Thr Val Gln Ala Glu Asp Leu Ala Val Tyr Phe Cys
```

```
                195                 200                 205
Gln Gln Asp Tyr Ser Ser Pro Tyr Thr Phe Gly Gly Gly Thr Lys Leu
    210                 215                 220

Glu Ile Lys Arg
225

<210> SEQ ID NO 148
<211> LENGTH: 108
<212> TYPE: PRT
<213> ORGANISM: Artificial Sequence
<220> FEATURE:
<223> OTHER INFORMATION: light chain variable domain of 10G11

<400> SEQUENCE: 148

Asp Ile Gln Met Thr Gln Ser Pro Ala Ser Leu Ser Ala Ser Val Gly
1               5                   10                  15

Glu Thr Val Thr Ile Thr Cys Arg Gly Ser Gly Ile Leu His Asn Tyr
            20                  25                  30

Leu Val Trp Tyr Gln Gln Lys Gln Gly Lys Ser Pro Gln Leu Leu Val
        35                  40                  45

Tyr Ser Ala Lys Ile Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys Arg
            100                 105

<210> SEQ ID NO 149
<211> LENGTH: 108
<212> TYPE: PRT
<213> ORGANISM: Artificial Sequence
<220> FEATURE:
<223> OTHER INFORMATION: light chain variable domain of 9H10

<400> SEQUENCE: 149

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn His Asp
            20                  25                  30

Val Ala Trp Tyr Gln Gln Met Pro Gly Gln Ser Pro Lys Leu Leu Ile
        35                  40                  45

Tyr Phe Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105

<210> SEQ ID NO 150
<211> LENGTH: 106
<212> TYPE: PRT
<213> ORGANISM: Mus musculus

<400> SEQUENCE: 150

Ala Asp Ala Ala Pro Thr Val Ser Ile Phe Pro Pro Ser Ser Glu Gln
```

```
1               5                   10                  15
Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 151
<211> LENGTH: 9
<212> TYPE: PRT
<213> ORGANISM: Homo sapiens
<220> FEATURE:
<221> NAME/KEY: MISC_FEATURE
<222> LOCATION: (2)..(9)
<223> OTHER INFORMATION: Xaa can be any amino acid

<400> SEQUENCE: 151

Cys Xaa Xaa Xaa Xaa Xaa Xaa Xaa Xaa
1               5
```

TREATMENT OF OSTEOARTHRITIS AND PAIN

CROSS-REFERENCE TO RELATED APPLICATION

This application claims the benefit of priority to U.S. Provisional Application No. 61/440,853, filed Feb. 8, 2011, the entire contents of which are incorporated herein by reference.

FIELD OF THE INVENTION

The present invention relates to the treatment of osteoarthritis and pain, and more specifically to the use of proteins that bind IL-1α and/or IL-1β to treat osteoarthritis and pain.

BACKGROUND OF THE INVENTION

The articular cartilage, or "hyaline cartilage", of healthy vertebrates (including humans and other mammals) is a semi-transparent, opalescent connective tissue characterized by a columnar growth pattern of chondrocytes in an extracellular matrix (ECM) composed predominantly of proteoglycans, type II collagen, and water. Articular cartilage provides an effective weight-bearing cushion to prevent contact between opposing bones in a joint and thus is critical to the normal function of the joint. Articular cartilage is not only susceptible to damage by joint trauma, but also to a gradual process of erosion. Initially, such an erosion may be simply an asymptomatic "partial thickness defect" in which an area of reduced hyaline cartilage does not penetrate completely to the subchondral bone. Such partial thickness defects are usually not painful and typically are only detected during arthroscopic examination. However, if the erosive process is not treated, the base of a partial thickness defect may continue to wear away and the diameter of the defect may increase such that the defect eventually progresses to a "full thickness defect" that penetrates the underlying bone. Such full thickness defects may become sufficiently large that surfaces of opposing bones of the joint make contact and begin to erode one another, leading to inflammation, pain, and other degenerative changes, i.e., the classic symptoms of osteoarthritis (OA). Osteoarthritis is thus a degenerative, progressive, and crippling disease that results in joint deformity, instability, impairment, and pain. Eventually, joint replacement surgery may be the only practical recourse for restoring, at least in part, some level of mobility to an individual.

The IL-1 superfamily is comprised of mediators of inflammatory processes with a wide range of biological and physiological effects, including fever, prostaglandin synthesis (m, e.g., fibroblasts, muscle cells and endothelial cells), T-lymphocyte activation, and interleukin-2 production. The original members of the IL-1 superfamily are IL-1α, IL-1β, and the IL-1 Receptor Antagonist (IL-1Ra, IL-1RA, IL-1ra, IL-1Rα). IL-1α and IL-β are pro-inflammatory cytokines involved in immune defense against infection. The IL-1Rα competes for receptor binding with IL-1α and IL-1β, blocking their role in immune activation. Other members of the IL-1 superfamily include IL-18 (see Dinarello (1994) FASEB J. 8(15):1314-1325; Huising et al. (2004) Dev. Comp. Immunol. 28(5):395-413) and six additional genes with structural homology to IL-1α, IL-1β, or IL-1RA, named IL1F5, IL1F6, IL1F7, IL1F8, IL1F9, and IL1F10. In accordance, IL-1α, IL-1β, and IL-1RA have been renamed IL-1F1, IL-1F2, and IL-1F3, respectively (see Sims et al. (2001) Trends Immunol. 22(10):536-537; Dunn et al. (2001) Trends Immunol. 22(10):533-536). A further putative member of the IL-1 family has been described called IL-33 or IL-1F11, although this name is not officially accepted in the HGNC gene family nomenclature database.

Both IL-1α and IL-1β are produced by macrophages, monocytes, and dendritic cells. They form an important part of the inflammatory response of the body against infection. These cytokines increase the expression of adhesion factors on endothelial cells to enable transmigration of leukocytes to sites of infection and re-set the hypothalamus thermoregulatory center, leading to an increased body temperature which expresses itself as fever. IL-1 is therefore called an endogenous pyrogen. The increased body temperature helps the body's immune system to fight infection. IL-1 is also important in the regulation of hematopoiesis. IL-1β production in peripheral tissue has also been associated with hyperalgesia (increased sensitivity to pain) associated with fever (Morgan et al. (2004) Brain Res. 1022(1-2):96-100). IL-1 upregulates expression of cyclooxygenase-2 (COX-2) associated with pain. For the most part, IL-1α and IL-1β bind to the same cellular receptor. This receptor is composed of two related, but non-identical, subunits that transmit intracellular signals via a pathway that is shared in large part with certain other receptors. These include the Toll family of innate immune receptors and the IL-18 receptor. IL-1α and IL-1β also possess similar biological properties, including induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen.

cDNAs encoding IL-1α and IL-1β have been isolated and expressed; these cDNAs represent two different gene products, termed IL-1α (Lomedico et al. (1984) Nature 312:458) and IL-1β (Auron et al. (1984) Proc. Natl. Acad. Sci. USA 81:7909). Eight interleukin 1 family genes form a cytokine gene cluster on chromosome 2. IL-1β is the predominant form produced by human monocytes both at the mRNA and protein levels. The two forms of human IL-1 share only 26% amino acid homology. Despite their distinct polypeptide sequences, the two forms of IL-1 have structural similarities (Auron et al. (1985) J. Mol. Cell. Immunol. 2:169), in that the amino acid homology is confined to discrete regions of the IL-1 molecule.

IL-1α and IL-1β are produced as precursor peptides. In other words they are made as a long protein that is then processed to release a shorter, active molecule, which is called the mature protein. IL-1α is produced as a proprotein that is proteolytically processed by calpain and released in a mechanism that is still not well studied. Mature IL-1β, for example, is released from Pro-IL-1β following cleavage by a certain member of the caspase family of proteins, called caspase-1 or the interleukin-1 converting enzyme (ICE). The 3-dimensional structure of the mature forms of each member of the human IL-1 superfamily is composed of 12-14 β-strands producing a barrel-shaped protein.

IL-1α was originally termed "catabolin" because of its effect in increasing cartilage resorption, but also as "monocyte cell factor" (MCF) because of its stimulatory effect on collagenase and prostaglandin in synovial cells, and as "leukocyte endogenous factor" (LEM) having a stimulatory effect on acute phase reactions. IL-1α has a broad spectrum of biological activities, since IL-1α is synthesized by many different cells, such as monocytes, macrophages, fibroblasts, endothelial cells and lymphocytes, and many cells possess specific receptors for IL-1α. IL-1α stimulates thymocyte proliferation by inducing IL-2 release, B-cell maturation and proliferation, and fibroblast growth factor activity. IL-1α proteins were identified as endogenous pyrogens and are reported to stimulate the release of prostaglandin and collagenase from synovial cells. Thus, IL-1α also occupies a central position as the trigger for various disorders and symptoms of disorders. These disorders are often predominantly serious disorders for which there is little or no treatment. It has been suggested that the polymorphism of these genes is associated with rheumatoid arthritis and Alzheimer's disease. IL-1 in general has been implicated in many human diseases, including arthritis, pulmonary fibrosis, diseases of the central nervous system, diabetes mellitus, and certain cardiovascular diseases. The undesirable effects of IL-1α are described in, for example, Oppenheim et al. (1986) Immunol. Today 7:45-56, Durum et al. (1985) Ann. Rev. Immunol. 3:263-287 and Symons et al. (1989) Lymphokine Res. 8:365-372.

The initiation, maintenance, and progression of OA is mediated by a complex cascade of mechanical and biochemical pathways in which IL-1 plays a pivotal role. IL-1α and IL-1β are produced not only by monocytes, macrophages, and neutrophils, but by cells in joint tissues, such as chondrocytes, synovial fibroblasts, and osteoclasts (see, e.g., Dinarello et al. (2009) Ann. Rev. Immunol. 27: 519-550). In vitro, IL-1 can stimulate chondrocytes and synoviocytes to produce proteinases involved in cartilage destruction leading to OA (see, e.g., Dayer et al. (1977) Science 195: 181-183; Dayer et al. (1984) Biochem. Pharmacol. 33: 2893-2899; McGuire-Goldring et al. (1984) Arthritis Rheum. 27: 654-662), as well as inhibit synthesis of proteoglycan and collagen type II, the main components of the extracellular matrix (ECM) of normal hyaline cartilage (see, e.g., Goldring et al. (1987) J. Biol. Chem. 262: 16724-16729; Goldring et al. (1988) J. Clin. Investig. 82: 2026-2037). Preclinical and clinical studies have provided further evidence of IL-1 in the pathogenesis of OA. For example, intra-articular (ia) injection of IL-1 into animal knees resulted in leukocyte infiltration and cartilage loss (Pettiphar et al. (1986) Proc. Natl. Acad. Sci. USA 83: 8749-8753). In contrast, ia injection of IL-1 antagonist resulted in significant reduction in the progression of experimental OA (see, e.g., Pelletier et al. (1997) Arthritis Rheum. 40: 1012-1019; Caron et al. (1996) Arthritis Rheum. 39: 1535-1544); Fernandes et al. (1999) Am. J. Pathol. 154: 11590-11690); Zhang et al. (2006) Biochem. Biophys. Res. Commun 341: 202-208). In addition, IL-1 knockout (KO) mice were found to be resistant to surgically induced cartilage damage when compared to their wild-type counterparts (Glasson et al. (2009) Osteoarthritis Cartilage, 18: 572-580).

Both IL-1α and IL-1β are expressed in synovial membranes, cartilage, and synovial fluid of human OA patients (see, e.g., Farahat et al. (1993) Ann. Rheum. Dis. 52: 870-875). The IL-1 antagonist, Anakinra, which is an IL-1 receptor antagonist, and AMG-108, which is an IL-1 receptor monoclonal antibody, have demonstrated some efficacy in OA trials with respect to symptoms and chondroprotection ("Results from a Randomized Controlled Trial of AMG 108 (a fully human monoclonal antibody to IL-1R type 1) in Patients With Osteoarthritis of the Knee" Cohen et al., ACR 2007). Both of these proposed therapies await additional studies to demonstrate clear and robust clinical efficacy.

A need remains for new and effective methods and compositions for treating individuals afflicted with osteoarthritis.

SUMMARY OF THE INVENTION

The invention provides methods for treating osteoarthritis (OA) and for treating pain. Such methods comprise administering to an individual (human or other mammal) one or more binding proteins that bind IL-1α and IL-1β.

In an aspect of the invention, a method for treating osteoarthritis in an individual (human or other mammal) comprises the step of administering to the individual a binding protein that binds IL-1α in combination with (e.g., in a mixture, by successive administration, or by concurrent administration with) a binding protein that binds IL-1β or administering to the individual a binding protein that binds both IL-1α and IL-1β.

In an embodiment, a method for treating osteoarthritis in an individual comprises administering to the individual a binding protein that binds IL-1α, wherein the binding protein is an antibody to IL-1α, for example, a monoclonal antibody to IL-1α. In another embodiment, a method for treating osteoarthritis in an individual comprises administering to the individual a binding protein that binds IL-1β, wherein the binding protein is an antibody that binds IL-1β, for example, a monoclonal antibody that binds IL-1β.

In another aspect of the invention, a method of treating osteoarthritis in an individual (human or other mammal) comprises the step of administering to the individual a binding protein that binds both IL-1α and IL-1β. Preferably, the binding protein is a dual variable domain immunoglobulin binding protein (also referred herein as "DVD-Ig™" or "DVD-Ig" binding protein or molecule) that comprises at least one binding site that binds IL-1α and at least one binding site that binds IL-1β. More preferably, the DVD-Ig binding protein comprises two binding sites that bind IL-1α and two binding sites that bind IL-1β.

In another embodiment, a method according to the invention for treating osteoarthritis in an individual comprises administering to the individual a pharmaceutical composition comprising a binding protein that binds IL-1α, a binding protein that binds IL-1β, a combination of a binding protein that bind IL-1α and a binding protein that binds IL-1β, or a binding protein that binds both IL-1α and IL-1β; and a pharmaceutically acceptable carrier.

In an embodiment of the invention, a method for treating osteoarthritis comprises administering to an individual a crystallized binding protein that binds IL-1α and a crystallized binding protein that binds IL-1β, or a crystallized binding protein that binds both IL-1α and IL-1β. Such crystallized binding proteins useful in the invention include, but are not limited to, a crystallized antibody IL-1α, a crystallized antibody to IL-1β, and a crystallized DVD-Ig binding protein that binds both IL-1α and IL-1β.

Compositions useful in methods of the invention for treating osteoarthritis in an individual include a composition for the release of a crystallized binding protein that binds IL-1α, a crystallized binding protein that binds IL-1β, a combination of a crystallized binding protein that binds IL-1α and a crystallized binding protein that binds IL-1β, or a crystallized binding protein that binds both Il-1α and IL-1β.

In an embodiment, a composition useful in a method for treating osteoarthritis according to the invention comprises:

(a) a formulation, wherein said formulation comprises a crystallized binding protein that binds IL-1α, a crystallized binding protein that binds IL-1β, a combination of both a crystallized binding protein that binds IL-1α and a crystallized binding protein that binds IL-1β, or a crystallized binding protein that binds both Il-1α and IL-1β; and, optionally, an ingredient; and (b) at least one polymeric carrier.

In an embodiment, a composition described above comprises a combination of both a crystallized binding protein that binds IL-1α and a crystallized binding protein that binds IL-1β. In another embodiment, the crystallized binding protein that binds IL-1α is a crystallized antibody, for example, a crystallized monoclonal antibody that binds IL-1α and the crystallized binding protein that binds IL-1β is a crystallized antibody, for example, a monoclonal antibody that binds IL-1β.

In an embodiment, a composition described above comprises a crystallized binding protein that binds both Il-1α and IL-1β. In another embodiment, the crystallized binding protein is a crystallized dual variable domain (DVD-Ig) binding protein the binds both IL-1α and IL-1β-Ig.

In another embodiment, a method for treating osteoarthritis in an individual comprises administering to the individual a composition comprising a crystallized binding protein that binds IL-1α, a crystallized binding protein that binds IL-1β, a combination of both a crystallized binding protein that binds IL-1α and a crystallized binding protein that binds IL-1β, or a crystallized binding protein that binds both Il-1α and IL-1β; wherein said at least one polymeric carrier is a polymer selected from one or more of the group consisting of poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone), poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

In an embodiment, when the optional ingredient is present in a composition described above, the ingredient is selected from the group consisting of albumin, sucrose, trehalose, lactitol, gelatin, hydroxypropyl-β-cyclodextrin, methoxypolyethylene glycol and polyethylene glycol.

In an embodiment, a method for treating osteoarthritis described above further comprises administering to the individual a second agent, wherein the second agent provides an additional desirable property to the method or composition used in the method. Such a second agent can be one or more molecules in the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies of TNF, LT, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, an NSAID, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13, and TGFβ.

In another aspect of the invention, a method for treating osteoarthritis described herein comprises administering to an individual one or more binding proteins described herein or a composition described herein by at least one mode selected from parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In an aspect of the invention, a method for treating pain in an individual (human or other mammal) comprises the step of administering to the individual a binding protein that binds IL-1α in combination with (e.g., in a mixture, by successive administration, or by concurrent administration with) a binding protein that binds IL-1β or administering to the individual a binding protein that binds both IL-1α and IL-1β.

Methods and compositions according to the invention can be used to treat pain in an individual having any form of pain, including pain from cancer, neuropathic pain, muscle pain, joint pain, bone fracture pain, wound pain, pain from surgery, headache, migraine, as well as pain conditions such as allodynia (allodynic pain), hyperalgesia, and a combination of allodynia and hyperalgesia.

In an embodiment, a method for treating pain in an individual comprises administering to the individual a binding protein that binds IL-1α, wherein the binding protein is an antibody to IL-1α, for example, a monoclonal antibody to IL-1α. In another embodiment, a method for treating pain in an individual comprises administering to the individual a binding protein that binds IL-1β, wherein the binding protein is an antibody that binds IL-1β, for example, a monoclonal antibody that binds IL-1β.

In another aspect of the invention, a method of treating pain in an individual comprises the step of administering to the individual a binding protein that binds both IL-1α and IL-1β. Preferably, the binding protein is a dual variable domain immunoglobulin binding protein (also referred herein as "DVD-Ig™" or "DVD-Ig" binding protein or molecule) that comprises at least one binding site that binds IL-1α and at least one binding site that binds IL-1β. Preferably, the DVD-Ig binding protein comprises two binding sites that bind IL-1α and two binding sites that bind IL-1β.

In another embodiment, a method according to the invention for treating pain in an individual comprises administering to the individual a pharmaceutical composition comprising a binding protein that binds IL-1α, a binding protein that binds IL-1β, a combination of a binding protein that bind IL-1α and a binding protein that binds IL-1β, or a binding protein that binds both IL-1α and IL-1β; and a pharmaceutically acceptable carrier.

In an embodiment of the invention, a method for treating pain comprises administering to an individual a crystallized binding protein that binds IL-1α and a crystallized binding protein that binds IL-1β, or a crystallized binding protein that binds both IL-1α and IL-1β. Such crystallized binding proteins useful in the invention include, but are not limited to, a crystallized antibody IL-1α, a crystallized antibody to IL-1β, and a crystallized DVD-Ig binding protein that binds both IL-1α and IL-1β.

Compositions useful in methods of the invention for treating pain in an individual include a composition for the release of a crystallized binding protein that binds IL-1α, a crystallized binding protein that binds IL-1β, a combination of a crystallized binding protein that binds IL-1α and a crystallized binding protein that binds IL-1β, or a crystallized binding protein that binds both IL-1α and IL-1β.

In an embodiment, a composition useful in a method for treating pain according to the invention comprises:

(a) a formulation, wherein said formulation comprises a crystallized binding protein that binds IL-1α, a crystallized binding protein that binds IL-1β, a combination of both a crystallized binding protein that binds IL-1α and a crystallized binding protein that binds IL-1β, or a crystallized binding protein that binds both Il-1α and IL-1β; and, optionally, an ingredient; and (b) at least one polymeric carrier.

In an embodiment, a composition described above comprises a combination of both a crystallized binding protein that binds IL-1α and a crystallized binding protein that binds IL-1β. In another embodiment, the crystallized binding protein that binds IL-1α is a crystallized antibody, for example, a crystallized monoclonal antibody, that binds IL-1α and the crystallized binding protein that binds IL-1β is a crystallized antibody, for example, a monoclonal antibody that binds IL-1β.

In an embodiment, a composition described above comprises a crystallized binding protein that binds both Il-1α and IL-1β. In another embodiment, the crystallized binding protein is a crystallized dual variable domain (DVD-Ig) binding protein the binds both IL-1α and IL-1β-Ig.

In another embodiment, a method for treating pain in an individual comprises administering to the individual a composition comprising a crystallized binding protein that binds IL-1α, a crystallized binding protein that binds IL-1β, a combination of both a crystallized binding protein that binds IL-1α and a crystallized binding protein that binds IL-1β, or a crystallized binding protein that binds both Il-1α and IL-1β; wherein said at least one polymeric carrier is a polymer selected from one or more of the group consisting of poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

In an embodiment, when the optional ingredient is present in a composition described above, the ingredient is selected from the group consisting of albumin, sucrose, trehalose, lactitol, gelatin, hydroxypropyl-β-cyclodextrin, methoxypolyethylene glycol and polyethylene glycol.

In an embodiment, a method for treating pain described above further comprises administering to the individual a second agent, wherein the second agent provides an additional desirable property to the method or composition used in the method. Such a second agent can be one or more molecules in the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies of TNF, LT, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, an NSAID, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13, and TGFβ.

In another aspect of the invention, a method for treating pain as described herein comprises administering to an individual one or more binding proteins described herein or a composition described herein by at least one mode selected from parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In another embodiment, the invention provides a method of treating pain in an individual suffering from a disease or disorder associated with IL-1 expression. Such IL-1 expression in the individual can result in increased IL-1 levels in the plasma and/or local tissue of the individual.

In an embodiment, the methods and compositions described herein are used to treat pain in an individual suffering from a disease or disorder selected from the group comprising osteoarthritis, rheumatoid arthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis, scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I, polyglandular deficiency type II (Schmidt's syndrome), adult (acute) respiratory distress syndrome, alopecia, alopecia areata, seronegative arthropathy, arthropathy, Reiter's disease, psoriatic arthropathy, ulcerative colitic arthropathy, enteropathic synovitis, *Chlamydia*-associated arthropathy, *Yersinia*-associated arthropathy, *Salmonella*-associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free disease, chronic mucocutaneous candidiasis, giant cell arteritis, primary sclerosing hepatitis, cryptogenic autoimmune hepatitis, acquired immunodeficiency syndrome, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, cholestasis, idiosyncratic liver disease, drug-induced hepatitis, non-alcoholic steatohepatitis, allergy, group B streptococci (GBS) infection, mental disorders (e.g., depression and schizophrenia), Th2 Type and Th1 Type mediated diseases, acute and chronic pain (different forms of pain), cancers such as lung, breast, stomach, bladder, colon, pancreas, ovarian, prostate and rectal cancer and hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, atrial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis A, His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic migraine headache, idiopathic migraine headache, mitochondrial multisystem disorder, mixed connective tissue disease, monoclonal gammopathy, multiple myeloma, multiple systems degenerations (Menzel, Dejerine-Thomas, Shy-Drager, and Machado-Joseph), myasthenia gravis, *mycobacterium avium intracellulare*, *mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-Hodgkin's lymphoma, occlusion of the abdominal aorta and its branches, occlusive arterial disorders, OKT3® therapy, orchitis/epididymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon, Raynaud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangiitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia areata, anaphylaxis, anti-phospholipid antibody syndrome, aplastic anemia, arteriosclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, childhood onset psychiatric disorder, chronic obstructive pulmonary disease (COPD), dacryocystitis, dermatomyositis, diabetic retinopathy, disk herniation, disk prolapse, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier disease, Landry's paralysis, Langerhan's cell histiocytosis, livedo reticularis, macular degeneration, microscopic polyangiitis, Morbus Bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, ovarian cancer, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor-necrosis factor receptor type 1 (TNFR)-associated periodic syndrome), type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, and wound healing.

In an embodiment, the methods and compositions described herein are used to treat pain in an individual suffering The method for treating pain in an individual according to claim 16, wherein the individual is suffering from a disease selected from the group consisting of a primary cancer, a metastatic cancer, breast cancer, colon cancer, rectal cancer, lung cancer, oropharynx cancer, hypopharynx cancer, esophagus cancer, stomach cancer, pancreatic cancer, liver cancer, gallbladder cancer, bile duct cancer, small intestine cancer, colon cancer, urinary tract cancer, kidney cancer, bladder cancer, urothelium cancer, female genital tract cancer, cervical cancer, uterine cancer, ovarian cancer, choriocarcinoma, gestational trophoblastic disease, male genital tract cancer, prostate cancer, seminal vesicle cancer, testicular cancer, germ cell tumor, endocrine gland cancer, thyroid cancer, adrenal cancer, pituitary gland cancer, skin cancer, hemangioma, melanoma, sarcoma, bone cancer, soft tissue cancer, Kaposi's sarcoma, tumor of the brain, nerve cancer, eye cancer, cancer of the meninges, astrocytoma, glioma, glioblastoma, retinoblastoma, neuroma, neuroblastoma, Schwannoma, meningioma, a solid tumor arising from hematopoietic malignancy, leukemia, Hodgkin's lymphoma, and non-Hodgkin's lymphoma.

("anti-IL-1α mAb (6 mg/kg)"), with anti-IL-1β monoclonal antibody (6 mg/kg) ("anti-IL-1β mAb (6 mg/kg)"), or with a combination of anti-IL-1α monoclonal antibody (6 mg/kg) and anti-IL-1β monoclonal antibody (6 mg/kg) ("anti-IL-1α mAb (6 mg/kg)+anti-IL-1β mAb (6 mg/kg)") administered intraperitoneally (ip) twice per week for four weeks. Animals were tested for allodynia on day 28. "Contralateral" bar graph provides paw withdrawal threshold of a representative non-surgical (contra lateral) limb. The ipsilateral (surgical) limb of animals in groups treated with vehicle was allodynic (painful) compared to the contra lateral (non-surgical) limb or compared to animals that had undergone sham surgery ("Sham"). See Example 5.

Figure 13:
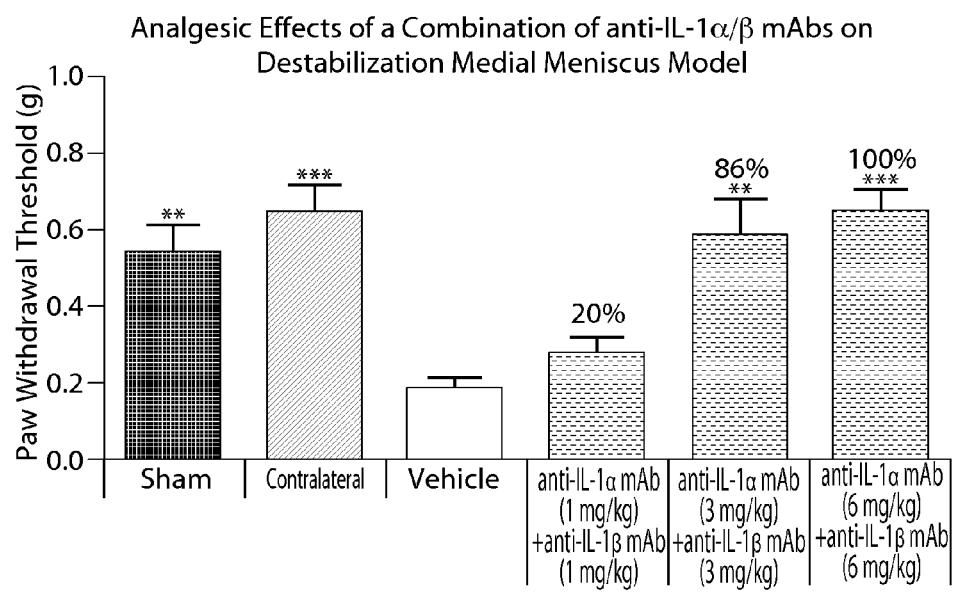

FIG. 13 shows bar graphs of paw withdrawal threshold (grams, "g") in DMM mice treated with PBS vehicle only ("Vehicle") or with a combination of anti-IL-1α monoclonal antibody and anti-IL-1β monoclonal antibody, both administered intraperitoneally (ip) every four days for four weeks at 1 mg/kg ("anti-IL-1α mAb (1 mg/kg)+anti-IL-1β mAb (1 mg/kg)"), at 3 mg/kg ("anti-IL-1α mAb (3 mg/kg)+anti-IL-1β mAb (3 mg/kg)"), or at 6 mg/kg ("anti-IL-1α mAb (6 mg/kg)+anti-IL-1β mAb (6 mg/kg)"). Animals were tested on day 28. The ipsilateral (surgical) limb of animals in groups treated with PBS vehicle only was allodynic (painful) compared to the contra lateral (non-surgical) limb ("Contralateral") or compared to animals that had undergone sham surgery ("Sham"). The results show that treatment with a combination of anti-IL-1α monoclonal antibody and anti-IL-1β monoclonal antibody prevents allodynia development in DMM mice in a dose related manner. See Example 6.

Figure 14:
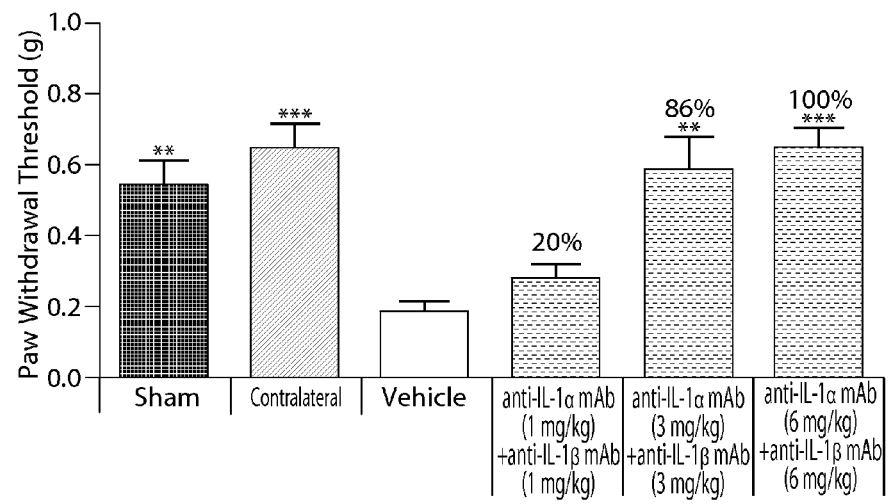

FIG. 14 shows bar graphs of paw withdrawal threshold (grams, "g") when DMM mice with established osteoarthritis and mechanical allodynia were treated at day 27 with a combination of anti-IL-1α monoclonal antibody and anti-IL-1β monoclonal antibody, both administered intraperitoneally (ip) at 1 mg/kg ("anti-IL-1α mAb (1 mg/kg)+anti-IL-1β mAb (1 mg/kg)"), at 3 mg/kg ("anti-IL-1α mAb (3 mg/kg)+anti-IL-1β mAb (3 mg/kg)"), or at 6 mg/kg ("anti-IL-1α mAb (6 mg/kg)+anti-IL-1β mAb (6 mg/kg)") at 24 hours prior to testing for allodynia on day 28. The ipsilateral (surgical) limb of animals in groups treated with vehicle ("Vehicle") was allodynic (painful) compared to the contra lateral (non-surgical) limb ("Contralateral") or compared to animals that had undergone sham surgery ("Sham"). The results show that treatment with a combination of anti-IL-1α monoclonal antibody and anti-IL-1β monoclonal antibody reverses established allodynia in DMM mice with established disease in a dose related manner. See Example 7.

Figure 15A:
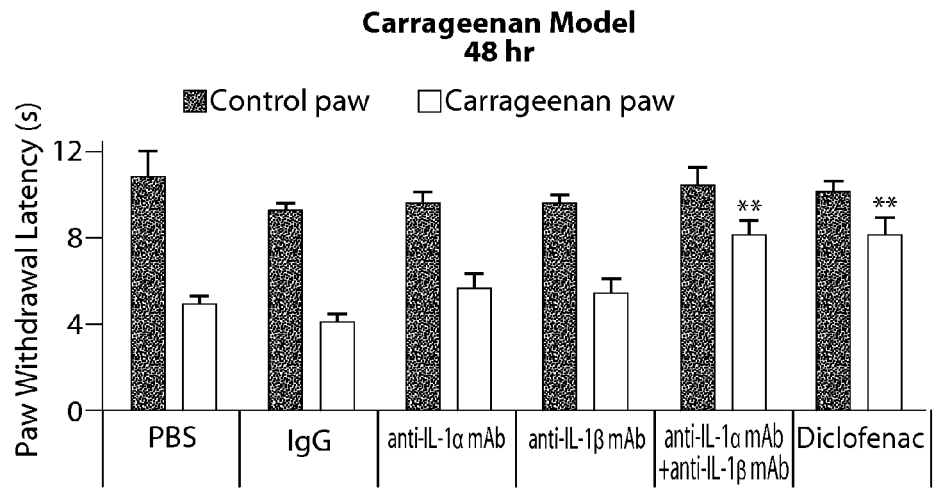
Figure 15B:
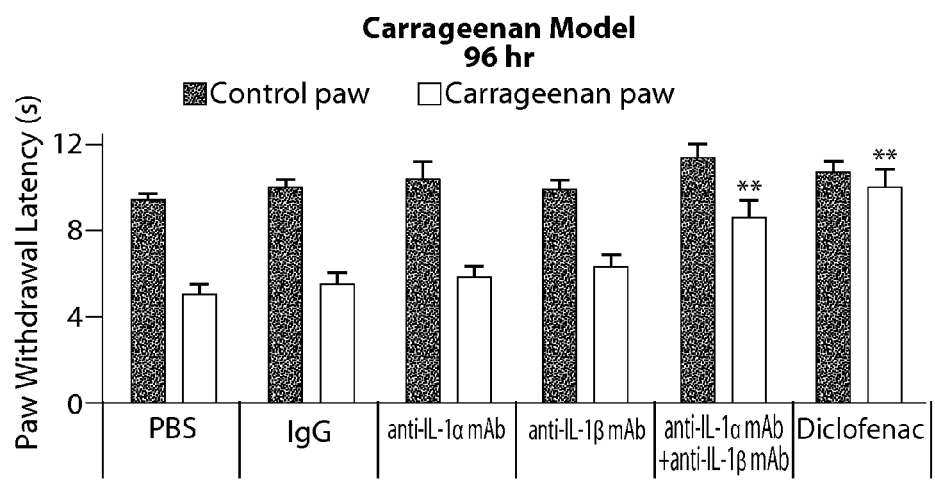

FIG. 15 shows bar graphs of paw withdrawal latency (seconds, "s") in animals in a mouse carrageenan-induced inflammatory pain (hyperalgesia) model. At 30 hours after intraplantar carrageenan injection, mice were treated with anti-IL-1α monoclonal antibody alone (900 μg) ("anti-IL-1α mAb"), anti-IL-1β monoclonal antibody alone (900 μg) ("anti-IL-1β mAb"), a combination of anti-IL-1α monoclonal antibody (900 μg) and anti-IL-1β monoclonal antibody (900 μg) ("anti-IL-1α mAb+anti-IL-1β mAb"), PBS vehicle ("PBS"), or IgG isotype control ("IgG"). Another group was administered a dose (30 mg/kg) of diclofenac (non-steroidal anti-inflammatory analgesic control) at 47 and 95 hours after intraplantar administration of carrageenan. Thermal hyperalgesia testing using radiant heat stimulus was performed 48 hours (FIG. 15A) and 96 hours (FIG. 15B) after intraplantar administration of carrageenan. Filled bars show paw withdrawal latency for control paw (no carrageenan). Open bars show paw withdrawal latency for paw administered carrageenan. See Example 8.

Figure 16A:
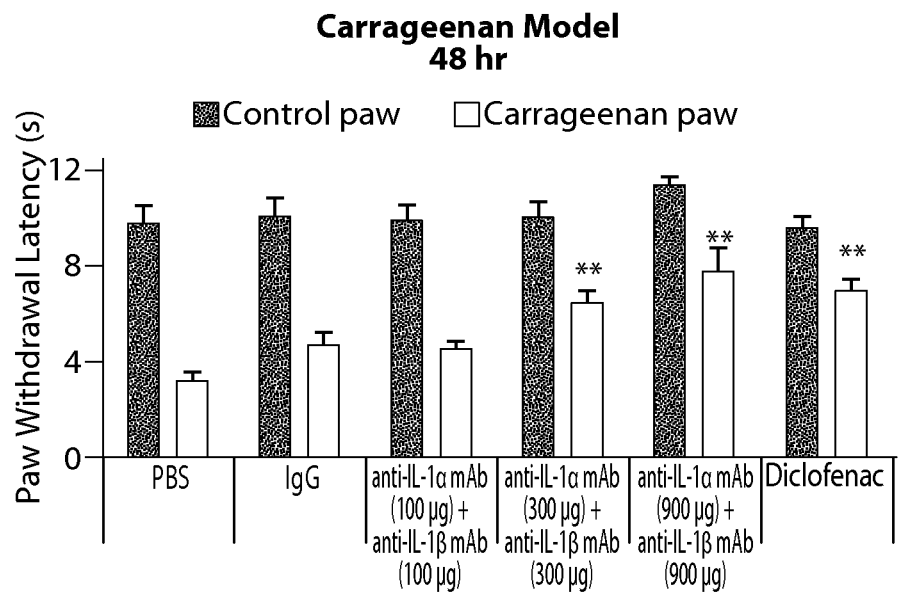
Figure 16B:
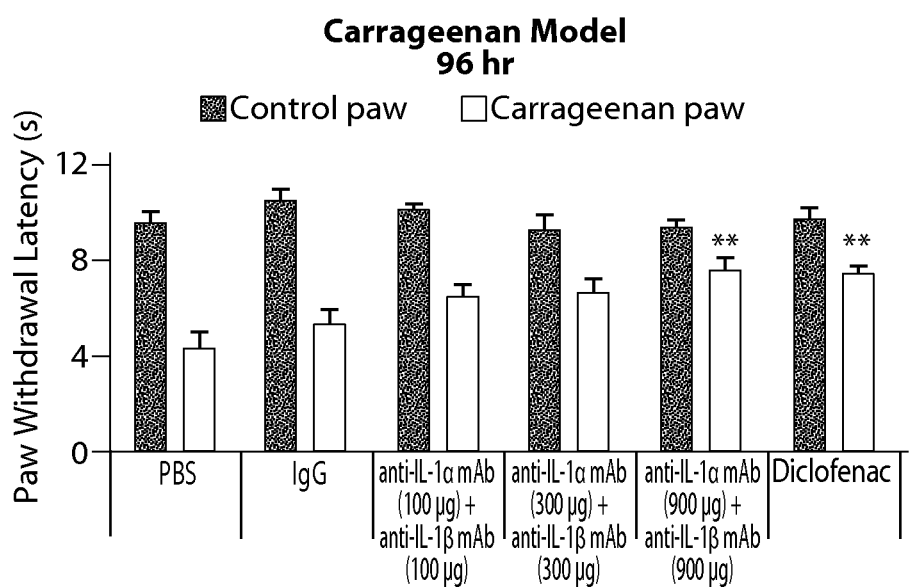

FIG. 16 shows bar graphs of paw withdrawal latency (seconds, "s") in animals in a mouse carrageenan-induced inflammatory pain (hyperalgesia) model in mice. At 30 hours after intraplantar carrageenan injection, mice were treated with vehicle ("PBS"), IgG isotype control ("IgG"), or one of three doses of a combination of anti-IL-1α monoclonal antibody and anti-IL-1β monoclonal antibody, wherein each monoclonal antibody was administered at 100 μg ("anti-IL-1α mAb (100 μg)+anti-IL-1β mAb (100 μg)"), at 300 μg ("anti-IL-1α mAb (300 μg)+anti-IL-1β mAb (300 μg)"), or at 900 μg ("anti-IL-1α mAb (900 μg)+anti-IL-1β mAb (900 μg)"). Another group was administered a dose (30 mg/kg) of diclofenac (non-steroidal anti-inflammatory analgesic positive control) at 47 and 95 hours after intraplantar administration of carrageenan. Thermal hyperalgesia testing using radiant heat stimulus was performed at 48 hours (FIG. 16A) and 96 hours (FIG. 16B) after intraplantar administration of carrageenan. Filled bars show paw withdrawal latency for control paw (no carrageenan). Open bars show paw withdrawal latency for paw administered carrageenan. See Example 9.

Figure 17A:
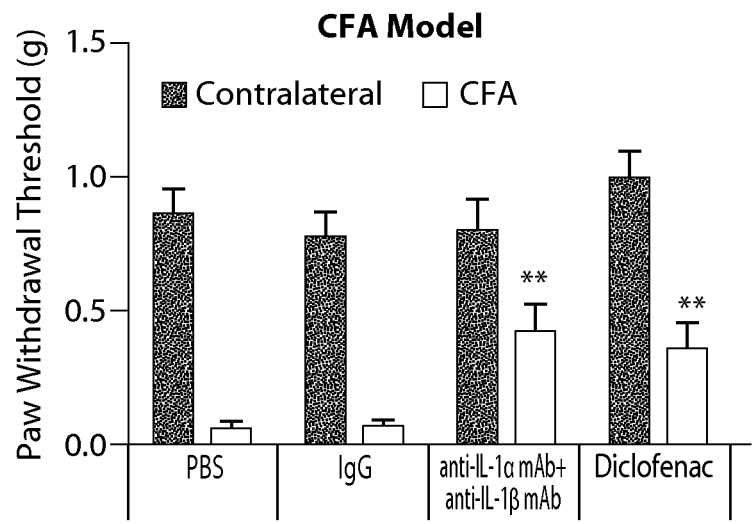
Figure 17B:
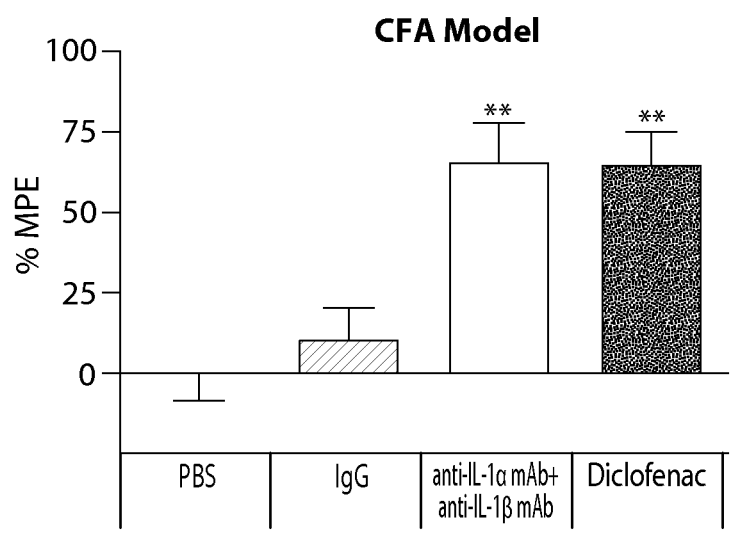

FIG. 17 shows results of testing anti-IL-1α and anti-IL-1β monoclonal antibody combination therapy in a CFA ("Complete Freund's Adjuvant) inflammatory pain model in mice. At 30 hours after intraplantar CFA injection, mice were treated with a combination of anti-IL-1α monoclonal antibody (900 μg) and anti-IL-1β monoclonal antibody (900 μg), with PBS vehicle ("PBS"), or with IgG isotype control ("IgG"). Another group was administered a dose (30 mg/kg) of diclofenac (non-steroidal, anti-inflammatory analgesic positive control) at 47 hours after intraplantar administration of CFA. Mechanical allodynia testing of animals using a von Frey monofilament was performed at 48 hours after CFA administration. FIG. 17A shows bar graphs of paw withdrawal threshold (grams, "g"). Filled bars show paw withdrawal threshold for contra lateral (no CFA) control paws. Open bars show paw withdrawal threshold for paw administered CFA in animals of treatment groups. FIG. 17B shows bar graphs for magnitude of efficacy (% MPE) for animals of treatment groups. See Example 10.

Figure 18A:
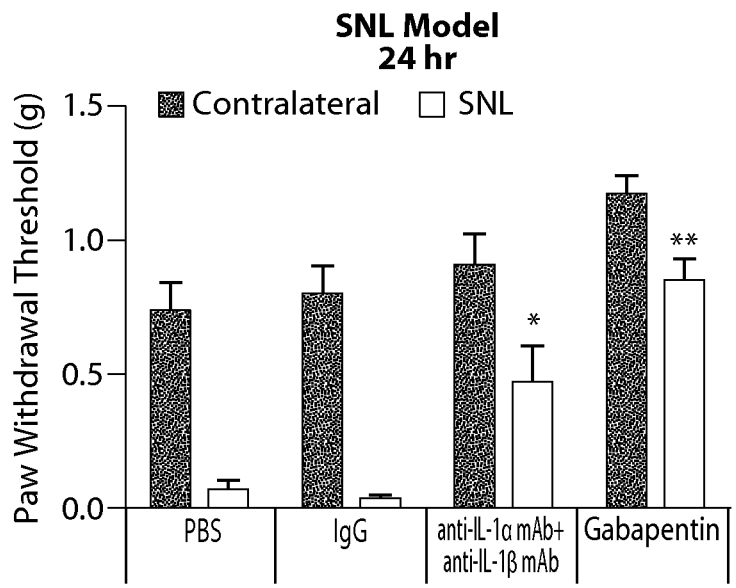
Figure 18B:
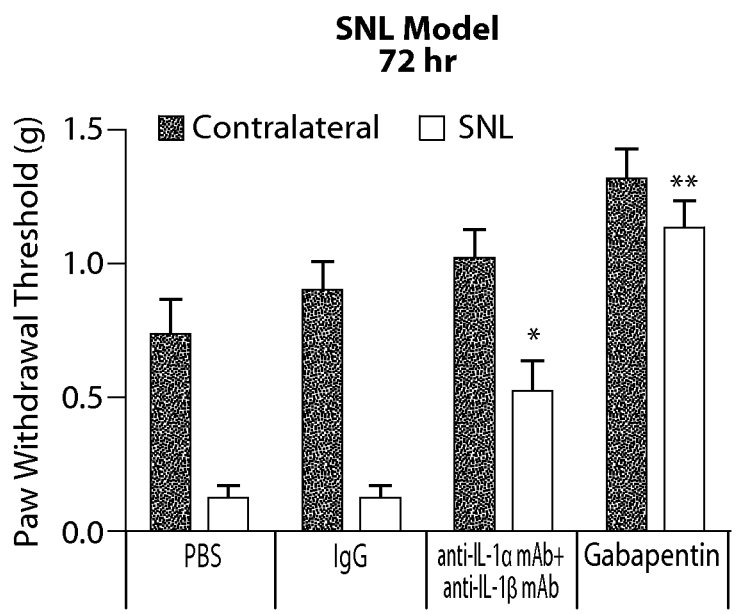

FIG. 18 shows bar graphs of paw withdrawal threshold (grams, "g") in animals of an L5/L6 spinal nerve ligation (SNL) mouse model of neuropathic pain. Animals were treated at day 6 after SNL surgery with a combination of anti-IL-1α monoclonal antibody (900 μg) and anti-IL-1β monoclonal antibody (900 μg) ("anti-IL-1α mAb+anti-IL-1β mAb"), PBS vehicle ("PBS"), or IgG isotype control ("IgG"). Mechanical allodynia testing of animals using a von Frey monofilament was performed at 24 hours (FIG. 18A) and 72 hours (FIG. 18B) after SNL surgery. Another group was treated with gabapentin (100 mg/kg, "Gabapentin") at 1 hour prior to testing as a positive control. See Example 11.

Figure 19:
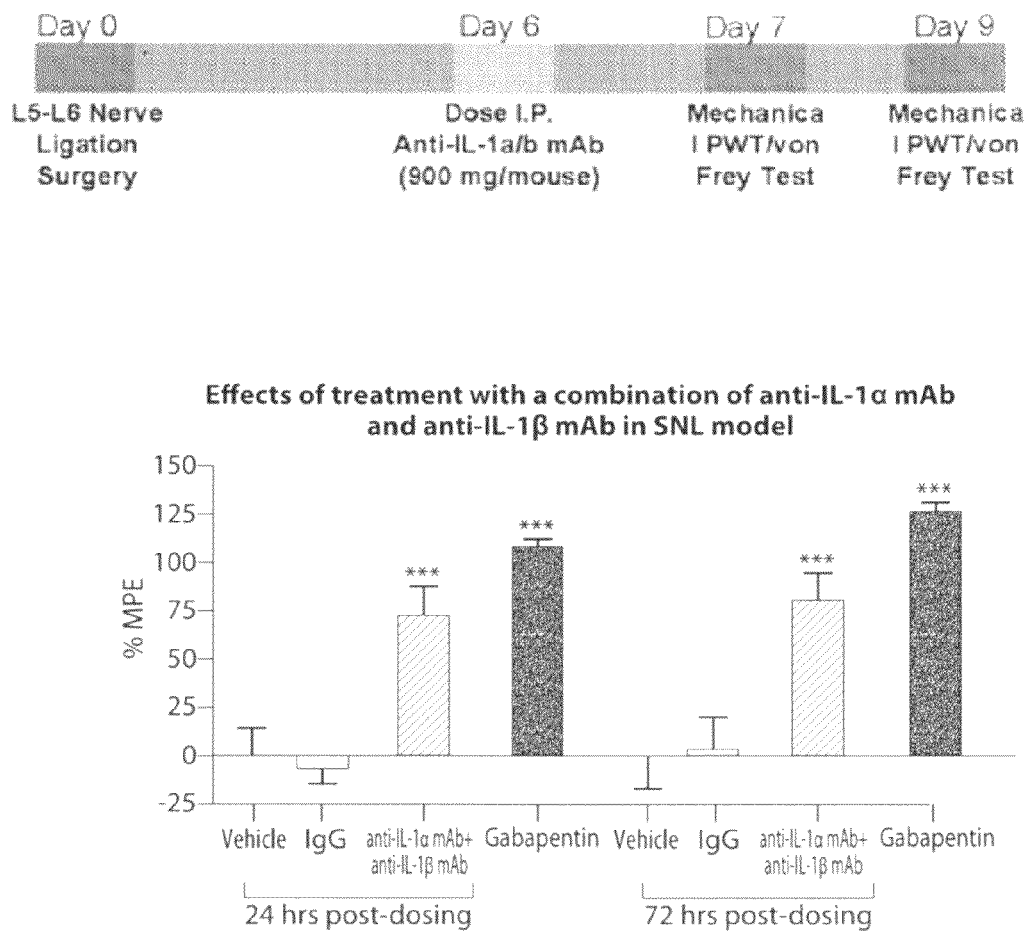

FIG. 19 shows bar graphs for magnitude of efficacy (% MPE) for animal treatment groups at 24 and 72 hours as described for FIG. 18. "Vehicle" indicates SNL animals treated with PBS vehicle treated. "IgG" indicates SNL animals treated with IgG isotype control. "IL-1αβ" indicates animals treated with combination anti-IL-1α monoclonal antibody (900 μg) and anti-IL-1β monoclonal antibody. See Example 11.

DETAILED DESCRIPTION OF THE INVENTION

The invention is based on the discovery that blocking the function of interleukin-1 (IL-1) can be an effective means to treat osteoarthritis (OA) in an individual (human or other mammal). According to the invention, blocking IL-1 function for treating OA may be achieved by administering to an individual one or more proteins that bind IL-1α and IL-1β. Such a "dual-specific" therapy can be achieved by administering to an OA patient a binding protein (e.g., an antibody) that binds IL-1α and a binding protein (e.g., an antibody) that binds IL-1β or by administering a multivalent and multispecific binding protein that binds both IL-1α and IL-1β. Such a multivalent and multispecific binding protein useful in the invention includes a dual variable domain immunoglobulin binding protein (also referred herein as "DVD-Ig™" or "DVD-Ig" binding protein or molecule). See, e.g., PCT Publication No. WO 2007/024715 and Wu et al. (2007) Nature Biotech. 25(11): 1290-1297. Whether a particular combination of IL-1α and IL-1β binding proteins or a specific DVD-Ig molecule that binds both IL-1α and IL-1β will be useful for the treatment of OA can be assessed using an animal model of OA, such as the joint instability model (JIM) of OA or the destabilization of medial meniscus (DMM) model of OA (Glasson et al. (2007) Osteoarthrit. Cart. 15(9):1061-9).

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of the term "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, protein and nucleic acid chemistry, and nucleic acid hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" means any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" means a protein or polypeptide that by virtue of its origin or source of derivation is not associated with naturally associated components that accompany it in its native state, is substantially free of other proteins from the same species, is expressed by a cell from a different species, or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" means the process of rendering a chemical species such as a polypeptide substantially free of naturally associated components by isolation, e.g., using protein purification techniques well known in the art.

The term "human IL-1α" (also abbreviated herein as "hIL-1α" or "IL-1α"), includes a pleiotropic cytokine involved in various immune responses, inflammatory processes, and hematopoiesis. For example, IL-1α includes the human cytokine produced by activated macrophages; it stimulates thymocyte proliferation by inducing IL-2 release, B-cell maturation and proliferation, and fibroblast growth factor activity. The term "human IL-1α" is intended to include recombinant human IL-1α ("rh IL-1α") that can be prepared by standard recombinant expression methods.

The term "human IL-1β" (also abbreviated herein as "hIL-1β", or "IL-1β") includes a pleiotropic cytokine involved in various immune responses, inflammatory processes, and hematopoiesis. The term human "IL-1β" includes recombinant human IL-1β ("rh IL-1β") that can be prepared by standard recombinant expression methods.

The amino acid sequences of human IL-1α and IL-1β are shown in Table 1.

TABLE 1

Sequences of Human IL-1α and IL-1β

| Protein | Sequence Identifier | Sequence 12345678901234567890123456789 0 |
|---|---|---|
| Human pro IL-1α | SEQ ID NO: 1 | MAKVPDMFEDLKNCYSENEEDSSSIDHLSL NQKSFYHVSYGPLHEGCMDQSVSLSISETS KTSKLTFKESMVVVATNGKVLKKRRLSLSQ SITDDDLEAIANDSEEEIIKPRSAPFSFLS NVKYNFMRIIKYEFILNDALNQSIIRANDQ YLTAAALHNLDEAVKFDMGAYKSSKDDAKI TVILRISKTQLYVTAQDEDQPVLLKEMPEI PKTITGSETNLLFFWETHGTKNYFTSVAHP NLFIATKQDYWVCLAGGPPSITDFQILENQ A |
| Human mature IL-1α | Residues 113-271 of SEQ ID NO: 1 | SAPFSFLSNVKYNFMRIIKYEFILNDALNQ SIIRANDQYLTAAALHNLDEAVKFDMGAYK SSKDDAKITVILRISKTQLYVTAQDEDQPV LLKEMPEIPKTITGSETNLLFFWETHGTKN YFTSVAHPNLFIATKQDYWVCLAGGPPSIT DFQILENQA |
| Human mature IL-1β | SEQ ID NO: 2 | APVRSLNCTLRDSQQKSLVMSGPYELKALH LQGQDMEQQVVFSMSFVQGEESNDKIPVAL GLKEKNLYLSCVLKDDKPTLQLESVDPKNY PKKKMEKRFVFNKIEINNKLEFESAQFPNW YISTSQAENMPVFLGGTKGGQDITDFTMQF VSS |

The term "biological activity" refers to all inherent biological properties of the cytokine. Biological properties of IL-1α and IL-1β include, but are not limited to, binding to an IL-1 receptor.

"Biological activity" refers to all inherent biological properties of IL-1α. Biological properties of IL-1α include, but are not limited to, binding to the IL-1α receptor; stimulating thymocyte proliferation by inducing IL-2 release, B-cell maturation and proliferation, and fibroblast growth factor activity.

The terms "specific binding" or "specifically binding", in reference to the interaction of an antibody, a protein, or a peptide with a second chemical species, mean that the interaction is dependent upon the presence of a particular structure (e.g., an antigenic determinant or epitope) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", broadly refers to any immunoglobulin (Ig) molecule comprised of four polypeptide chains, two heavy (H) chains and two light (L) chains, or any functional fragment, mutant, variant, or derivative thereof, that retains the essential epitope binding features of an Ig molecule. Such mutant, variant, or derivative antibody formats are known in the art, nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The term "antigen-binding portion" of an antibody refers to one or more fragments of an antibody that retain the ability to specifically bind to an antigen (e.g., hIL-1α). The antigen-binding function of an antibody can be performed by fragments of a full-length antibody. Such antibody embodiments may also have bispecific, dual specific, or multi-specific formats, specifically binding to two or more different antigens. Examples of binding fragments encompassed within the term "antigen-binding portion" of an antibody include (i) an Fab fragment, which is a monovalent fragment consisting of the VL, VH, CL, and CH1 domains; (ii) an F(ab')$_2$ fragment, which is a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al. (1989) Nature 341:544-546, PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies (scFvs) are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al. (1993) Proc. Natl. Acad. Sci. USA 90:6444-6448; Poljak et al. (1994) Structure 2:1121-1123). Such antibody binding portions are known in the art (Kontermann and Dübel eds., Antibody Engineering (Springer-Verlag, New York, 2001) (ISBN 3-540-41354-5)).

The term "antibody construct" refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see, e.g., Holliger et al. (1993) Proc. Natl. Acad. Sci. USA 90:6444-6448; Poljak et al. (1994) Structure 2:1121-1123). An immunoglobulin constant domain refers to a heavy or light chain constant domain. Human IgG heavy chain (gamma) and light chain (kappa and lambda) constant domain amino acid sequences are known in the art and represented in Table 2.

TABLE 2

Sequences of Human IgG Heavy and Light Chain Constant Domains

| Protein | Sequence Identifier | Sequence 123456789012345678901234567890 |
|---|---|---|
| Ig gamma-1 constant region | SEQ ID NO: 3 | ASTKGPSVFFLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig gamma-1 constant region mutant | SEQ ID NO: 4 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig Kappa constant region | SEQ ID NO: 5 | TVAAPSVFIFPPSDEQLKSGTASVVCLLNN FYPREAKVQWKVDNALQSGNSQESVTEQDS KDSTYSLSSTLTLSKADYEKHKVYACEVTH QGLSSPVTKSFNRGEC |
| Ig Lambda constant region | SEQ ID NO: 6 | QPKAAPSVTLFPPSSEELQANKATLVCLIS DFYPGAVTVAWKADSSPVKAGVETTTPSKQ SNNKYAASSYLSLTPEQWKSHRSYSCQVTH EGSTVEKTVAPTECS |

Still further, an antibody or antigen-binding portion thereof may be part of a larger immunoadhesion molecule, formed by covalent or noncovalent association of the antibody, or antigen binding portion thereof, with one or more other proteins or peptides. Examples of such immunoadhesion molecules include use of the streptavidin core region to make a tetrameric scFv molecule (Kipriyanov, S. et al. (1995) Human Antibod. Hybridomas 6:93-101) and use of a cysteine residue, a marker peptide and a C-terminal polyhistidine tag to make bivalent and biotinylated scFv molecules (Kipriyanov, S. et al. (1994) Mol. Immunol. 31:1047-1058). Antigen binding portions of antibodies, such as Fab and F(ab')$_2$ fragments, can be prepared from whole antibodies using conventional techniques, such as papain or pepsin digestion, respectively, of whole antibodies. Moreover, antibodies, antigen binding portions thereof, and immunoadhesion molecules can be obtained using standard recombinant DNA techniques, as described herein.

An "isolated antibody" refers to an antibody that is substantially free of other antibodies having different antigenic specificities (e.g., an isolated antibody that specifically binds hIL-1α is substantially free of antibodies that specifically bind antigens other than hIL-1α). An isolated antibody that specifically binds hIL-1α may, however, have cross-reactivity to other antigens, such as IL-1α molecules from other species. Moreover, an isolated antibody may be substantially free of other cellular material and/or chemicals.

The term "human antibody" includes antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom, H. (1997) Trends Biotechnol. 15: 62-70; Azzazy and Highsmith (2002) Clin. Biochem. 35: 425-445; Gavilondo and Larrick (2000) BioTechniques 29:128-145; Hoogenboom and Chames (2000) Immunol. Today 21: 371-378), antibodies isolated from an animal (e.g., a mouse) that is transgenic for human immunoglobulin genes (see, e.g., Taylor et al. (1992) Nucl. Acids Res. 20: 6287-6295; Kellermann and Green (2002) Curr. Opin. Biotechnol. 13: 593-597; Little et al. (2000) Immunol. Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable region sequences from one species and constant region sequences from another species, such as antibodies having murine heavy and light chain variable regions linked to human constant regions.

The term "CDR-grafted antibody" refers to antibodies that comprise heavy and light chain variable region sequences from one species but in which the sequences of one or more of the CDR regions of VH and/or VL regions are replaced with CDR sequences of another species, such as antibodies that have human heavy and light chain variable regions in which one or more of the human CDRs (e.g., CDR3) has been replaced with murine CDR sequences, for example, as obtained from a murine monoclonal antibody to human IL-1α.

As used herein, the term "CDR" refers to the complementarity determining region within antibody variable sequences. There are three CDRs in each of the variable regions of the heavy chain and the light chain, which are designated CDR1, CDR2, and CDR3, for each of the variable regions. The term "CDR set" as used herein refers to a group of three CDRs that occur in a single variable region (i.e., VH or VL) of an antigen binding site. The exact boundaries of these CDRs have been defined differently according to different systems. The system described by Kabat (Kabat et al. (1987, 1991) *Sequences of Proteins of Immunological Interest* (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) J. Mol. Biol. 196: 901-917 and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2, and L3 or H1, H2, and H3, where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (1995) FASEB J. 9: 133-139 and MacCallum (1996) J. Mol. Biol. 262(5): 732-745). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The terms "Kabat numbering", "Kabat definition" and "Kabat labeling" are used interchangeably herein. These terms refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad. Sci. 190: 382-391 and Kabat, E. et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains," In Kontermann and Dübel, eds., Antibody Engineering (Springer-Verlag, Berlin, 2001), chapter 31, pages 432-433. A useful method of determining the amino acid sequences of Kabat CDRs within the amino acid sequences of variable heavy (VH) and variable light (VL) regions is provided below:

To identify a CDR-L1 amino acid sequence:
 Starts approximately 24 amino acid residues from the amino terminus of the VL region;
 Residue before the CDR-L1 sequence is always cysteine (C);
 Residue after the CDR-L1 sequence is always a tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L);
 Length is typically 10 to 17 amino acid residues.
To identify a CDR-L2 amino acid sequence:
 Starts always 16 residues after the end of CDR-L1;
 Residues before the CDR-L2 sequence are generally Ile-Tyr (I-Y), but also Val-Tyr (V-Y), Ile-Lys (I-K), and Ile-Phe (I-F);
 Length is always 7 amino acid residues.
To identify a CDR-L3 amino acid sequence:
 Starts always 33 amino acids after the end of CDR-L2;
 Residue before the CDR-L3 amino acid sequence is always a cysteine (C);
 Residues after the CDR-L3 sequence are always Phe-Gly-X-Gly (F-G-X-G) (SEQ ID NO:7), where X is any amino acid;
 Length is typically 7 to 11 amino acid residues.
To identify a CDR-H1 amino acid sequence:
 Starts approximately 31 amino acid residues from amino terminus of VH region and always 9 residues after a cysteine (C);
 Residues before the CDR-H1 sequence are always Cys-X-X-X-X-X-X-X-X (SEQ ID NO:151), where X is any amino acid;
 Residue after CDR-H1 sequence is always a Trp (W), typically Trp-Val (W-V), but also Trp-Ile (W-I), and Trp-Ala (W-A);
 Length is typically 5 to 7 amino acid residues.
To identify a CDR-H2 amino acid sequence:
 Starts always 15 amino acid residues after the end of CDR-H1;
 Residues before CDR-H2 sequence are typically Leu-Glu-Trp-Ile-Gly (L-E-W-I-G) (SEQ ID NO:8), but other variations also;
 Residues after CDR-H2 sequence are Lys/Arg-Leu/Ile/Val/Phe/Thr/Ala-Thr/Ser/Ile/Ala (K/R-L/I/V/F/T/A-T/S/I/A);
 Length is typically 16 to 19 amino acid residues.
To identify a CDR-H3 amino acid sequence:
 Starts always 33 amino acid residues after the end of CDR-H2 and always 3 after a cysteine (C)';
 Residues before the CDR-H3 sequence are always Cys-X-X (C-X-X), where X is any amino acid, typically Cys-Ala-Arg (C-A-R);
 Residues after the CDR-H3 sequence are always Trp-Gly-X-Gly (W-G-X-G) (SEQ ID NO:9), where X is any amino acid;
 Length is typically 3 to 25 amino acid residues.

As used herein, the terms "acceptor" and "acceptor antibody" refer to the antibody or nucleic acid sequence providing or encoding at least 80%, at least 85%, at least 90%, at least 95%, at least 98%, or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "canonical" residue refers to a residue in a CDR or framework that defines a particular canonical CDR structure as defined by Chothia et al. (1987) J. Mol. Biol. 196:901-917 and Chothia et al. (1992) J. Mol. Biol. 227:799-817). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In one embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

Heavy Chain Acceptor Sequences

| SEQ ID No. | Protein region | Sequence |
|---|---|---|
| 10 | VH2-70/JH6 FR1 | EVTLRESGPALVKPTQTLTLTCTFSGFSLS |
| 11 | VH2-70/JH6 FR2 | WIRQPPGKALEWLA |
| 12 | VH2-70/JH6 FR3 | RLTISKDTSKNQVVLTMTNMDPVDTATYYCAR |
| 13 | VH2-70/JH6 FR4 | WGQGTTVTVSS |
| 14 | VH2-26/JH6 FR1 | EVTLKESGPVLVKPTETLTLTCTVSGFSLS |
| 15 | VH2-26/JH6 FR2 | WIRQPPGKALEWLA |
| 16 | VH2-26/JH6 FR3 | RLTISKDTSKSQVVLTMTNMDPVDTATYYCAR |
| 17 | VH2-26/JH6 FR4 | WGQGTTVTVSS |
| 18 | VH3-72/JH6 FR1 | EVQLVESGGGLVQPGGSLRLSCAASGFTFS |
| 19 | VH3-72/JH6 FR2 | WVRQAPGKGLEWVG |
| 20 | VH3-72/JH6 FR3 | RFTISRDDSKNSLYLQMNSLKTEDTAVYYCAR |
| 21 | VH3-72/JH6 FR4 | WGQGTTVTVSS |
| 22 | VH3-21/JH6 FR1 | EVQLVESGGGLVKPGGSLRLSCAASGFTFS |
| 23 | VH3-21/JH6 FR2 | WVRQAPGKGLEWVS |
| 24 | VH3-21/JH6 FR3 | RFTISRDNAKNSLYLQMNSLRAEDTAVYYCAR |
| 25 | VH3-21/JH6 FR4 | WGQGTTVTVSS |
| 26 | VH1-69/JH6 FR1 | EVQLVQSGAEVKKPGSSVKVSCKASGGTFS |
| 27 | VH1-69/JH6 FR2 | WVRQAPGQGLEWMG |
| 28 | VH1-69/JH6 FR3 | RVTITADKSTSTAYMELSSLRSEDTAVYYCAR |
| 29 | VH1-69/JH6 FR4 | WGQGTTVTVSS |
| 30 | VH1-18/JH6 FR1 | EVQLVQSGAEVKKPGASVKVSCKASGYTFT |
| 31 | VH1-18/JH6 FR2 | WVRQAPGQGLEWMG |
| 32 | VH1-18/JH6 FR3 | RVTMTTDTSTSTAYMELRSLRSDDTAVYYCAR |
| 33 | VH1-18/JH6 FR4 | WGQGTTVTVSS |
| 34 | VH7-4.1/JH6 FR1 | QVQLVQSGSELKKPGASVKVSCKASGYTFT |
| 35 | VH7-4.1/JH6 FR2 | WVRQAPGQGLEWMG |
| 36 | VH7-4.1/JH6 FR3 | RFVFSLDTSVSTAYLQISSLKAEDTAVYYCAR |
| 37 | VH7-4.1/JH6 FR4 | WGQGTTVTVSS |

TABLE 4

Light Chain Acceptor Sequences

| SEQ ID No. | Protein region | Sequence |
|---|---|---|
| 38 | B3/JK4 FR1 | DIVMTQSPDSLAVSLGERATINC |
| 39 | B3/JK4 FR2 | WYQQKPGQPPKLLIY |
| 40 | B3/JK4 FR3 | GVPDRFSGSGSGTDFTLTISSLQAEDVAVYYC |
| 41 | B3/JK4 FR4 | FGGGTKVEIKR |
| 42 | L2/JK4 FR1 | EIVMTQSPATLSVSPGERATLSC |
| 43 | L2/JK4 FR2 | WYQQKPGQAPRLLIY |
| 44 | L2/JK4 FR3 | GIPARFSGSGSGTEFTLTISSLQSEDFAVYYC |
| 45 | L2/JK4 FR4 | FGGGTKVEIKR |
| 46 | L15/JK4 FR1 | DIQMTQSPSSLSASVGDRVTITC |
| 47 | L15/JK4 FR2 | WYQQKPEKAPKSLIY |
| 48 | L15/JK4 FR3 | GVPSRFSGSGSGTDFTLTISSLQPEDFATYYC |
| 49 | L15/JK4 FR4 | FGGGTKVEIKR |
| 50 | L5/JK4 FR1 | DIQMTQSPSSVSASVGDRVTITC |
| 51 | L5/JK4 FR2 | WYQQKPGKAPKLLIY |
| 52 | L5/JK4 FR3 | GVPSRFSGSGSGTDFTLTISSLQPEDFATYYC |
| 53 | L5/JK4 FR4 | FGGGTKVEIKR |
| 54 | 1-33/O18/JK2 FR1 | DIQMTQSPSSLSASVGDRVTITC |
| 55 | 1-33/O18/JK2 FR2 | WYQQKPGKAPKLLIY |
| 56 | 1-33/O18/JK2 FR3 | GVPSRFSGSGSGTDFTFTISSLQPEDIATYYC |
| 57 | 1-33/O18/JK2 FR4 | FGQGTKLEIKR |
| 58 | 1-33/O18/JK4 FR4 | FGGGTKVEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin (see, e.g., Shapiro et al. (2002) Crit. Rev. Immunol. 22(3): 183-200; Marchalonis et al. (2001) Adv. Exp. Med. Biol. 484:13-30). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" refers to antibodies that comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL sequences to replace the corresponding non-human framework (FR) sequences. For example, a "humanized antibody" is an antibody or a variant, derivative, analog, or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 80%, at least 85%, at least 90%, and at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker (1987) *From Genes to Clones* (Verlagsgesellschaft, Weinheim, Germany)). A "consensus immunoglobulin sequence" can thus comprise a "consensus variable domain" and/or a "consensus constant domain". A "consensus variable domain" can in turn comprise one or more "consensus framework regions" and/or one or more "consensus CDRs". In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992) J. Mol. Biol. 224:487-499. Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is engineered to have the three or more antigen binding sites, and is generally not a naturally occurring antibody. The term "multispecific binding protein" refers to a binding protein capable of binding two or more related or unrelated targets. Dual variable domain (DVD) binding proteins are binding proteins that comprise two or more antigen binding sites and are tetravalent or multivalent binding proteins. Such DVD binding proteins may be monospecific, i.e., capable of binding one antigen or multispecific, i.e., capable of binding two or more antigens. DVD binding proteins comprising two heavy chain DVD polypeptides and two light chain DVD polypeptides are referred to as a DVD-Ig™ molecule. Each half of a DVD-Ig™ molecule comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. Pat. No. 7,612,181.

One aspect of the invention pertains to a DVD binding protein comprising binding proteins capable of binding human IL-1α. In another aspect, the DVD binding protein is capable of binding IL-1α and a second target. In one embodiment, the DVD binding protein is capable of binding IL-1α and IL-1β.

The term "neutralizing" refers to neutralization of biological activity of a cytokine when a binding protein specifically binds the cytokine. In an embodiment, a neutralizing binding protein is a neutralizing antibody, whose binding to hIL-1α results in inhibition of a biological activity of hIL-1α. In an embodiment, the neutralizing binding protein binds hIL-1α and reduces a biologically activity of hIL-1α by at least about 20%, at least about 40%, at least about 60%, at least about 80%, at least about 85%, at least about 90%, at least about 95%, or at least about 100% Inhibition of a biological activity of hIL-1α by a neutralizing binding protein can be assessed by measuring one or more indicators of hIL-1α biological activity well known in the art.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. An epitope thus consists of the amino acid residues of a region of an antigen (or fragment thereof) known to bind to the complementary site on the specific binding partner. An antigenic fragment can contain more than one epitope. In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition structural definitions of epitopes (overlapping, similar, identical) are informative, but functional definitions are often more relevant as they encompass structural (binding) and functional (modulation, competition) parameters.

The term "surface plasmon resonance", refers to an optical phenomenon that allows for the analysis of real-time biospecific interactions by detection of alterations in protein concentrations within a biosensor matrix, for example using the BIACORE™ system (Biacore International AB, a GE Healthcare company, Uppsala, Sweden and Piscataway, N.J.). For further descriptions, see JÖnsson, U. et al. (1993) Ann. Biol. Clin. 51:19-26; Jönsson, U. et al. (1991) BioTechniques 11: 620-627; Johnsson, B. et al. (1995) J. Mol. Recognit. 8: 125-131; and Johnsson, B. et al. (1991) Anal. Biochem. 198: 268-277.

The term "Kon" refers to the on rate constant for association of a binding protein (e.g., an antibody) to the antigen to form the, e.g., antibody/antigen complex as is known in the art. The "Kon" also is known by the terms "association rate constant," or "ka," as used interchangeably herein. This value indicating the binding rate of an antibody to its target antigen or the rate of complex formation between an antibody and antigen also is shown by the equation:

Antibody ("Ab")+Antigen ("Ag")→Ab-Ag.

The term "Koff" refers to the off rate constant for dissociation of a binding protein (e.g., an antibody) from the, e.g., antibody/antigen complex as is known in the art. The "Koff" also is known by the terms "dissociation rate constant" or "kd" as used interchangeably herein. This value indicates the dissociation rate of an antibody from its target antigen or separation of Ab-Ag complex over time into free antibody and antigen as shown by the equation below:

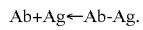

Ab+Ag←Ab-Ag.

The terms "equilibrium dissociation constant" or "$K_D$," as used interchangeably herein, refer to the value obtained in a titration measurement at equilibrium, or by dividing the dissociation rate constant (koff) by the association rate constant (kon). The association rate constant, the dissociation rate constant, and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIACORE™ (biomolecular interaction analysis) assay can be used (e.g., instrument available from Biacore International AB, a GE Healthcare company, Uppsala, Sweden). Additionally, a KinExA® (Kinetic Exclusion Assay) assay, available from Sapidyne Instruments (Boise, Id.) can also be used.

The term "labeled binding protein" as used herein, refers to a protein with a label incorporated that provides for the identification of the binding protein. In one aspect, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm); fluorescent labels (e.g., FITC, rhodamine, and lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. In one aspect the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal" and "crystallized" refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giegé and Ducruix (1999) Chapter 1, In *Crystallization of Nucleic Acids and Proteins, a Practical Approach*, 2nd ed., (Ducruix and Giegé, eds.) (Oxford University Press, New York, 1999) pp. 1-16.

The term "polynucleotide" means a polymeric form of two or more nucleotides, either ribonucleotides or deoxynucleotides, or a modified form of either type of nucleotide. The term includes single and double stranded forms of DNA or RNA, but in an embodiment is double-stranded DNA.

The term "isolated polynucleotide" means a polynucleotide (e.g., of genomic, cDNA, or synthetic origin, or a combination thereof) that is not associated with all or a portion of a polynucleotide with which it is associated in nature, with which it is operably linked to in nature, or with which it occurs in nature as part of a larger sequence.

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a positioning of components such that they function in their intended manner. A control sequence "operably linked" to a coding sequence is ligated in such a way that expression of the coding sequence is achieved under conditions compatible with the control sequences. "Operably linked" sequences include expression control sequences that are contiguous with a nucleic acid of interest, expression control sequences that act in trans, i.e., are located on a different nucleic acid molecule than a nucleic acid of interest but nevertheless exert control over the nucleic acid of interest, and expression control sequences that are located on the same nucleic acid molecule as, but at a distance from, a nucleic acid of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation" refers to any process by which exogenous DNA enters a host cell. Transformation may occur under natural or artificial conditions using various methods well known in the art for the insertion of foreign nucleic acid sequences into a prokaryotic or eukaryotic host cell, for example. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. Such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In one aspect, host cells include prokaryotic and eukaryotic cells selected from any of the Kingdoms of life. Eukaryotic cells include protist, fungal, plant and animal cells. In another aspect, host cells include, but are not limited to, the prokaryotic cell line *Escherichia coli*; mammalian cell lines CHO, HEK 293, and COS; the insect cell line Sf9; and the fungal cell *Saccharomyces cerevisiae*.

Standard techniques may be used for recombinant DNA, oligonucleotide synthesis, and tissue culture and transformation (e.g., electroporation and lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual*, 2d ed. (Cold Spring Harbor Laboratory Press, Cold Spring Harbor, N.Y., 1989).

The term "transgenic organism" refers to an organism having cells that contain a transgene, wherein the transgene introduced into the organism (or an ancestor of the organism) expresses a polypeptide not naturally expressed in the organism. A "transgene" is a DNA construct that is stably and operably integrated into the genome of a cell from which a transgenic organism develops, directing the expression of an encoded gene product in one or more cell types or tissues of the transgenic organism.

The terms "regulate" and "modulate" are used interchangeably and refer to a change or an alteration in the activity of a molecule of interest (e.g., the biological activity of hIL-1α). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator" is a compound capable of changing or altering an activity or function of a molecule of interest (e.g., the biological activity of hIL-1α). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in PCT Publication No. WO 01/83525.

The term "agonist" refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, a polypeptide, a nucleic acid, a carbohydrate, or any other molecule that binds to IL-1α and/or IL-1β.

The term "antagonist" or "inhibitor" refers to a modulator that, when contacted with a molecule of interest, causes a decrease in the magnitude of a certain activity or function of the molecule compared to the magnitude of the activity or function observed in the absence of the antagonist. Antagonists include those that block or modulate the biological or immunological activity of IL-1α and/or IL-1β. Antagonists and inhibitors of IL-1α may include, but are not limited to, a polypeptide, a nucleic acid, a carbohydrate, or any other molecule that binds to IL-1α. Antagonists and inhibitors of IL-1β may include, but are not limited to, a polypeptide, a nucleic acid, a carbohydrate, or any other molecule that binds to IL-1β.

The term "effective amount" refers to the amount of a therapy that is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample" is used in its broadest sense. A "biological sample" includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes, and spleen.

An "affinity matured" antibody is one with one or more alterations in one or more CDRs or frameworks thereof which result in an improvement in the affinity of the antibody for antigen compared to a parent antibody that does not possess such alteration(s). Preferred affinity matured antibodies will have nanomolar or even picomolar affinities for the target antigen. Affinity matured antibodies are produced by procedures known in the art. Marks et al. (1992) BioTechnology 10: 779-783 describes affinity maturation by VH and VL domain shuffling. Random mutagenesis of CDR and/or framework residues is described by Barbas et al. (1994) Proc Nat. Acad. Sci. USA 91: 3809-3813; Schier et al. (1995) Gene 169: 147-155; Yelton et al. (1995) J. Immunol. 155: 1994-2004; Jackson et al. (1995) J. Immunol. 154(7): 3310-3319; and Hawkins et al. (1992) J. Mol. Biol., 226: 889-896.

Pain that persists in an individual after an initial cause for pain has disappeared is no longer a symptom but a recognized disease in its own right. The term "allodynia" as used herein refers to a condition in which an individual experiences a painful response to a normally innocuous stimulus, typically of a mechanical nature, such as brushing of the skin. Allodynic pain does not involve nociceptors and therefore may also be referred to as "non-nociceptive" pain. The term "hyperalgesia" as used herein refers to a condition in which an individual has an increased sensitivity to pain that results from a noxious stimulus, especially a stimulus that activates nociceptors, such as a painful mechanical, thermal, or chemical stimulation. A stimulus that activates nociceptors causes pain. Hyperalgesia is a condition in which an individual has an increased pain response to a normally noxious stimulus. An individual may suffer from allodynia, hyperalgesia, or a combination of allodynia and hyperalgesia.

I. Generation of DVD-Ig™ Binding Proteins that Bind IL-1α and IL-1β

The design and production of dual variable domain immunoglobulin (DVD-Ig™) binding proteins that are capable of binding one or more target antigens (or epitopes) have been described (see, e.g., PCT Publication No. WO 2007/024715). A DVD-Ig binding protein useful in the methods and compositions described herein for treating osteoarthritis binds IL-1α and IL-1β. In an embodiment, a DVD-Ig™ binding protein comprises at least two polypeptide chains, wherein the first polypeptide chain comprises VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, and X2 is an Fc region; and wherein said second polypeptide chain comprises VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1. A DVD-Ig™ binding protein consisting of the first and second polypeptide chains has two antigen binding sites.

In another embodiment, a DVD-Ig™ binding protein comprises four polypeptide chains wherein each of the first two polypeptide chains comprises VD1-(X1)n-VD2-C-(X2)n, respectively wherein VD1 is a first heavy chain variable domain, VD2 is a second heavy chain variable domain, C is a heavy chain constant domain, X1 is a linker with the proviso that it is not CH1, and X2 is an Fc region; and each of the second two polypeptide chains comprises VD1-(X1)n-VD2-C-(X2)n respectively, wherein VD1 is a first light chain variable domain, VD2 is a second light chain variable domain, C is a light chain constant domain, X1 is a linker with the proviso that it is not CH1, and X2 does not comprise an Fc region; and n is 0 or 1. Such a DVD-Ig™ binding protein has four antigen binding sites.

By way of example, a DVD-Ig binding protein useful in the methods and compositions described herein for treating osteoarthritis in an individual may be engineered to have a binding site for IL-1β formed by the association of the VD1 variable domains of the two (first and second polypeptides) and a binding site for IL-1α formed by the association of the VD2 variable domains of the two (first and second polypeptides). In an alternative arrangement, a DVD-Ig binding protein useful in the methods and compositions described herein for treating osteoarthritis in an individual may have a binding site for IL-1α formed by the association of the VD1 variable domains of the two (first and second polypeptides) and a binding site for IL-1β formed by the association of the VD2 variable domains of the two (first and second polypeptides).

A. Generation of Parent Monoclonal Antibodies

The variable domains of the DVD binding protein can be obtained from parent antibodies, including polyclonal and monoclonal antibodies capable of binding antigens of interest. These antibodies may be naturally occurring or may be generated by recombinant technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, 2nd ed., (Cold Spring Harbor Laboratory Press, 1988); Hammerling, et al., *Monoclonal Antibodies and T-Cell Hybridomas* (Elsevier, N.Y., 1981), pages 563-581 (said references incorporated by reference in their entireties). The term "monoclonal antibody"

(abbreviated "mAb") as used herein is not limited to antibodies produced through hybridoma technology. The term "monoclonal antibody" refers to an antibody that is derived from a single clone, including any eukaryotic, prokaryotic, or phage clone, and not the method by which it is produced. Hybridomas are selected, cloned and further screened for desirable characteristics, including robust hybridoma growth, high antibody production and desirable antibody characteristics using standard methods. Hybridomas may be cultured and expanded in vivo in syngeneic animals, in animals that lack an immune system, e.g., nude mice, or in cell culture in vitro. Methods of selecting, cloning, and expanding hybridomas are well known to those of ordinary skill in the art. In a preferred embodiment, hybridomas are mouse hybridomas. In another embodiment, hybridomas are produced in a non-human, non-mouse species such as rats, sheep, pigs, goats, cattle, or horses. In another embodiment, the hybridomas are human hybridomas in which a human non-secretory myeloma is fused with a human cell expressing an antibody capable of binding a specific desired antigen, such as IL-1α or IL-1β.

Recombinant monoclonal antibodies are also generated from single, isolated lymphocytes using a procedure referred to in the art as the selected lymphocyte antibody method (SLAM), as described in U.S. Pat. No. 5,627,052, PCT Publication WO 92/02551 and Babcook et al. (1996) Proc. Natl. Acad. Sci. USA 93:7843-7848. In this method, single cells secreting antibodies of interest, e.g., lymphocytes derived from an immunized animal, are identified, and, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to the antigen of interest. The amplified immunoglobulin sequences further can be manipulated in vitro, such as by in vitro affinity maturation methods such as those described in PCT Publication No. WO 97/29131 and PCT Publication No. WO 00/56772.

Monoclonal antibodies are also produced by immunizing a non-human animal comprising some or all of a human immunoglobulin locus with an antigen of interest. In an embodiment, the non-human animal is a XENOMOUSE transgenic mouse, which is an engineered mouse strain that comprises large fragments of the human immunoglobulin loci and is deficient in mouse antibody production. See, e.g., Green et al. (1994) Nature Genetics 7:13-21 and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/037504. The XENOMOUSE transgenic mouse produces an adult-like human repertoire of fully human antibodies, and generates antigen-specific human monoclonal antibodies. The XENOMOUSE transgenic mouse contains approximately 80% of the human antibody repertoire through introduction of megabase sized, germline configuration YAC fragments of the human heavy chain loci and x light chain loci. See, Mendez et al. (1997) Nature Genet. 15:146-156 and Green and Jakobovits (1998) J. Exp. Med. 188: 483-495.

In vitro methods also can be used to make the parent antibodies, wherein an antibody library is screened to identify an antibody having the desired binding specificity. Methods for such screening of recombinant antibody libraries are well known in the art and include methods described in, for example, U.S. Pat. No. 5,223,409; PCT Publication Nos. WO 92/18619; WO 91/17271; WO 92/20791; WO 92/15679; WO 93/01288; WO 92/01047; WO 92/09690; WO 97/29131; and Fuchs et al. (1991) Bio/Technology 9: 1369-1372; Hay et al. (1992) Hum. Antibod. Hybridomas 3: 81-85; Huse et al. (1989) Science 246: 1275-1281; McCafferty et al. (1990) Nature 348: 552-554; Griffiths et al. (1993) EMBO J. 12: 725-734; Hawkins et al. (1992) J. Mol. Biol. 226: 889-896; Clackson et al. (1991) Nature 352: 624-628; Gram et al. (1992) Proc. Natl. Acad. Sci. USA 89: 3576-3580; Garrard et al. (1991) Bio/Technology 9: 1373-1377; Hoogenboom et al. (1991) Nucl. Acid Res. 19: 4133-4137; and Barbas et al. (1991) Proc. Natl. Acad. Sci. USA 88: 7978-7982, and US Patent Publication No. 2003/0186374.

Parent antibodies useful in the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al. (1995) J. Immunol. Methods 182:41-50; Ames et al. (1995) J. Immunol. Methods 184:177-186; Kettleborough et al. (1994) Eur. J. Immunol. 24: 952-958; Persic et al. (1997) Gene 187: 9-18; Burton et al. (1994) Adv. Immunol. 57:191-280; PCT Application Nos. PCT/GB91/01134; PCT Publication Nos. WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT Publication No. WO 92/22324; Mullinax et al. (1992) BioTechniques 12(6): 864-869; and Sawai et al. (1995) AJRI 34: 26-34; and Better et al. (1988) Science, 240: 1041-1043. Examples of techniques which can be used to produce single-chain Fvs and antibodies include those described in U.S. Pat. Nos. 4,946,778 and 5,258,498; Huston et al. (1991) Methods Enzymol. 203: 46-88; Shu et al. (1993) Proc. Natl. Acad. Sci. USA 90: 7995-7999; and Skerra et al. (1988) Science 240: 1038-1041.

Alternative to screening of recombinant antibody libraries by phage display, other methodologies known in the art for screening large combinatorial libraries can be applied to the identification of parent antibodies. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA*, 94: 12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the parent antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the parent antibodies include those disclosed in U.S. Pat. No. 6,699,658.

The antibodies described above can be further modified to generate CDR-grafted and humanized parent antibodies. CDR-grafted parent antibodies comprise heavy and light chain variable region sequences from a human antibody wherein one or more of the CDR regions of $V_H$ and/or $V_L$ are replaced with CDR sequences of murine antibodies capable of binding antigen of interest. A framework sequence from any human antibody may serve as the template for CDR-grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing such antibodies are known in the art (see, EP 239,400; PCT Publication WO 91/09967; U.S. Pat. Nos. 5,225,539; 5,530,101; and 5,585,089), veneering or resurfacing (EP 592,106; EP 519,596; Padlan (1991) Mol. Immunol. 28(4/5): 489-498; Studnicka et al. (1994) Protein Engineering 7(6): 805-814; Roguska et al. (1994) Proc. Natl. Acad. Sci. USA 91: 969-973), and chain shuffling (U.S. Pat. No. 5,565,352).

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. No. 5,585,089; Riechmann et al. (1988) Nature 332: 323. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al. (1986) Nature 321:522; Verhoeyen et al. (1988) Science 239:1534; Sims et al. (1993) J. Immunol. 151: 2296; Chothia and Lesk (1987) J. Mol. Biol. 196:901; Carter et al. (1992) Proc. Natl. Acad. Sci. USA 89:4285; Presta et al. (1993) J. Immunol. 151:2623; Padlan (1991) Mol. Immunol. 28(4/5):489-498; Studnicka et al. (1994) Protein Engineering 7(6):805-814; Roguska, et al. (1994) Proc. Natl. Acad. Sci. USA 91:969-973; PCT Publication Nos. WO 91/09967; WO 90/14443; WO 90/14424; WO 90/14430; WO 99/06834 (PCT/US98/16280); WO 97/20032 (PCT/US96/18978); WO 92/11272 (PCT/US91/09630); WO 92/03461 (PCT/US91/05939); WO 94/18219 (PCT/US94/01234); WO 92/01047 (PCT/GB91/01134); and WO 93/06213 (PCT/GB92/01755); EP 0 592 106; EP 0 519 596; EP 0 239 400; U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Parent monoclonal antibodies may be selected from various monoclonal antibodies capable of binding IL-1α or IL-1β.

Parent monoclonal antibodies may also be selected from various therapeutic antibodies approved for use, in clinical trials, or in development for clinical use.

B. Construction of DVD-Ig Molecules

A dual variable domain immunoglobulin (DVD-Ig) molecule is designed such that two different light chain variable domains (VL) from the two different parent monoclonal antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. See, PCT Publication No. WO 2007/024715.

The variable domains can be obtained using recombinant DNA techniques from a parent antibody generated by any one of the methods described above. In a preferred embodiment the variable domain is a murine heavy or light chain variable domain. More preferably the variable domain is a CDR grafted or a humanized variable heavy or light chain domain. Most preferably the variable domain is a human heavy or light chain variable domain.

In one embodiment the first and second variable domains are linked directly to each other using recombinant DNA techniques. In another embodiment the variable domains are linked via a linker sequence. Preferably two variable domains are linked. Three or more variable domains may also be linked directly or via a linker sequence. The variable domains may bind the same antigen or may bind different antigens. DVD-Ig molecules of the invention may include one immunoglobulin variable domain and one non-immunoglobulin variable domain such as ligand binding domain of a receptor, active domain of an enzyme. DVD-Ig molecules may also comprise 2 or more non-Ig domains.

The linker sequence may be a single amino acid or a polypeptide sequence. Examples of linker sequences that can be used in designing and producing DVD-Ig binding proteins useful in the methods and compositions described herein include, but are not limited to, AKTTPKLEEGEFSEAR (SEQ ID NO:59); AKTTPKLEEGEFSEARV (SEQ ID NO:60); AKTTPKLGG (SEQ ID NO:61); SAKTTPKLGG (SEQ ID NO:62); SAKTTP (SEQ ID NO:63); RADAAP (SEQ ID NO:64); RADAAPTVS (SEQ ID NO:65); RADAAAAGGPGS (SEQ ID NO:66); RADAAAA($G_4S$)$_4$ (SEQ ID NO:67); SAKTTPKLEEGEFSEARV (SEQ ID NO:68); ADAAP (SEQ ID NO:69); ADAAPTVSIFPP (SEQ ID NO:70); TVAAP (SEQ ID NO:71); TVAAPSVFIFPP (SEQ ID NO:72); QPKAAP (SEQ ID NO:73); QPKAAPSVTLFPP (SEQ ID NO:74); AKTTPP (SEQ ID NO:75); AKTTPPSVTPLAP (SEQ ID NO:76); AKTTAP (SEQ ID NO:77); AKTTAPSVYPLAP (SEQ ID NO:78); ASTKGP (SEQ ID NO:79); ASTKGPSVFPLAP (SEQ ID NO:80); GGSGGGGSG (SEQ ID NO:81); GGGGSGGGGSGGGGS (SEQ ID NO:82); GENKVEYAPALMALS (SEQ ID NO:83); GPAKELTPLKEAKVS (SEQ ID NO:84); GHEAAAVMQVQYPAS (SEQ ID NO:85); TVAAPSVFIFPPTVAAPSVFIFPP (SEQ ID NO:86); and ASTKGPSVFPLAPASTKGPSVFPLAP (SEQ ID NO:87). The choice of linker sequences is based on crystal structure analysis of several Fab molecules. There is a natural flexible linkage between the variable domain and the CH1/CL constant domain in Fab or antibody molecular structure. This natural linkage comprises approximately 10-12 amino acid residues, contributed by 4-6 residues from C-terminus of V domain and 4-6 residues from the N-terminus of CL/CH1 domain. In an embodiment, a DVD-Ig molecule useful in the invention is generated using N-terminal 5-6 amino acid residues or 11-12 amino acid residues of CL or CH1 as linker in light and heavy chains of a DVD-Ig molecule, respectively. The N-terminal residues of CL or CH1 domains, particularly the first 5-6 amino acid residues, adopt a loop conformation without strong secondary structures, and therefore can act as flexible linkers between the two variable domains. The N-terminal residues of CL or CH1 domains are natural extensions of the variable domains, as they are part of the immunoglobulin sequences, and therefore minimize to a large extent any immunogenicity potentially arising from the linkers and junctions.

Other linker sequences may include any sequence of any length of CL/CH1 domain but not all residues of CL/CH1 domain; for example the first 5-12 amino acid residues of the CL/CH1 domains; the light chain linkers can be from Cκ or Cλ; and the heavy chain linkers can be derived from CH1 of any isotypes, including Cγ1, Cγ2, Cγ3, Cγ4, Cα1, Cα2, Cδ, Cε, and Cμ. Linker sequences may also be derived from other proteins such as Ig-like proteins, (e.g., TCR, FcR, KIR); G/S based sequences (e.g., G4S (SEQ ID NO:88) repeats); hinge region-derived sequences; and other natural sequences from other proteins.

In an embodiment, a constant domain is linked to the two linked variable domains using recombinant DNA techniques. Preferably, a sequence comprising linked heavy chain variable domains is linked to a heavy chain constant domain and a sequence comprising linked light chain variable domains is linked to a light chain constant domain. Preferably, the constant domains are human heavy chain constant domain and human light chain constant domain, respectively, when the DVD-Ig binding protein is to be used in a human. Preferably, a DVD-Ig heavy chain is further linked to an Fc region. The Fc region may be a native sequence Fc region, or a variant Fc region. Most preferably, the Fc region is a human Fc region. In a preferred embodiment the Fc region includes Fc region from IgG1, IgG2, IgG3, IgG4, IgA, IgM, IgE, or IgD.

In an embodiment, two heavy chain DVD-Ig polypeptides and two light chain DVD-Ig polypeptides are combined to form a DVD-Ig molecule. Detailed descriptions of examples of specific DVD-Ig molecules capable of binding specific targets and methods of making the same have been described. See, e.g., PCT Publication No. WO 2007/024715.

C. Production of DVD-Ig Binding Proteins

DVD-Ig proteins that bind IL-1α and IL-1β and are useful in the methods and compositions described herein for treating osteoarthritis may be produced by any of a number of techniques known in the art. See, for example, PCT Publication No. 2007/024715. For example, expression from host cells, wherein expression vector(s) encoding the DVD-Ig heavy and DVD-Ig light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express DVD-Ig binding proteins in either prokaryotic or eukaryotic host cells, expression of DVD-Ig proteins in eukaryotic cells is preferable, and most preferable in mammalian host cells, because such eukaryotic cells (and in particular mammalian cells) are more likely than prokaryotic cells to assemble and secrete a properly folded and immunologically active DVD-Ig protein.

Preferred mammalian host cells for expressing the recombinant antibodies of the invention include Chinese Hamster Ovary (CHO cells) (including dhfr-CHO cells, described in Urlaub and Chasin (1980) Proc. Natl. Acad. Sci. USA 77: 4216-4220, used with a DHFR selectable marker, e.g., as described in R. J. Kaufman and P. A. Sharp (1982) Mol. Biol. 159: 601-621), NS0 myeloma cells, COS cells, and SP2 cells. When recombinant expression vectors encoding DVD-Ig proteins are introduced into mammalian host cells, the DVD-Ig proteins are produced by culturing the host cells for a period of time sufficient to allow for expression of the DVD-Ig proteins in the host cells or, more preferably, secretion of the DVD-Ig proteins into the culture medium in which the host cells are grown. DVD-Ig proteins can be recovered from the culture medium using standard protein purification methods.

In a preferred system for recombinant expression of DVD-Ig proteins useful in the invention, a recombinant expression vector encoding both the DVD-Ig heavy chain and the DVD- Ig light chain is introduced into dhfr-CHO cells by calcium phosphate-mediated transfection. Within the recombinant expression vector, the DVD-Ig heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the DVD-Ig heavy and light chains and intact DVD-Ig protein is recovered from the culture medium. Standard molecular biology techniques are used to prepare the recombinant expression vector, transfect the host cells, select for transformants, culture the host cells and recover the DVD-Ig protein from the culture medium. Still further the invention provides a method of synthesizing a DVD-Ig protein of the invention by culturing a host cell of the invention in a suitable culture medium until a DVD-Ig protein of the invention is synthesized. The method can further comprise isolating the DVD-Ig protein from the culture medium.

An important feature of a DVD-Ig binding protein is that it can be produced and purified in a similar way as a conventional antibody. The production of DVD-Ig binding protein results in a homogeneous, single major product with desired dual-specific activity, without any sequence modification of the constant region or chemical modifications of any kind. Other previously described methods to generate "bi-specific", "multi-specific", and "multi-specific multivalent" full length binding proteins do not lead to a single primary product but instead lead to the intracellular or secreted production of a mixture of assembled inactive, mono-specific, multi-specific, multivalent, full length binding proteins, and multivalent full length binding proteins with combination of different binding sites. As an example, based on the design described by Miller and Presta (PCT Publication No. WO2001/077342, there are 16 possible combinations of heavy and light chains. Consequently only 6.25% of protein is likely to be in the desired active form. Separation of fully active forms of the protein from inactive and partially active forms of the protein using standard chromatography techniques, typically used in large scale manufacturing, is yet to be demonstrated.

Surprisingly, the design of the DVD-Ig binding proteins, which are "dual-specific multivalent full-length binding proteins", led to a dual variable domain light chain and a dual variable domain heavy chain that assemble primarily to the desired "dual-specific multivalent full length binding proteins", i.e., a functional DVD-Ig binding protein. See, PCT Publication No. WO 2007/024715.

II. Crystalline and Derivatized Binding Proteins

The invention includes methods and compositions for treating osteoarthritis that a binding protein that is a crystal. In an embodiment, the crystallized binding protein has a greater half-life in vivo than the soluble counterpart of the binding protein. In another embodiment, the binding protein retains biological activity after crystallization.

Crystallized binding proteins useful in the invention may be produced according to methods known in the art and as disclosed in PCT Publication No. WO 02072636, incorporated herein by reference.

Another embodiment of the invention employs a glycosylated binding protein wherein a binding protein or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (Jefferis (2005) Biotechnol. Prog., 21: 11-16). In contrast, glycosylation of the variable domain may have an effect on the antigen binding activity of the antibody. Glycosylation in the variable domain may have a negative effect on antibody binding affinity, likely due to steric hindrance (Co et al. (1993) Mol. Immunol. 30: 1361-1367), or result in increased affinity for the antigen (Wallick et al. (1998) Exp. Med. 168:1099-1109; Wright et al. (1991) EMBO J. 10:2717-2723).

It is also possible to generate glycosylation site mutants in which an O- or N-linked glycosylation site of s binding protein has been mutated. One skilled in the art can generate such mutants using standard technologies. Glycosylation site mutants that retain the biological activity but have increased or decreased binding activity may also be used in the methods and compositions described herein for treating osteoarthritis.

The glycosylation of a binding protein or antigen-binding portion thereof useful in the methods and compositions of the invention may be modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication No. WO 2003/016466 and U.S. Pat. Nos. 5,714,350 and 6,350,861.

Additionally or alternatively, a modified binding protein useful in the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the binding protein in a host cell with altered glycosylation machinery. Cells with altered glycosylation machinery have been described in the art and can be used as host cells in which to express recombinant antibodies of the invention to thereby produce an antibody with altered glycosylation. See, for example, Shields et al. (2002) J. Biol. Chem. 277: 26733-26740; Umana et al. (1999) Nat. Biotech. 17: 176-181, as well as, European Patent No. EP 1,176,195; and PCT Publication Nos. WO 03/035835 and WO 99/5434280.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues of a binding protein useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (US Patent Publication Nos. 2004/0018590 and 2002/0137134 and PCT Publication No. WO 2005/100584).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

IV. Pharmaceutical Compositions

The methods of the invention employ pharmaceutical compositions for treating osteoarthritis or pain in an individual that comprise one or more binding proteins that bind IL-1α and/or IL-1β. Such compositions can also comprise a pharmaceutically acceptable carrier, a diluent, and/or excipient, or any other compound(s) that provides a desirable therapeutic, pharmaceutical, or pharmacological benefit to the composition other than the activity of the one or more binding proteins to bind IL-1α and/or IL-1β. In an embodiment, a composition useful in treating osteoarthritis or pain in an individual according to the invention comprises a binding protein that binds IL-1α, for example an anti-IL-1α antibody, and a binding protein that binds IL-1β, such as an anti-IL-1β antibody, or a binding protein that binds both IL-1α and/or IL-1β, such as an IL-1α/β DVD-Ig binding protein.

Binding proteins useful in the methods of the invention can be incorporated into pharmaceutical compositions suitable for administration to a subject. Typically, a pharmaceutical composition comprises one or more binding proteins that bind IL-1α and/or IL-1β and a pharmaceutically acceptable carrier. As used herein, "pharmaceutically acceptable carrier" broadly includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include an isotonic agent, for example, sugar, polyalcohol (e.g., mannitol or sorbitol), or sodium chloride in a composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more binding proteins useful in the invention or a combination of one or more binding proteins and a prophylactic agent or other therapeutic agent useful for preventing, managing, treating, or ameliorating osteoarthritis or pain in an individual, e.g., encapsulation in liposomes, microparticles, microcapsules, recombinant cells capable of expressing the binding protein or fragment, and receptor-mediated endocytosis (see, e.g., Wu and Wu (1987) J. Biol. Chem., 262: 4429-4432), construction of a nucleic acid as part of a retroviral or other vector, etc. Methods of administering to an individual a binding protein that binds IL-1α and/or IL-1β include, but are not limited to, parenteral administration (e.g., intradermal, intramuscular, intraperitoneal, intravenous, and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; and 5,290,540; and PCT Publication Nos. WO 92/19244, WO 97/32572, WO 97/44013, WO 98/31346, and WO 99/66903. In one embodiment, a binding protein useful in the invention is administered using Alkermes AIR® pulmonary drug delivery technology (Alkermes, Inc., Cambridge, Mass.). In a specific embodiment, a binding protein useful in the invention is administered intramuscularly, intravenously, intratumorally, orally, intranasally, pulmonary, or subcutaneously. A binding protein may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer a binding protein locally to the area in need of treatment, such as directly into the joint area. This may be achieved by, for example, and not by way of limitation, local infusion, by injection, or by means of an implant, wherein the implant is a porous or non-porous material, including membranes and matrices, such as sialastic membranes, polymers, fibrous matrices (e.g., Tissuel®), or collagen matrices. In an embodiment, an effective amount of one or more binding proteins is administered locally to the affected joint to treat, manage, ameliorate, and/or prevent further progression of cartilage degeneration as otherwise occurs in osteoarthritis, including pain. In another embodiment, an effective amount of one or more binding proteins is administered locally to an affected joint in combination with an effective amount of one or more other therapies (e.g., one or more prophylactic or therapeutic agents) other than the binding protein(s) to prevent, treat, manage, and/or ameliorate osteoarthritis or one or more symptoms thereof, including pain.

In another embodiment, IL-1α and IL-1β binding proteins can be delivered in a controlled release or sustained release system. In one embodiment, a pump may be used to achieve controlled or sustained release (see Langer (1990) Science 249:1527-1533; Sefton (1987) CRC Crit. Rev. Biomed. Eng., 14: 201-240; Buchwald et al. (1980) Surgery, 88: 507-516; Saudek et al. (1989) N. Engl. J. Med., 321: 574-579). In another embodiment, polymeric materials can be used to achieve controlled or sustained release of binding proteins useful in the invention (see, e.g., *Medical Applications of Controlled Release*, (Langer and Wise, eds.) (CRC Press, Inc., Boca Raton, 1984); *Controlled Drug Bioavailability, Drug Product Design and Performance*, (Smolen and Ball, eds.) (Wiley, New York, 1984); Langer and Peppas (1983) J. Macromol. Sci. Rev. Macromol. Chem. Phys., C23: 61-126; see also Levy et al. (1985) Science 228:190-192; During et al. (1989) Ann. Neurol., 25: 351-356; Howard et al. (1989) J. Neurosurg. 71:105-112); U.S. Pat. Nos. 5,679,377; 5,916,597; 5,912,015; 5,989,463; and 5,128,326; and PCT Publication Nos. WO 99/15154 and WO 99/20253. Examples of polymers that be used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, J. M., Chapter 6, In *Medical Applications of Controlled Release, Vol. II, Applications and Evaluation*, (Langer and Wise, eds.) (CRC Press, Inc., Boca Raton, 1984), pp. 115-138).

Controlled release systems are discussed in the review by Langer, *Science*, 249: 1527-1533 (1990). Any technique known to one of skill in the art can be used to produce sustained release formulations comprising one or more therapeutic agents of the invention. See, e.g., U.S. Pat. No. 4,526,938; PCT Publication Nos. WO 91/05548 and WO 96/20698; Ning et al. (1996) Radiother. Oncol., 39: 179-189; Song et al. (1996) PDA J. Pharm. Sci. Technol., 50: 372-377; Cleek et al. (1997) Proceed. Intl Symp. Control. Rel. Bioact. Mater. 24: 853-854; and Lam et al. (1997) Proceed. Intl Symp. Control Rel. Bioact. Mater., 24: 759-760.

In a specific embodiment, where a composition useful in the invention is a nucleic acid encoding a protein that binds IL-1α and/or IL-1β, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see, e.g., U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide, which is known to enter the nucleus (see, e.g., Joliot et al. (1991) Proc. Natl. Acad. Sci. USA 88:1864-1868). Alternatively, a nucleic acid can be introduced intracellularly and incorporated within host cell DNA for expression by homologous recombination.

A pharmaceutical composition useful in the invention for treating osteoarthritis or pain is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions useful in the invention for treating osteoarthritis or pain are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences and Introduction to Pharmaceutical Dosage Forms, 19th ed.*, (Mack Publishing Co., Easton, Pa., 1995). For non-sprayable topical dosage forms, viscous to semi-solid or solid forms comprising a carrier or one or more excipients compatible with topical application and having a dynamic viscosity preferably greater than water are typically employed. Other suitable formulations include, without limitation, suspensions, powders, liniments, salves, and the like. In an embodiment, such formulations are sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example, in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If a method of the invention for treating osteoarthritis or pain comprises intranasal administration of a composition, the composition can be formulated in an aerosol form, spray, mist, or in the form of drops. In particular, a binding protein for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If a method of the invention for treating osteoarthritis or pain comprises oral administration, a composition can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a binding protein(s) useful in the invention for treating osteoarthritis or pain.

A method for treating osteoarthritis or a method of treating pain according to the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; and 5,290,540; and PCT Publication Nos. WO 92/19244; WO 97/32572; WO 97/44013; WO 98/31346; and WO 99/66903. In a specific embodiment, a binding protein that binds IL-1α and/or IL-1β or combination therapy for treating osteoarthritis is administered using Alkermes AIR® pulmonary drug delivery technology (Alkermes, Inc., Cambridge, Mass.).

A method of the invention may comprise administration of a composition comprising a binding protein that binds IL-1α and/or IL-1β that is formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions, or emulsions in oily or aqueous vehicles, and may contain formulatory agents such as suspending, stabilizing and/or dispersing agents. Alternatively, a binding protein may be in powder form for constitution with a suitable vehicle (e.g., sterile pyrogen-free water) before use.

Methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

Methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The invention also provides one or more binding proteins that bind IL-1α and/or IL-1β or a pharmaceutical composition comprising such binding proteins packaged in a hermetically sealed container such as an ampoule or sachette indicating the quantity of the agent. In an embodiment, one or more binding proteins that bind IL-1α and/or IL-1β or a pharmaceutical composition comprising such binding protein(s) is supplied as a dry sterilized lyophilized powder or water free concentrate in a hermetically sealed container and can be reconstituted (e.g., with water or saline) to the appropriate concentration for administration to a subject to treat arthritis or pain. In an embodiment, one or more binding proteins that bind IL-1α and/or IL-1β or a pharmaceutical composition comprising such binding protein(s) is supplied as a dry sterile lyophilized powder in a hermetically sealed container at a unit dosage of at least about 5 mg, at least about 10 mg, at least about 15 mg, at least about 25 mg, at least about 35 mg, at least about 45 mg, at least about 50 mg, at least about 75 mg, or at least about 100 mg. The lyophilized binding protein(s) or pharmaceutical composition comprising such binding protein(s) should be stored at between about 2° C. and about 8° C. in its original container and binding protein(s) or pharmaceutical composition comprising such binding protein(s) should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more binding proteins that bind IL-1α and/or IL-1β or a pharmaceutical composition comprising such binding protein(s) is supplied in liquid form in a hermetically sealed container indicating the quantity and concentration of the agent. In an embodiment, the liquid form of the administered composition is supplied in a hermetically sealed container at least about 0.25 mg/ml, at least about 0.5 mg/ml, at least about 1 mg/ml, at least about 2.5 mg/ml, at least about 5 mg/ml, at least about 8 mg/ml, at least about 10 mg/ml, at least about 15 mg/kg, at least about 25 mg/ml, at least about 50 mg/ml, at least about 75 mg/ml or at least about 100 mg/ml. The liquid form should be stored at between about 2° C. and about 8° C. in its original container.

Binding proteins useful in the methods and compositions described herein can be incorporated into a pharmaceutical composition suitable for parenteral administration. In one aspect, binding proteins will be prepared as an injectable solution containing about 0.1 mg/ml to about 250 mg/ml antibody. The injectable solution can be composed of either a liquid or lyophilized dosage form in a flint or amber vial, ampoule, or pre-filled syringe. The buffer can be L-histidine (about 1 mM to about 50 mM), optimally about 5 mM to about 10 mM, at about pH 5.0 to about 7.0 (optimally about pH 6.0). Other suitable buffers include but are not limited to, sodium succinate, sodium citrate, sodium phosphate or potassium phosphate. Sodium chloride can be used to modify the toxicity of the solution at a concentration of about 0 to about 300 mM (optimally about 150 mM for a liquid dosage form). Cryoprotectants can be included for a lyophilized dosage form, principally about 0% to about 10% sucrose (optimally about 0.5% to about 1.0%). Other suitable cryoprotectants include trehalose and lactose. Bulking agents can be included for a lyophilized dosage form, principally about 1% to about 10% mannitol (optimally about 2% to about 4%). Stabilizers can be used in both liquid and lyophilized dosage forms, principally about 1 mM to about 50 mM L-methionine (optimally about 5 mM to about 10 mM). Other suitable bulking agents include glycine, arginine, can be included as about 0% to about 0.05% polysorbate-80 (optimally about 0.005% to about 0.01%). Additional surfactants include but are not limited to polysorbate 20 and BRIJ surfactants.

Compositions useful for treating osteoarthritis or pain according to the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The particular form depends on the intended mode of administration and therapeutic application. Typical compositions are in the form of injectable or infusible solutions, such as compositions similar to those used for passive immunization of humans with antibodies. The mode of administration is parenteral (e.g., intravenous, subcutaneous, intraperitoneal, intramuscular). In an embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, or antigen binding portion thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, exemplary methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The binding proteins useful for treating osteoarthritis or pain according to the invention can be administered by a variety of methods known in the art, although an exemplary route/mode of administration is subcutaneous injection, intravenous injection, or infusion. As will be appreciated by the skilled artisan, the route and/or mode of administration will vary depending upon the desired results. In certain embodiments, a binding protein(s) may be prepared with a carrier that will protect the binding protein(s) against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., (Marcel Dekker, Inc., New York, 1978).

In certain embodiments, a binding protein(s) useful in the invention may be orally administered, for example, with an inert diluent or an assimilable edible carrier. The binding protein(s) (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a binding protein (e.g., an antibody), or antigen binding portion thereof, useful in the invention is coformulated with and/or coadministered with one or more additional therapeutic agents that are useful for treating osteoarthritis or pain. For example, a binding protein that binds hIL-1α and/or hIL-1β, or antigen binding portion(s) thereof, may be coformulated and/or coadministered with one or more additional antibodies that bind other targets (e.g., antibodies that bind other cytokines or that bind cell surface molecules). Furthermore, one or more binding proteins may be used in combination with one or more other therapeutic agents. Such combination therapies may advantageously utilize lower dosages of the administered therapeutic agents, thus avoiding possible toxicities or complications associated with the various monotherapies.

In certain embodiments, a protein(s) that binds IL-1α and/or IL-1β, or binding portion thereof, is linked to a half-life extending vehicle known in the art. Such vehicles include, but are not limited to, the Fc domain, polyethylene glycol, and dextran. Such vehicles are described, e.g., in U.S. Pat. No. 6,660,843.

In a specific embodiment, nucleic acid molecules comprising nucleotide sequences encoding one or more polypeptides of a binding protein are administered to treat, prevent, manage, or ameliorate osteoarthritis by way of gene therapy. Gene therapy refers to therapy performed by the administration to a subject of an expressed or expressible nucleic acid. In this embodiment of the invention, the nucleic acids produce their encoded binding polypeptide(s) for a binding protein(s) that binds IL-1α and/or IL-1β and mediates a prophylactic or therapeutic effect with respect to osteoarthritis or pain.

Any of the methods for gene therapy available in the art can be used according to the present invention. For general reviews of the methods of gene therapy, see Goldspiel et al. (1993) Clin. Pharm. 12:488-505; Wu and Wu (1991) Biotherapy 3: 87-95; Tolstoshev (1993) Ann. Rev. Pharmacol. Toxicol. 32: 573-596; Mulligan (1993) Science 260: 926-932; Morgan and Anderson (1993) Ann. Rev. Biochem. 62:191-217; and Robinson, C. (1993) Trends Biotechnol. 11(5):155. Methods commonly known in the art of recombinant DNA technology which can be used are described in Ausubel et al. (eds.), *Current Protocols in Molecular Biology* (John Wiley & Sons, New York, 1993); and Kriegler, *Gene Transfer and Expression, A Laboratory Manual*, (Stockton Press, New York, 1990). Detailed descriptions of various methods of gene therapy are disclosed in US patent application publication No. 2005/0042664.

A binding protein(s) that binds IL-1α and/or IL-1β can be used alone or in combination with one or more additional agents useful in the treatment of osteoarthritis or pain. For example, an additional agent can be a therapeutic agent art-recognized as being useful to treat one or more symptoms of osteoarthritis or to affect a target other than IL-1 that is associated with pain. An additional agent also can be an agent that imparts a beneficial attribute to the therapeutic composition e.g., an agent that affects the viscosity of the composition to be administered to an individual.

It should further be understood that the combinations that are to be included within this invention are those combinations useful for their intended purpose. The agents set forth below are illustrative for purposes and not intended to be limiting. The combinations, which are part of this invention, can be a binding protein(s) that binds IL-1α and/or IL-1β and at least one additional agent that provides a desirable property. A combination can also include more than one additional agent, e.g., two or three additional agents, if the combination is such that the formed composition can perform its intended function. Preferred combinations to treat osteoarthritis or pain include non-steroidal anti-inflammatory drug(s) also referred to as "NSAIDS", which include drugs like ibuprofen. Other preferred combinations are anti-inflammatory agents, including corticosteroids, such as prednisolone; the well known side-effects of steroid use can be reduced or even eliminated by tapering the steroid dose required when treating patients in combination with a binding protein(s) that binds IL-1α and/or IL-1β. Non-limiting examples of therapeutic agents for use in treating an individual suffering from osteoarthritis or pain may include, but are not limited to, one or more the following: budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies of TNF, LT, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, an NSAID, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13, and TGFβ.

The pharmaceutical compositions of the invention may include a "therapeutically effective amount" or a "prophylactically effective amount" of one or more binding protein(s) that binds IL-1α and/or IL-1β. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein(s), or portion(s) thereof, are outweighed by the therapeutically beneficial effects. A "prophylactically effective amount" refers to an amount effective, at dosages and for periods of time necessary, to achieve the desired prophylactic result, such as preventing further degeneration or loss of articular cartilage in an affected joint in osteoarthritis or to prevent onset or intensification of pain. Typically, since a prophylactic dose is used in subjects prior to or at an earlier stage of disease, the prophylactically effective amount will be less than the therapeutically effective amount.

In an embodiment, a method for treating an individual for pain wherein the individual is suffering from a disease or disorder associated with IL-1 accumulation. Such IL-1 accumulation in an individual can be the result of reduced IL-1 expression or reduced metabolism of IL-1. Accumulation of IL-1 can occur in the blood (including plasma, serum) or a local tissue of the individual.

In an embodiment, the invention provides a method for treating an individual for pain wherein the individual is suffering from a disease or disorder associated with IL-1 accumulation.

In an embodiment, compositions and methods described herein can be used to treat pain in an individual suffering a disease or disorder selected from the group comprising osteoarthritis, rheumatoid arthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis, scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I, polyglandular deficiency type II (Schmidt's syndrome), adult (acute) respiratory distress syndrome, alopecia, alopecia areata, seronegative arthropathy, arthropathy, Reiter's disease, psoriatic arthropathy, ulcerative colitic arthropathy, enteropathic synovitis, *Chlamydia*-associated arthropathy, *Yersinia*-associated arthropathy, *Salmonella*-associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free disease, chronic mucocutaneous candidiasis, giant cell arteritis, primary sclerosing hepatitis, cryptogenic autoimmune hepatitis, acquired immunodeficiency syndrome, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, cholestasis, idiosyncratic liver disease, drug-induced hepatitis, non-alcoholic steatohepatitis, allergy, group B streptococci (GBS) infection, mental disorders (e.g., depression and schizophrenia), Th2 Type and Th1 Type mediated diseases, acute and chronic pain (different forms of pain), cancers such as lung, breast, stomach, bladder, colon, pancreas, ovarian, prostate and rectal cancer and hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, atrial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis A, His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic migraine headache, idiopathic migraine headache, mitochondrial multisystem disorder, mixed connective tissue disease, monoclonal gammopathy, multiple myeloma, multiple systems degenerations (Menzel, Dejerine-Thomas, Shy-Drager, and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-Hodgkin's lymphoma, occlusion of the abdominal aorta and its branches, occlusive arterial disorders, OKT3® therapy, orchitis/epididymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon, Raynaud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangiitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia areata, anaphylaxis, anti-phospholipid antibody syndrome, aplastic anemia, arteriosclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, childhood onset psychiatric disorder, chronic obstructive pulmonary disease (COPD), dacryocystitis, dermatomyositis, diabetic retinopathy, disk herniation, disk prolapse, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier disease, Landry's paralysis, Langerhan's cell histiocytosis, livedo reticularis, macular degeneration, microscopic polyangiitis, Morbus Bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, ovarian cancer, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor-necrosis factor receptor type 1 (TNFR)-associated periodic syndrome), type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, and wound healing.

Compositions and methods described herein can be used to treat pain in an individual suffering from a disease selected from the group consisting of primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of a binding protein(s) that binds IL-1α and/or IL-1β and the particular therapeutic or prophylactic effect to be achieved, and (b) the limitations inherent in the art of compounding such protein(s) for the treatment of individuals.

An exemplary, non-limiting range for a therapeutically or prophylactically effective amount of a binding protein useful in the treatment of osteoarthritis or pain is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods and compositions of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Generation of Dual Variable Domain Immunoglobulin (DVD-Ig) Protein

A dual variable domain immunoglobulin (DVD-Ig) molecule is designed such that two different light chain variable domains (VL) from two different parent mAbs are linked in tandem directly or via a short linker by recombinant DNA techniques, followed by a light chain constant domain. Similarly, the heavy chain comprises two different heavy chain variable domains (VH) linked in tandem directly or via a short linker, followed by a constant domain CH1 and Fc region. See FIG. 1A. The design and production of DVD-Ig binding proteins from parental monoclonal antibodies, including examples of a DVD-Ig binding protein that bind to IL-1α and IL-1β as produced from a parental anti-IL-1α monoclonal antibody and a parental anti-IL-1β monoclonal antibody, has been described. See, PCT Publication No. WO 2007/024715 A2 and Wu et al., *Nature Biotechnol.*, 25(11): 1290-1297 (2007), incorporated herein by reference. Descriptions of selected monoclonal antibodies to IL-1α and IL-1β and their use as parental monoclonal antibodies for the production of DVD-Ig molecules that bind both IL-1α and IL-1β are provided herein. The DVD-Ig molecules were characterized for possible therapeutic activity using known animal models for rheumatoid arthritis and osteoarthritis.

Example 1.1

Generation of Murine Monoclonal Antibodies to IL-1α and IL-1β

Monoclonal antibodies (mAbs) to IL-1α and IL-1β were generated as follows using standard hybridoma technology.

Example 1.1.A

Immunization Of Mice

Purified recombinant human IL-1α and murine IL-1β (R&D Systems) were used as immunogens as well as coating antigens in titer assays and screening ELISA Immunizing dosages ranged from 5.0 to 20.0 μg/mouse/injection for all antigens for both primary and boost immunizations. ImmunEasy adjuvant was purchased from Qiagen (Waltham, Mass.) and used at adjuvant/antigen ratio of 20 ml ImmunEasy adjuvant per 10.0 μg antigen. Each group of animals to be immunized contained five IL-1αβ KO mice obtained from Dr. Yoichiro Iwakura (University of Tokyo, Minato-ku, Tokyo, Japan). The mice were immunized according to dosing schedule described below. MRC-5 cells were purchased from ATCC (Manassas, Va.) and used for IL-1 bioassay. Human IL-8 ELISA kits and control mouse anti-hIL-1α and anti-hIL-1β antibodies (MAB200 and MAB201) were purchased from R&D Systems (Minneapolis, Minn.).

Briefly, adjuvant-antigen mixture was prepared by first gently mixing the adjuvant in a vial using a vortex. The desired amount of adjuvant was removed from the vial and put into an autoclaved 1.5 mL microcentrifuge tube. The antigen was prepared in PBS or saline with concentration ranging from 0.5-1.0 mg/ml. The calculated amount of antigen was then added to the microcentrifuge tube with the adjuvant and the solution was mixed by gently pipetting up and down 5 times. The adjuvant-antigen mixture was incubated at room temperature for 15 minutes and then mixed again by gently pipetting up and down 5 times. The adjuvant-antigen solution was drawn into the proper syringe for animal injection. A total of 5-20 μg of antigen was injected in a volume of 50-100 μl. Each animal was immunized, and then boosted 2 to 3 times depending on the titer. Animals with good titers were given a final intravenous boost before fusion and generation of hybridomas.

Example 1.1.B

Screening Hybridomas

Hybridomas, generated as described above, were screened and antibody titer determined using ELISA. Protein antigens were directly coated on ELISA plates for detecting the specific antibodies using standard ELISA procedures. Briefly, ELISA plates were coated with 100 μl of either rhIL-1α or rhIL-1β (1.0 μg/ml in PBS) overnight at 4° C. Plates were washed 3 times with 250 μl PBS/0.5% Tween$_{20}$ and blocked with 200 μl blocking buffer (2% BSA in PBS with 0.5% Tween$_{20}$). Diluted sera or hybridoma supernatant (100 μl) was added to each well, and incubated at room temperature for 2 hours. Plates were then washed three times with PBS/0.5% Tween$_{20}$. HRP-goat anti-murine IgG was used for detection, and binding ODs were observed at 450 nm. Hybridoma clones producing antibodies that showed high specific binding activity in the ELISA were subcloned and purified, and affinity (Biacore) and potency (MRC-5 bioassay) of the antibodies were characterized as follows.

Example 1.1.C

Characterization of Murine Monoclonal Antibodies to IL-1α and IL-1β

The following assays were used to characterize the antibodies produced by the hybridomas described in Example 1.1.B.

Example 1.1.C.1

Surface Plasmon Resonance

Real-time binding interactions between antibody (mouse anti-recombinant mIL-1 antibody) captured on a biosensor matrix via goat anti-mouse IgG and rmIL-1 were measured by surface plasmon resonance (SPR) using the BIAcore system (Biacore AB, Uppsala, Sweden) according to manufacturer's instructions and standard procedures. Briefly, rmIL-1 was diluted in HBS running buffer (Biacore AB) and 50 μl aliquots were injected through the immobilized protein matrices at a flow rate of 5 ml/minutes. The concentrations of rhIL-1 employed were 62.5, 125, 187.5, 250, 375, 500, 750, 1000, 1500, and 2000 nM. To determine the dissociation constant (off-rate), association constant (on-rate), BIAcore kinetic evaluation software (version 3.1) was used.

Example 1.1.C.2

Anti-IL-1 Bioassay

The MRC-5 cell line is a human lung fibroblast cell line that produces IL-8 in response to human IL-1α and IL-1β in a dose-dependent manner (see, Dinarello, Muegge, and Durum (2000) Curr. Protocols Immunol. 6:1). MRC-5 cells were cultured in 10% FBS complete MEM and grown at 37° C. in a 5% $CO_2$ incubator. To determine neutralizing potencies of the monoclonal antibodies (mAbs) against recombinant human IL-1α or IL-1β, different concentrations (0-10 μg/ml) of mAb (50 μl) was added to a 96-well plate and pre-incubated with 50 μl of rhIL-1α or rhIL-1β (10-50 pg/ml) for 1 hour at 37° C. The supernatants were harvested, diluted, and IL-8 concentrations measured by ELISA using a standard IL-8 ELISA kit (R&D Systems). Antibody potency was determined by its ability to inhibit IL-8 production by MRC-5 cells.

Based on Biacore and MRC-5 bioassay, a number of murine anti-hIL-1α and anti-hIL-1β antibodies with high affinity and potency were identified, as shown in Table 1 below:

TABLE 1

Generation And Characterization Of Murine Anti-Hil-1α/β Mabs

| mAb Clone# | Specificity | KD (M) | IC50 (M) |
|---|---|---|---|
| 3D12.E3 | hIL-1α | $1.11 \times 10^{-9}$ | $6.70 \times 10^{-10}$ |
| 18F4.2C8 | hIL-1α | $5.78 \times 10^{-10}$ | $8.90 \times 10^{-11}$ |
| 6H3.1A4.3E11 | hIL-1α | $3.54 \times 10^{-10}$ | $2.40 \times 10^{-10}$ |
| 13F5.G5 | hIL-1β | $2.91 \times 10^{-10}$ | $6.00 \times 10^{-10}$ |
| 1B12.4H4 | hIL-1β | $2.13 \times 10^{-10}$ | $5.30 \times 10^{-10}$ |
| 6B12.4F6 | hIL-1β | $5.54 \times 10^{-10}$ | $3.20 \times 10^{-10}$ |

Example 1.1.D

Cloning and Sequencing of the Murine Monoclonal Antibodies (mAbs) to IL-1α and IL-1β

Cloning and sequencing of the variable heavy (VH) and light (VL) genes of all anti-IL-1α/β mAbs described in Table 1 (above) and additional antibodies were carried out after isolation and purification of the total RNA from the each hybridoma cell line using Trizol reagent (Invitrogen) according to the manufacturer's instructions. Amplification of both VH and VL genes was carried out using the IgGVH and IgκVL oligonucleotides from the Mouse Ig-Primer Set (Novagen, Madison, Wis.) with One-tube RT-PCR kit (Qiagen) as suggested by the manufacturer. DNA fragments resulting from productive amplifications were cloned into pCR-TOPO vector (Invitrogen) according to the manufacturer's instructions. Multiple VH and VL clones were then sequenced by the dideoxy chain termination method using an ABI 3000 sequencer (Applied Biosystems, Foster City, Calif.). The sequences of all mAb VL and VH genes are shown below in Table 2.

TABLE 2

Murine Monoclonal Antibodies Capable Of Binding Human IL-1α Or IL-1β

| Protein | Sequence Identification Number | Sequence 12345678901234567890 |
|---|---|---|
| VH 3D12.E3 | SEQ ID NO: 89 | QIQLVQSGPELKKPGETVKI SCKASGYTFRNYGMNWVKQA PGKDLKRMAWINTYTGESTY ADDFKGRFAFSLETSASTAY LQINNLKNEDTATYFCARGI YYYGSSYAMDYWGQGTSVTV SS |
| VL 3D12.E3 | SEQ ID NO: 90 | NIQMTQTTSSLSASLGDRVT ISCRASQDISNCLNWYQQKP DGTVKLLIYYTSRLHSGVPS RFSGSGSGTDYSLTISNLEQ EDIATYFCQQGKTLPYAFGG GTKLEINR |
| VH 18F4.2C8 | SEQ ID NO: 91 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| VL 18F4.2C8 | SEQ ID NO: 92 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| VH 6H3.1A4.3E11 | SEQ ID NO: 93 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| VL 6H3.1A4.3E11 | SEQ ID NO: 94 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| VH 13F5.G5 | SEQ ID NO: 95 | QVQLQQSGAELVRPGSSVKI SCKASGYAFSSYWMNWVKQR PGQGLEWIGQIYPGDGDTNY NGKFKGKATLTADKSSSTSY MQLSGLTSEDSAMYFCVRFP TGNDYYAMDYWGQGTSVTVS S |
| VL 13F5.G5 | SEQ ID NO: 96 | NIVLTQSPASLAVSLGQRAT ISCRASESVDSYGNSYMHWY QQKPGQPPKLLIYLASNLES GVPARFSGSGSRTDFTLTID PVEADDAATYYCQQNNEDPF TFGSGTKLEIKR |

TABLE 2-continued

Murine Monoclonal Antibodies Capable Of Binding Human IL-1α Or IL-1β

| Protein | Sequence Identification Number | Sequence<br>12345678901234567890 |
|---|---|---|
| VH 1B12.4H4 | SEQ ID NO: 97 | QVHLKESGPGLVAPSQSLSI<br>TCTVSGFSLTDYGVSWIRQP<br>PGKGLEWLGLIWGGGDTYYN<br>SPLKSRLSIRKDNSKSQVFL<br>KMNSLQTDDTAVYYCAKQRT<br>LWGYDLYGMDYWGQGTSVTV<br>SS |
| VL 1B12.4H4 | SEQ ID NO: 98 | ETTVTQSPASLSMAIGEKVT<br>IRCITSTDIDVDMNWYQQKP<br>GEPPKLLISQGNTLRPGVPS<br>RFSSSGSGTDFVFIIENMLS<br>EDVADYYCLQSDNLPLTFGA<br>GTKLELKR |
| VH 6B12.4F6 | SEQ ID NO: 99 | EVQLQQSGPELVKTGTSVKI<br>SCKASGYSFTGYYMHWVRQS<br>HGKSLEWIGYISCYNGFTSY<br>NPKFKGKATFTVDTSSSTAY<br>IQFSRLTSEDSAVYYCARSD<br>YYGTNDYWGQGTTLTVSS |
| VL 6B12.4F6 | SEQ ID NO: 100 | QIVLTQSPAIMSASPGEKVT<br>ITCSASSSVSYMHWFQQKPG<br>ASPKLWIYSTSNLASGVPAR |

TABLE 2-continued

Murine Monoclonal Antibodies Capable Of Binding Human IL-1α Or IL-1β

| Protein | Sequence Identification Number | Sequence<br>12345678901234567890 |
|---|---|---|
| | | FSGSGSGTSYSLTVSRMEAE<br>DAATYYCQQRSTYPYTFGGG<br>TKLEIKR |

Example 1.2

Generation and Characterization of Murine-Human Chimeric Antibodies

All mAbs described above were converted to chimeric antibodies (with human constant region) and expressed, purified, and characterized to confirm activity. The antibodies were also used for controls for subsequent DVD-Ig binding protein analysis. To convert 3D12.E3 into chimeric form, 3D12.E3-VL was PCR amplified using primers P1 and P2; meanwhile human Cκ gene (in pBOS vector generated in-house, Abbott Bioresearch Center, Worcester, Mass.) was amplified using primers P3 and P4. Both PCR reactions were performed according to standard PCR techniques and procedures. The two PCR products were gel-purified, and used together as overlapping template for the subsequent overlapping PCR reaction using primers P1 and P4 using standard PCR conditions. The final PCR product, the chimeric light chain 3D12.E3-VL-hCκ, was subcloned into pEF6 TOPO mammalian expression vector (Invitrogen) by TOPO cloning according to the manufacturer's instructions. Table 3 shows the sequences of each of the PCR primers used in this procedure.

TABLE 3

PCR Primers

| | |
|---|---|
| P1: 5' ATG GTG TCC ACA GCT CAG TTC C 3' | SEQ ID NO: 101 |
| P2: 5' GC AGC CAC CGT ACG CCG GTT TAT TTC CAG 3' | SEQ ID NO: 102 |
| P3: 5' CGT ACG GTG GCT GCA CCA TCT GTC 3' | SEQ ID NO: 103 |
| P4: 5' TCA ACA CTC TCC CCT GTT GAA GC 3' | SEQ ID NO: 104 |

To convert 3D12.E3 heavy chain into chimeric form, 3D12.E3-VH was PCR amplified using primers P5 and P6; meanwhile human Cγ1 gene (in pBOS vector generated in-house at ABC) was amplified using primers P7 and P8. Both PCR reactions were performed according to standard PCR techniques and procedures. The two PCR products were gel-purified, and used together as overlapping template for the subsequent overlapping PCR reaction using primers P5 and P8 using standard PCR conditions. The final PCR product, the chimeric light chain 3D12.E3-VH-hCγ1, was subcloned into pcDNA3.1 TOPO mammalian expression vector (Invitrogen) according to the manufacturer's instructions. Table 4 shows the sequences of each of the PCR primers used in this procedure.

TABLE 4

PCR Primers

| | |
|---|---|
| P5: 5' ATG GCT TGG GTG TGG ACC TTG C 3' | SEQ ID NO: 105 |
| P6: 5' GGG CCC TTG GTC GAC GCT GAG GAG ACG GTG ACT GAG G 3' | SEQ ID NO: 106 |
| P7: 5' GCG TCG ACC AAG GGC CCA TCG GTC TTC C 3' | SEQ ID NO: 107 |
| P8: 5' TC ATT TAC CCG GAG ACA GGG AGA GGC 3' | SEQ ID NO: 108 |

Similarly, chimeric 13F5.G5-VH-Cγ1 was generated using primers P21/P22 (for VH) and P7/P8 (for hCγ1) and cloned into pcDNA3.1 TOPO vector, and chimeric 13F5.G5-VL-Cκ was generated using primers P23/P24 (for VL) and P3/P4 (for hCκ) and cloned into pEF6 TOPO vector. Table 5 shows the sequences of each of the PCR primers used in this procedure.

TABLE 5

| PCR Primers | |
|---|---|
| P21: 5' ATA GAA TGG AGC TGG GTT TTC CTC 3' | SEQ ID NO: 109 |
| P22: 5' GGG CCC TTG GTC GAC GC TGA GGA GAC GGT GAC TGA 3' | SEQ ID NO: 110 |
| P23: 5' ATG GTC CTC ATG TCC TTG CTG TTC 3' | SEQ ID NO: 111 |
| P24: 5' GC AGC CAC CGT ACG CCG TTT TAT TTC CAG CTT TG 3' | SEQ ID NO: 112 |

To express chimeric antibodies, 13F5.G5-VL-Cκ and 13F5.G5-VH-Cγ1 were co-expressed in COS cells using Lipofectamin (Invitrogen) for 72 hours, and the medium collected and IgG purified by Protein A chromatography. Similarly, 13F5.G5-VL-Cκ and 13F5.G5-VH-Cγ1 were co-expressed in COS using Lipofectamin (Invitrogen) for 72 hours, and the medium collected and IgG purified by Protein A chromatography. Both purified chimeric Abs were characterized by Biacore and MRC-5 bioassay to confirm activity. The results showed that these chimeric Abs displayed similar affinity and potency to that of the original murine mAbs.

Example 1.3

Figures 1A, 1B:
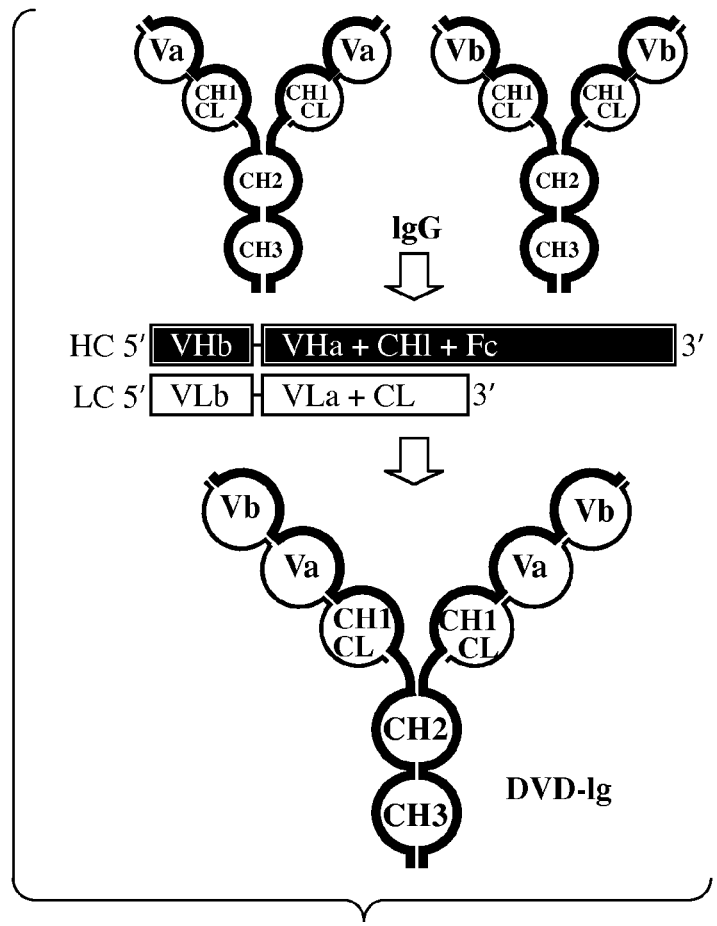
FIG. 1A is a schematic representation of Dual Variable Domain Immunoglobulin (DVD-Ig) constructs and shows the strategy for generating a DVD-Ig molecule from two parent antibodies.
FIG. 1B shows schematic representations of genetic constructs for DVD1-Ig, DVD2-Ig, and two chimeric, monospecific, monoclonal antibodies 2D13.E3 (anti-IL-1α) and 13F5.G5 (anti-IL-1β). "VHβ" and "VLβ" indicate, respectively, a heavy chain variable domain and a light chain variable domain of an antigen binding site of the 13F5.G5 antibody that binds IL-β. "VHα" and "VLα" indicate, respectively, a heavy chain variable domain and a light chain variable domain of the 3D12.E3 antibody that binds IL-1α. "L" indicates a leader sequence. In diagram of genetic construct for DVD2-Ig, horizontal markings between "VHβ" and "VHα" and between "VLβ" and "VLα" indicate presence of a linker sequence.

Construction, Expression, and Purification of IL-1α/β Dual Variable Domain Immunoglobulin (DVD-Ig) Molecule The construct used to generate DVD-Ig binding protein capable of binding hIL-1α and hIL-1β is illustrated in FIG. 1B. Briefly, parent mAbs including two high affinity murine antibodies, anti-hIL-1α (clone 3D12.E3) and anti-hIL-1β (clone 13F5.G5), were obtained by immunizing Balb/c mice with recombinant IL-1α protein (rhIL-1α) and recombinant IL-1β protein (rhIL-1β), respectively. The VL/VH genes of these two hybridoma clones were isolated by RT-PCR using the mouse Ig Primer Kit (Novagen, Madison, Wis.). The VL/VH genes were first converted into chimeric antibodies (with human constant regions) to confirm activity and potency. To generate DVD1-Ig binding protein, the VH and VL of 13F5.G5 was directly fused to the N-terminus of the VH and VL of 3D12.E3, respectively (as shown in FIG. 1B). The DVD2-Ig binding protein was constructed similarly, except that it had a linker between the two variable domains in both the light chain (the linker sequence is ADAAP) and the heavy chain (the linker sequence is AKTTPP). These sequences were selected from the N-termini of murine Ck and CH1 sequences. These linker sequences, selected from the N-termini of murine Ck and CH1, are natural extension of the variable domains and exhibit a flexible conformation without significant secondary structures based on the analysis of several Fab crystal structures. The detailed procedures of the PCR cloning are described below.

Example 1.3.A

Molecular Cloning of hIl-1α/β DVD1-Ig Binding Protein

13F5.G5-VH was PCR amplified using primers P21 and P25. 3D12.E3-VH-hCγ1 was amplified using primers P14 and P8. Both PCR reactions were performed according to standard PCR techniques and procedures. The two PCR products were gel-purified, and used together as overlapping template for the subsequent overlapping PCR reaction using primers P21 and P8 using standard PCR conditions. The final PCR product, the DVD1-Ig heavy chain hIL-1α/βDVD1-VH-hCγ1, was subcloned into pcDNA3.1 TOPO mammalian expression vector (Invitrogen) according to the manufacturer's instructions. Table 6 shows the sequences of the PCR primers used in this procedure.

TABLE 6

| PCR Primers | |
|---|---|
| P14: 5' CAG ATC CAG TTG GTG CAG TCT GG3' | SEQ ID NO: 113 |
| P25: 5' CAC CAA CTG GAT CTG TGA GGA GAC GGT GAC TGA GG 3' | SEQ ID NO: 114 |

To generate hIL-1α/βDVD1-Ig light chain, 13F5.G5-VL was PCR amplified using primers P23 and P26; meanwhile 3D12.E3-VL-hCκ was amplified using primers P16 and P4. Both PCR reactions were performed according to standard PCR techniques and procedures. The two PCR products were gel-purified, and used together as overlapping template for the subsequent overlapping PCR reaction using primers P23 and P4 using standard PCR conditions. The final PCR product, the hIL-1α/β DVD1-Ig light chain hIL-1α/βDVD1-VL-hCκ, was subcloned into pEF6 TOPO mammalian expression vector (Invitrogen) according to the manufacturer's instructions. Table 7 shows the sequences of each of the PCR primers used in this procedure.

TABLE 7

| PCR Primers | |
|---|---|
| P16: 5' AAT ATC CAG ATG ACA CAG ACT ACA TCC 3' | SEQ ID NO: 115 |
| P26: 5' GTGT CAT CTG GAT ATT CCG TTT TAT TTC CAG CTT TG 3' | SEQ ID NO: 116 |

Example 1.3.B

Molecular cloning of hIL-1α/β DVD2-Ig

13F5.G5-VH was PCR amplified using primers P21 and P17. 3D12.E3-VH-hCγ1 was amplified using primers P18 and P8. Both PCR reactions were performed according to standard PCR techniques and procedures. The two PCR products were gel-purified, and used together as overlapping template for the subsequent overlapping PCR reaction using primers P21 and P8 using standard PCR conditions. The final PCR product, the DVD2-Ig heavy chain hIL-1α/βDVD2-VH-hCγ1, was subcloned into pcDNA3.1 TOPO mammalian expression vector (Invitrogen) according to the manufacturer's instructions. Table 8 shows the sequences of each of the PCR primers used in this procedure.

TABLE 8

| PCR Primers | |
|---|---|
| P17: 5' TGG GGG TGT CGT TTT GGC TGA GG 3' | SEQ ID NO: 117 |
| P18: 5' GCC AAA ACG ACA CCC CCA CAG ATC CAG TTG GTG CAG 3' | SEQ ID NO: 118 |

To generate hIL-1α/βDVD2-Ig light chain, 13F5.G5-VL was PCR amplified using primers P23 and P19. 3D12.E3-VL-hCκ was amplified using primers P20 and P4. Both PCR reactions were performed according to standard PCR techniques and procedures. The two PCR products were gel-purified, and used together as overlapping template for the subsequent overlapping PCR reaction using primers P23 and P4 using standard PCR conditions. The final PCR product, the hIL-1α/βDVD2-Ig light chain hIL-1α/βDVD2-VL-hCκ, was subcloned into pEF6 TOPO mammalian expression vector (Invitrogen) according to the manufacturer's instructions. Table 9 shows the sequences of each of the PCR primers used in this procedure.

TABLE 9

| PCR Primers | |
|---|---|
| P19: 5' TGG TGC AGC ATC AGC CCG TTT TAT TTC 3' | SEQ ID NO: 119 |
| P20: 5' GCT GAT GCT GCA CCA AAT ATC CAG ATG ACA CAG 3' | SEQ ID NO: 120 |

The final sequences of hIL-1α/βDVD1-Ig and hIL-1α/βDVD2-Ig are described in Table 10.

TABLE 10

Amino Acid Sequence of hII-1α/β DVD1-Ig and hII-1α/β DVD2-Ig Binding Protein

| Protein region | Sequence Identifier | Sequence 12345678901234567890 |
|---|---|---|
| DVD-Ig HEAVY | SEQ ID NO: 121 | QVQLQQSGAELVRPGSSVKI SCKASGYAFSSYWMNWVKQR |

TABLE 10-continued

Amino Acid Sequence of hII-1α/β DVD1-Ig and hII-1α/β DVD2-Ig Binding Protein

| Protein region | Sequence Identifier | Sequence 12345678901234567890 |
|---|---|---|
| VARIABLE hIL-1α/β DVD1-Ig | | PGQGLEWIGQIYPGDGDTNY NGKFKGKATLTADKSSSTSY MQLSGLTSEDSAMYFCVRFP TGNDYYAMDYWGQGTSVTVS SQIQLVQSGPELKKPGETVK ISCKASGYTFRNYGMNWVKQ APGKDLKRMAWINTYTGEST YADDFKGRFAFSLETSASTA YLQINNLKNEDTATYFCARG |

TABLE 10-continued

Amino Acid Sequence of hII-1α/β DVD1-Ig and hII-1α/β DVD2-Ig Binding Protein

| Protein region | Sequence Identifier | Sequence 12345678901234567890 |
|---|---|---|
| | | IYYYGSSYAMDYWGQGTSVT VSS |
| VH 13F5.G5 | SEQ ID NO: 95 | QVQLQQSGAELVRPGSSVKI SCKASGYAFSSYWMNWVKQR |

TABLE 10-continued

Amino Acid Sequence of hII-1α/β DVD1-Ig and hII-1α/β DVD2-Ig Binding Protein

| Protein region | Sequence Identifier | Sequence 12345678901234567890 |
|---|---|---|
| | | PGQGLEWIGQIYPGDGDTNY NGKFKGKATLTADKSSSTSY MQLSGLTSEDSAMYFCVRFP |

TABLE 10-continued

Amino Acid Sequence of hIl-1α/β DVD1-Ig and hIl-1α/β DVD2-Ig Binding Protein

| Protein region | Sequence Identifier | Sequence |
|---|---|---|
| | | TGNDYYAMDYWGQGTSVTVSS |
| Linker | | None |
| 3D12.E3 VH | SEQ ID NO: 89 | QIQLVQSGPELKKPGETVKISCKASGYTFRNYGMNWVKQAPGKDLKRMAWINTYTGESTYADDFKGRFAFSLETSASTAYLQINNLKNEDTATYFCARGIYYYGSSYAMDYWGQGTSVTVSS |
| CH | SEQ ID NO: 122 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DVD-Ig LIGHT VARIABLE hIL-1α/β DVD1-Ig | SEQ ID NO: 123 | NIVLTQSPASLAVSLGQRATISCRASESVDSYGNSYMHWYQQKPGQPPKLLIYLASNLESGVPARFSGSGSRTDFTLTIDPVEADDAATYYCQQNNEDPFTFGSGTKLEIKRNIQMTQTTSSLSASLGDRVTISCRASQDISNCLNWYQQKPDGTVKLLIYYTSRLHSGVPSRFSGSGSGTDYSLTISNLEQEDIATYFCQQGKTLPYAFGGGTKLEINRR |
| 13F5.G5 VL | SEQ ID NO: 96 | NIVLTQSPASLAVSLGQRATISCRASESVDSYGNSYMHWYQQKPGQPPKLLIYLASNLESGVPARFSGSGSRTDFTLTIDPVEADDAATYYCQQNNEDPFTFGSGTKLEIKR |
| Linker | | None |
| 3D12.E3 VL | SEQ ID NO: 90 | NIQMTQTTSSLSASLGDRVTISCRASQDISNCLNWYQQKPDGTVKLLIYYTSRLHSGVPSRFSGSGSGTDYSLTISNLEQEDIATYFCQQGKTLPYAFGGGTKLEINR |
| CL | SEQ ID NO: 124 | TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| DVD-Ig HEAVY VARIABLE hIL-1α/β DVD2-Ig | SEQ ID NO: 125 | QVQLQQSGAELVRPGSSVKISCKASGYAFSSYWMNWVKQRPGQGLEWIGQIYPDGDTNYNGKFKGKATLTADKSSSTSYMQLSGLTSEDSAMYFCVRFPTGNDYYAMDYWGQGTSVTVSSAKTTPPQIQLVQSGPELKKPGETVKISCKASGYTFRNYGMNWVKQAPGKDLKRMAWINTYTGESTYADDFKGRFAFSLETSASTAYLQINNLKNEDTATYFCARGIYYYGSSYAMDYWGQGTSVTVSS |
| 13F5.G5 VH | SEQ ID NO: 95 | QVQLQQSGAELVRPGSSVKISCKASGYAFSSYWMNWVKQRPGQGLEWIGQIYPDGDTNYNGKFKGKATLTADKSSSTSYMQLSGLTSEDSAMYFCVRFPTGNDYYAMDYWGQGTSVTVSS |
| Linker | SEQ ID NO: 75 | AKTTPP |
| 3D12.E3 VH | SEQ ID NO: 89 | QIQLVQSGPELKKPGETVKISCKASGYTFRNYGMNWVKQAPGKDLKRMAWINTYTGESTYADDFKGRFAFSLETSASTAYLQINNLKNEDTATYFCARGIYYYGSSYAMDYWGQGTSVTVSS |
| CH | SEQ ID NO: 122 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DVD-Ig LIGHT VARIABLE HIL-1α/β DVD2-Ig | SEQ ID NO: 126 | NIVLTQSPASLAVSLGQRATISCRASESVDSYGNSYMHWYQQKPGQPPKLLIYLASNLESGVPARFSGSGSRTDFTLTIDPVEADDAATYYCQQNNEDPFTFGSGTKLEIKRADAAPNIQMTQTTSSLSASLGDRVTISCRASQDISNCLNWYQQKPDGTVKLLIYYTSRLHSGVPSRFSGSGSGTDYSLTISNLEQEDIATYFCQQGKTLPYAFGGGTKLEINR |
| 13F5.G5 VL | SEQ ID NO: 96 | NIVLTQSPASLAVSLGQRATISCRASESVDSYGNSYMHWYQQKPGQPPKLLIYLASNLESGVPARFSGSGSRTDFTLTIDPVEADDAATYYCQQNNEDPFTFGSGTKLEIKR |
| Linker | SEQ ID NO: 69 | ADAAP |
| 3D12.E3 VL | SEQ ID NO: 90 | NIQMTQTTSSLSASLGDRVTISCRASQDISNCLNWYQQKPDGTVKLLIYYTSRLHSGVPSRFSGSGSGTDYSLTISNLEQEDIATYFCQQGKTLPYAFGGGTKLEINR |

TABLE 10-continued

Amino Acid Sequence of hII-1α/β DVD1-Ig and
hII-1α/β DVD2-Ig Binding Protein

| Protein<br>Protein<br>region | Sequence<br>Identifier | Sequence<br>12345678901234567890 |
|---|---|---|
| CL | SEQ ID NO: 124 | TVAAPSVFIFPPSDEQLKSG<br>TASVVCLLNNFYPREAKVQW<br>KVDNALQSGNSQESVTEQDS<br>KDSTYSLSSTLTLSKADYEK<br>HKVYACEVTHQGLSSPVTKS<br>FNRGEC |

Example 1.3.C

Expression and Purification of hIL-1α/βDVD1-Ig Binding Protein

The heavy and light chain of each construct was subcloned into pcDNA3.1 TOPO and pEF6 TOPO vectors (Invitrogen Inc.), respectively, and sequenced to ensure accuracy. The plasmids encoding the heavy and light chains of each construct were transiently expressed using Lipofectamine 2000 and 293fectin reagents, respectively in COS cells as well as human embryonic kidney 293 cells (American Type Culture Collection, Manassas, Va.). The cell culture media were harvested 72 hour-post transient transfection and antibodies purified using protein A chromatography (Pierce, Rockford, Ill.) according to manufacturer's instructions. The antibodies were analyzed by SDS-PAGE and quantitated by A280 and BCA (Pierce, Rockford, Ill.). Table 11 shows that the expression levels of hIL-1α/βDVD1-Ig and hIL-1α/βDVD2-Ig are comparable to that of the chimeric antibodies, indicating that the DVD-Ig binding protein can be expressed efficiently in mammalian cells.

TABLE 11

Expression and Molecular Weight Analysis of hIL-1α/β DVD-Ig Binding Protein

| | Expression | | Molecular Mass (Dalton) | | |
|---|---|---|---|---|---|
| | Level (ng/ml) | | Light | Heavy | Full |
| | COS | Freestyle 293 | Chain | Chain | length |
| Mock | 0 | 0 | | | |
| 3D12.E3-Ch | 2788 | 3886 | 23,696 | 49,914 | 147,220 |
| 13F5.G5-Ch | 3260 | 3562 | 24,084 | 49,518 | 147,204 |
| DVD1-Ig | 2988 | 3300 | 35,797<br>(35,790) | 64,380<br>(64,371) | 200,346<br>(200,521) |
| DVD2-Ig | 2433 | 3486 | 36,222<br>(36,220) | 64,976<br>(64,973) | 202,354<br>(202,573) |

The molecular mass of the light chain, heavy chain, and full length of DVD1-Ig binding protein and DVD2-Ig binding protein determined experimentally by mass spectrometry are shown in parenthesis.

Example 1.4

Mass Spectrometry and SEC Analysis of hIL-1α/βDVD-Ig Binding Protein

For measuring molecular weight (MW) of light and heavy chains of DVD-Ig binding protein, 10 μL of DVD-Ig molecule (0.8 μg/μL) was reduced by 1.0 M DTT solution (5 μL). A PLRP-S, 8μ, 4000 A, and 1×150 mm protein column (Michrom BioResource, Auburn, Mass.) was used to separate heavy and light chains of DVD-Ig molecule. Agilent HP1100 Capillary HPLC (Agilent Technologies Inc., Pala Alto, Calif.) was used with the mass spectrometer QSTAR (Applied Biosystems, Foster City, Calif.). The valco valve was set at 10 minutes to switch the flow from waste to MS for desalting sample. Buffer A was 0.02% TFA, 0.08% FA, 0.1% ACN and 99.8% HPLC-H2O. Buffer B contained 0.02% TFA, 0.08% FA, 0.1% HPLC-H$_2$O, and 99.8% ACN. The HPLC flow rate was 50 μL/minute and the sample injection volume was 8.0 mL. The temperature of the column oven was set at 60° C., and separation gradient was: 5% B for 5 minutes; 5% B to 65% B for 35 minutes; 65% B to 95% B for another 5 minutes, and 95% B to 5% B for 5 minutes. TOFMS scan was from 800 to 2500 amu, and cycles were 3600. To determine the MW of full length DVD-Ig binding protein, a Protein MicroTrap cartridge (Michrom BioResource, Auburn, Mass.) was used for desalting the sample. The HPLC gradient was: 5% B for 5 minutes; 5% B to 95% B in 1 minute; and from 95% B to 5% B in another 4 minutes. The QSTAR TOFMS scan was from 2000 to 3500 amu, and cycles were 899. All MS raw data were analyzed using the Analyst QS software (Applied Biosystems). For SEC analysis of the DVD-Ig binding protein, purified DVD-Ig binding protein and chimeric Abs, in PBS, were applied on a Superose 6 10/300 G2, 300×10 mm column (Amersham Bioscience, Piscataway, N.J.). An HPLC instrument, Model 10A (Shimadzu, Columbia, Md.) was used for SEC. All proteins were determined using UV detection at 280 nm and 214 nm. The elution was isocratic at a flow rate of 0.5 mL/minute. For stability study, samples in the concentration range of 0.2-0.4 mg/ml in PBS underwent 3 freeze-thaw cycles between −80° C. and 25° C., or were incubated at 4° C., 25° C., or 40° C., for 4 weeks and 8 weeks, followed by SEC analysis.

DVD-Ig binding protein and chimeric antibodies were purified by protein A chromatography. The purification yield (3-5 mg/L) was consistent with hIgG quantification of the expression medium for each protein. The composition and purity of the purified DVD-Ig binding proteins and chimeric antibodies were analyzed by SDS-PAGE in both reduced and non-reduced conditions. In non-reduced condition, each of the four proteins migrated as a single band. The DVD-Ig proteins showed greater molecular weight than the chimeric antibodies, as expected. In non-reducing condition, each of the four proteins yielded two bands, one heavy chain and one light chain. Again, the heavy and light chains of the DVD-Ig binding proteins were larger in size than that of the chimeric antibodies. The SDS-PAGE showed that each DVD-Ig binding protein is expressed as a single species, and the heavy and light chains are efficiently paired to form an IgG-like molecule. The sizes of the heavy and light chains as well as the full-length protein of two DVD-Ig molecules are consistent with their calculated molecular mass based on amino acid sequences (see Table 11).

In order to determine the precise molecular weight of the DVD-Ig binding proteins, mass spectrometry was employed. As shown in Table 1, the experimentally determined molecular mass of each DVD-Ig binding protein, including the light chain, heavy chain, and the full-length protein, is in good agreement with the predicted value. To further study the physical properties of DVD-Ig binding protein in solution, size exclusion chromatography (SEC) was used to analyze each protein. Both chimeric Abs and DVD2-Ig binding protein exhibited a single peak, demonstrating physical homogeneity as monomeric proteins. The 3D12.E3 chimeric Ab showed a smaller physical size then 13F5.G5 chimeric Ab, indicating that 3D12.E3 chimeric Ab adopted a more compact, globular shape. DVD1-Ig binding protein revealed a major peak as well as a shoulder peak on the right, suggesting that a portion of DVD1-Ig binding protein is possibly in an aggregated form in current buffer condition.

Example 1.5

Analysis of In Vitro Stability of hIL-1α/β DVD-Ig Binding Proteins

The physical stability of DVD-Ig was tested as follows. Purified antibodies in the concentration range of 0.2-0.4 mg/ml in PBS underwent 3 freeze-thaw cycles between −80° C. and 25° C., or were incubated at 4° C., 25° C., or 40° C., for 4 weeks and 8 weeks, followed by analysis using size exclusion chromatography (SEC) analysis (see Table 12).

TABLE 12

In Vitro Stability Analysis of hIl-1α/β DVD-Ig by SEC

|  | 3D12.E3-Ch | | | 13F5.G5-Ch | | | DVD1-Ig | | | DVD2-Ig | | |
| --- | --- | --- | --- | --- | --- | --- | --- | --- | --- | --- | --- | --- |
|  | Agg | Ab | Frgm | Agg | Ab | Frgm | Agg | Ab | Frgm | Agg | Ab | Frgm |
| 3xFreeze-Thaw | 1.72 | 98.28 | 0.00 | 13.0 | 87.0 | 0.0 | 46.50 | 53.50 | 0.00 | 0.0 | 100.0 | 0.0 |
| 4° C. @ 4 Wks | 0.85 | 99.15 | 0.00 | 4.2 | 95.8 | 0.0 | 42.43 | 56.63 | 0.94 | 0.0 | 100.0 | 0.0 |
| 25° C. @ 4 Wks | 1.29 | 98.71 | 0.00 | 0.0 | 100.0 | 0.0 | 45.66 | 54.34 | 0.00 | 0.0 | 100.0 | 0.0 |
| 40° C. @ 4 Wks | 1.65 | 98.35 | 0.00 | 20.3 | 78.1 | 1.6 | 36.70 | 59.42 | 3.88 | 0.0 | 100.0 | 0.0 |
| 4° C. @ 8 Wks | 5.35 | 90.33 | 4.32 | 2.2 | 97.8 | 0.0 | 38.18 | 56.91 | 4.91 | 0.0 | 100.0 | 0.0 |
| 25° C. @ 8 Wks | 1.11 | 60.55 | 38.34 | 1.4 | 97.5 | 1.0 | 24.42 | 67.39 | 8.19 | 0.0 | 100.0 | 0.0 |
| 40° C. @ 8 Wks | 4.74 | 81.47 | 13.79 | 34.6 | 65.4 | 0.0 | 20.55 | 67.16 | 12.29 | 0.0 | 100.0 | 0.0 |

The degree of aggregation and fragmentation are shown in percentage, whereas the percentage of Ab represents intact molecule.
Agg: aggregates;
Ab: intact antibody;
Frgm: fragments.

Both chimeric antibodies showed minor degrees of aggregation and fragmentation, normal for a regular IgG molecule. DVD1-Ig binding protein showed some aggregation on SEC after purification. In the stability analysis, DVD1-Ig binding protein also showed aggregations in PBS under different conditions; however the percentage of aggregated form of DVD1-Ig binding protein did not increase during prolonged storage or at higher temperatures. The percentage of the fragmented form of DVD1-Ig binding protein was in the normal range, similar to that of the chimeric 3D12.E3 Ab. In contrast, DVD2-Ig binding protein showed exceptional stability. Neither aggregation nor fragmentation was detected for DVD2-Ig binding protein in all conditions tested, and 100% of DVD2-Ig binding protein maintained as intact monomeric molecule.

Example 1.6

Determination of Antigen Binding Affinity of hIL-1α/β DVD-Ig Binding Proteins The kinetics of DVD-Ig molecules binding to rhIL1-α and rhIL1-β was determined by surface plasmon resonance-based measurements with a Biacore 3000 instrument (Biacore AB, Uppsala, Sweden) using HBS-EP (10 mM HEPES, pH 7.4, 150 mM NaCl, 3 mM EDTA, and 0.005% surfactant P20) at 25° C. All chemicals were obtained from Biacore AB (Uppsala, Sweden) or otherwise from a different source as described herein. Approximately, 5000 RU of goat anti-human IgG Fcγ fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 mg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-human IgG in flow cell 1 and 3 was used as the reference surface. For kinetic analysis, rate equations derived from the 1:1 Langmuir binding model were fitted simultaneously to association and dissociation phases of all ten injections (using global fit analysis) using the Bioevaluation 4.0.1 software. Purified DVD-Ig samples were diluted in HEPES-buffered saline for capture across goat anti-human IgG Fc specific reaction surfaces and injected over reaction matrices at a flow rate of 5 ml/minute. The association and dissociation rate constants, kon (M-1s-1) and koff (s-1) were determined under a continuous flow rate of 25 ml/minute. Rate constants were derived by making kinetic binding measurements at ten different antigen concentrations ranging from 1.25 to 1000 nM. The equilibrium dissociation constant (M) of the reaction between DVD-Ig molecule and rhIL1α/β was then calculated from the kinetic rate constants by the following formula: KD=koff/kon. Aliquots of rhIL1α/β samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 5 ml/minute. The anti-Fc antibody immobilized surfaces were completely regenerated and retained their full capture capacity over twelve cycles. The apparent stoichiometry of the captured DVD-Ig-rhIL1α/β complex was calculated under saturating binding conditions (steady-state equilibrium) using the following formula:

$$\text{Stoichiometry} = \frac{rhIL1\,\alpha/\beta\,\text{response }(RU)}{DVD\,\text{response }(RU)} \times \frac{DVD\text{-}Ig\,(MW)}{rhIL1\,\alpha/\beta\,(MW)}$$

The Biacore analysis indicated the chimeric antibodies possessed similar binding kinetics and affinities to IL-1 as the original hybridoma monoclonal antibodies, indicating that the correct VL/VH sequences had been isolated (Table 13). The overall binding parameters of the two DVD-Ig binding proteins to hIL-1α were similar, with the affinities of the DVD-Ig binding proteins being only 2-3 fold less than that of the chimeric 3D12.E3 antibody. The binding affinity of DVD2-Ig binding protein to hIL-1β was slightly less than the chimeric antibody 13F5.G5, but 3-fold higher than that of DVD1-Ig binding protein. The affinity of the two DVD-Ig binding proteins to hIL-1 as compared to the affinity of chimeric antibodies to hIL-1 was similar as indicated by the evaluation of the stoichiometry to IL-1. Both chimeric antibodies, being bivalent monospecific, bound to IL-1α and IL-1β on Biacore with a stoichiometry of 1.6 and 1.7, respectively. This is common for an IgG due to inter-molecular interference when antibodies are immobilized densely on the Biacore sense chip resulting in stoichiometry being in the range from 1.5 to 2.0. The stoichiometries of both DVD-Ig binding proteins for hIL-1α and hIL-1β were similar to that of the two chimeric antibodies, indicating that both DVD-Ig binding proteins possessed bivalent binding capability to each antigen.

TABLE 13

Functional Characterization of IL-1 Binding Proteins

| IL-1 Binding Protein | Antigen | $k_{on}$ (M−1 s−1) | $k_{off}$ (s−1) | $K_d$ (M) | Stoichiometry | Potency $IC_{50}$ (M) |
|---|---|---|---|---|---|---|
| 3D13.E3 | hIL-1α | $6.43 \times 10^{+5}$ | $7.13 \times 10^{-4}$ | $1.11 \times 10^{-9}$ | 2.0 | $6.70 \times 10^{-10}$ |
| 3D12.E3-Ch | hIL-1α | $4.12 \times 10^{+5}$ | $5.52 \times 10^{-4}$ | $1.34 \times 10^{-9}$ | 1.6 | $7.00 \times 10^{-10}$ |
| DVD1-Ig | hIL-1α | $3.70 \times 10^{+4}$ | $1.05 \times 10^{-4}$ | $2.83 \times 10^{-9}$ | 1.8 | $2.30 \times 10^{-9}$ |
| DVD2-Ig | hIL-1α | $7.35 \times 10^{+4}$ | $2.52 \times 10^{-4}$ | $3.42 \times 10^{-9}$ | 2.0 | $2.90 \times 10^{-9}$ |
| 13F5.G5 | hIL-1β | $2.13 \times 10^{+6}$ | $6.21 \times 10^{-4}$ | $2.91 \times 10^{-10}$ | 1.8 | $6.00 \times 10^{-10}$ |
| 13F5.G5-Ch | hIL-1β | $1.41 \times 10^{+6}$ | $6.54 \times 10^{-4}$ | $4.62 \times 10^{-10}$ | 1.7 | $5.30 \times 10^{-10}$ |
| DVD1-Ig | hIL-1β | $6.09 \times 10^{+5}$ | $1.59 \times 10^{-3}$ | $2.60 \times 10^{-9}$ | 1.5 | $3.10 \times 10^{-9}$ |
| DVD2-Ig | hIL-1β | $1.19 \times 10^{+6}$ | $9.50 \times 10^{-4}$ | $7.98 \times 10^{-10}$ | 1.8 | $1.60 \times 10^{-9}$ |

Affinity and stoichiometry were measured by Biacore;
Potency ($IC_{50}$) was determined by MRC-5 bioassay;
Ch = chimeric In addition, tetravalent dual-specific antigen binding of DVD-Ig binding protein was also analyzed by Biacore (Table 14). DVD-Ig binding protein was first captured via a goat anti-human Fc antibody on the Biacore sensor chip, and the first antigen was injected and a binding signal observed. As the DVD-Ig binding protein was saturated by the first antigen, the second antigen was then injected and the second signal observed. This was done either by first injecting IL-1β then IL-1α or by first injecting IL-1α followed by IL-1β for DVD2-Ig binding protein. In either sequence, a dual-binding activity was detected. Similar results were obtained for DVD1-Ig binding protein. Thus, each DVD-Ig binding protein was able to bind both antigens simultaneously as a dual-specific tetravalent molecule. As shown in Table 14, the stoichiometry of both DVD-Ig binding protein to the first antigen, either hIL-1α or hIL-1β, were larger than 1.5, similar to that of mono-specific bivalent binding. Upon the injection of the second antigen, while DVD-Ig binding protein was already occupied by the first antigen, the stoichiometry of both DVD-Igs binding protein to the second antigen (i.e., hIL-1α or hIL-1β was between 1.0 and 1.3. Thus, DVD-Ig binding protein was able to bind two IL-1α and two IL-β molecules. DVD-Ig binding protein was first captured via a goat anti-human Fc antibody on the Biacore sensor chip, and the first antigen was injected and a binding signal observed, followed by the injection of the second antigen.

TABLE 14

Stoichiometry Analysis of hIL-1α/β DVD-Ig Binding Protein in Tetravalent Dual-Specific Binding to IL-1α/β

| Captured Binding Protein | Response Unit | | Stoichiometry | |
|---|---|---|---|---|
| | 1st antigen | 2nd antigen | hIL-1α:DVD-Ig | hIL-1β:DVD-Ig |
| DVD1-Ig: 932 | hIL-1α: 190 | hIL-1β: 75 | 2.3 | 1.0 |
| DVD1-Ig: 1092 | hIL-1β: 141 | hIL-1α: 107 | 1.1 | 1.5 |
| DVD2-Ig: 1324 | hIL-1α: 209 | hIL-1β: 137 | 1.8 | 1.3 |
| DVD2-Ig: 1184 | hIL-1β: 159 | hIL-1α: 131 | 1.2 | 1.6 |

Example 1.7

Determination of Functional Homogeneity of DVD-Ig Molecules

Because DVD2-Ig binding protein was purified by Protein A chromatography instead of target-specific affinity chromatography, any potential misfolded and/or mismatched VL/VH domains, if present, can be assessed by binding studies against the two different antigens. Such binding analysis was conduced by size exclusion liquid chromatography (SEC). DVD2-Ig binding protein, alone or after a 120-minute incubation period at 37° C. with IL-1α, IL-1β, or both IL-1α and IL-1β, in equal molar ratio, were applied to the column. Each of the antigens was also run alone as controls. The SEC results indicated that DVD2-Ig binding protein was able to bind IL-1α and IL-1β in solution, and such binding resulted in a shift to the SEC signal indicating an increase in the dynamic size of DVD2-Ig binding protein when it was in complex with either antigen. The shift of the DVD2-Ig binding protein signal was 100%, not partial, suggesting all DVD2-Ig molecules were able to bind the antigen. In the presence of both IL-1α and IL-1β, there was a further and complete shift of the DVD2-Ig binding protein signal, indicating all DVD2-Ig molecules were able to bind both antigens in a uniform fashion. This experiment demonstrated that DVD-Ig binding protein was expressed as a functionally homogeneous protein. This has significant implications as it demonstrates that DVD-Ig binding protein can be produced as a homogeneous single, functional species, which differs from all previously described bi-specific, multi-specific, and multi-valent immunoglobulin-like and immunoglobulin-derived molecules.

Example 1.8

Determination of Biological Activity of DVD-Ig Binding Proteins

The biological activity of DVD-Ig was measured using MRC-5 bioassay. The MRC-5 cell line is a human lung fibroblast cell line that produces IL-8 in response to human IL-1α and IL-1β in a dose-dependent manner. MRC-5 cells were obtained from ATCC and cultured in 10% FBS complete MEM at 37° C. in a 5% $CO_2$ incubator. To determine neutralizing activity of the DVD-Ig against human IL-1α or IL-1β, 50 μl of antibody ($1\times10^{-7}$ to $1\times10^{-12}$ M) in MEM/10% FBS was added to a 96 well plate and pre-incubated with 50 μl of hIL-1α or hIL-1β (200 pg/ml) for 1 hour at 37° C., 5% $CO_2$. MRC-5 cells at a concentration of $1\times10^5$/ml were then added (100 μl) to all wells, and the plates were incubated overnight at 37° C. in a 5% $CO_2$ incubator. The supernatants were harvested and human IL-8 production measured by standard ELISA (R&D Systems, Minneapolis, Minn.). Neutralizing activity of the DVD-Ig binding protein was determined by its ability to inhibit IL-8 production.

As shown in Table 13, both DVD-Ig binding proteins were able to neutralize hIL-1α and hIL-1β. Consistent with the binding affinity to hIL-1α, the neutralizing activities of DVD1-Ig binding protein and DVD2-Ig binding protein against hIL-1α were also similar, i.e., 3-fold less than that of the chimeric antibodies (see, Table 13). Consistent with its binding affinity for hIL-1β, the neutralizing activity of DVD2-Ig binding protein to hIL-1β is slightly less than that of the chimeric Ab 13F5.G5, but 3-fold higher than that of DVD1-Ig binding protein. Overall there was no significant decrease in the biological activities of DVD-Ig molecules compared to the original monoclonal antibodies.

To determine if DVD-Ig binding protein was able to inhibit IL-8 production in the presence of both IL-1α and IL-1β, equal amounts of hIL-1α and hIL-1β were added in the same culture system of MRC-5 assay. Both the DVD1-Ig binding protein and the DVD2-Ig binding protein were able to inhibit IL-8 synthesis by MRC-5 cells in the presence of both IL-1α and IL-1β, with activities similar to that of mono-assays where only one cytokine was present (Table 13). In this assay where both IL-1α and IL-1β were present, the dual-inhibition activity of DVD2-Ig binding protein (1.2 nM) was higher than that of DVD1-Ig binding protein (2.2 nM).

Example 2

Analysis of Linker Size and Variable Domain Orientation in DVD-Ig Binding Proteins Additional DVD-Ig molecules with different parent mAb pairs, as shown in Table 15, were constructed. For each pair of mAbs, four different DVD-Ig constructs were generated: 2 with a short linker and 2 with a long linker, each in two different domain orientations: a-b-C (alpha-beta-constant domain) and b-a-C (beta-alpha-constant domain). The linker sequences were derived from the N-terminal sequence of human Ck or CH1 domain, as follows: Short linker: light chain: TVAAP (SEQ ID NO:71); heavy chain: ASTKGP (SEQ ID NO:79); and Long linker: light chain: TVAAPSVFIFPP (SEQ ID NO:72); heavy chain: ASTKGPSVFPLAP (SEQ ID NO:80).

All heavy and light chain constructs were subcloned into the pBOS expression vector, and expressed in COS cells or freestyle 293 cells.

To construct new DVD-Ig clones, the variable domains of the two mAbs, both light chain and heavy chain, were first jointed in tandem using overlapping PCR as described for hIL-1α/βDVD1-Ig and hIL-1α/βDVD2-Ig. The jointed pieces were then subcloned in pBOS vector using homologous recombination. Briefly, vectors were linearized by restriction digestion (2 μg of pBOS-hCk vector were digested with FspAI and BsiWI in O+ buffer, and 2 μg of pBOS-hCγz, non a vector was digested with FspAI and SalI in O+ buffer). The digested samples were run on a 1% agarose gel and the backbone fragment purified in 50 μl water. For homologous recombination and transformation, DH5α competent cells were thaw on ice, and mixed with 20-50 ng jointed PCR product and 20-50 ng of linearized vector (in every 50 μl DH5α cells). The mixture was mixed gently and incubated on ice for 45 minutes, followed by heat shock at 42° C. for 1 minute. Then 100 μl SOC medium were added and incubated at 37° C. for 1 hour. The transformation culture was inoculated on LB/agar plates containing ampicillin and incubated at 37° C. for 18-20 hours. The bacterial clones were isolated, from which DNA was purified and subjected to sequencing analysis. The final sequence-verified clones were co-transfected (matching HV and LC of the same antibody pair) in COS or 293 cells for antibody expression and purification, as previously described.

Characteristics of the purified DVD-Ig proteins are summarized in Table 16. The left section of the Table 16 shows the specificity, binding affinity, and neutralization potency of the 2 pairs of mAbs used for the construction of the new hIL-1α/β DVD-Ig molecules. Antibodies 18F4.2C8 and 1B12.4H4 (see, Example 1.1.D) were used to construct hIL-1α/β DVD3a-Ig, hIL-1α/β DVD4a-Ig, hIL-1α/β DVD3b-Ig, and hIL-1α/β DVD4b-Ig, hIL-1α/βDVD3a-Ig and hIL-1α/βDVD4a-Ig were in a-b-C orientation, with a short and long linker, respectively. hIL-1α/βDVD3b-Ig and hIL-1α/βDVD4b-Ig were in b-a-C orientation, with a short and long linker, respectively. Antibodies 6H3.1A4 and 6B12.4F6 were used to construct hIL-1α/βDVD5a-Ig, hIL-1α/βDVD6a-Ig, hIL-1α/β DVD5b-Ig, and hIL-1α/β DVD6b-Ig, hIL-1α/β DVD5a-Ig and hIL-1α/βDVD6a-Ig were in a-b-C orientation, with a short and long linker, respectively. hIL-1α/β DVD5b-Ig and hIL-1α/βDVD6b-Ig were in b-a-C orientation, with a short and long linker, respectively. The molecular cloning of these additional hIL-1α/β DVD-Ig binding proteins were performed using the procedure previously described for hIL-1α/β DVD1-Ig (see, Example 1.3), using overlapping PCR procedures. The amino acid sequences of these additional hIL-1α/β DVD-Ig binding proteins are disclosed in Table 15.

TABLE 15

Amino Acid Sequence of Heavy Chain and Light Chain of Six DVD-Ig Proteins Capable of Binding IL-1α and IL-1β

| Protein Protein region | Sequence Identifier | Sequence 12345678901234567890 |
|---|---|---|
| DVD-Ig HEAVY VARIABLE hIL-1α/β DVD3a-Ig | SEQ ID NO: 127 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS<u>AS TKGP</u>QVHLKESGPGLVAPSQ SLSITCTVSGFSLTDYGVSW IRQPPGKGLEWLGLIWGGGD TYYNSPLKSRLSIRKDNSKS QVFLKMNSLQTDDTAVYYCA KQRTLWGYDLYGMDYWGQGT SVTVSS |
| 18F4.2C8 VH | SEQ ID NO: 91 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| LINKER | SEQ ID NO: 79 | ASTKGP |
| 1B12.4H4 VH | SEQ ID NO: 97 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD-Ig LIGHT VARIABLE HIL-1α/β DVD3a-Ig | SEQ ID NO: 128 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIK<u>RTVAAP</u>ETTVTQS PASLSMAIGEKVTIRCITST DIDVDMNWYQQKPGEPPKLL ISQGNTLRPGVPSRFSSSGS GTDFVFIIENMLSEDVADYY CLQSDNLPLTFGAGTKLELK RR |
| 18F4.2C8 VL | SEQ ID NO: 92 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| LINKER | SEQ ID NO: 71 | TVAAP |
| 1B12.4H4 VL | SEQ ID NO: 98 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD3b-Ig | SEQ ID NO: 129 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS<u>ASTKGP</u>EVQLQQSGAELV KPGASVKLSCTASGLNIKDT YMHWLKQRPEQGLEWIGRID PANGNAKYDPRFLGKATITA DTSSNTAYLQLSSLTSEDTA VYYCARGDGNFHFDYWGQGT TLTVSS |
| 1B12.4H4 VH | SEQ ID NO: 97 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| LINKER | SEQ ID NO: 79 | ASTKGP |
| 18F4.2C8 VH | SEQ ID NO: 91 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD-Ig LIGHT VARIABLE HIL-1α/β DVD3b-Ig | SEQ ID NO: 130 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELK<u>RTVAAP</u>DIVMTQS QRFMSTSVGDRVSVTCKASQ NVGTNIAWYQQKPGQSPRAL IYSASYRYSGVPDRFTGSGS |

TABLE 15-continued

Amino Acid Sequence of Heavy Chain and Light Chain of Six DVD-Ig Proteins Capable of Binding IL-1α and IL-1β

| Protein Protein region | Sequence Identifier | Sequence 12345678901234567890 |
|---|---|---|
| | | GTDFTLTISNVQSVDLAEYF CQQYTRYPLTFGGGTKLEIK R |
| 1B12.4H4 VL | SEQ ID NO: 98 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| LINKER | SEQ ID NO: 71 | TVAAP |
| 18F4.2C8 VL | SEQ ID NO: 92 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD4a-Ig | SEQ ID NO: 131 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS<u>AS TKGPSVFPLAP</u>QVHLKESGP GLVAPSQSLSITCTVSGFSL TDYGVSWIRQPPGKGLEWLG LIWGGGDTYYNSPLKSRLSI RKDNSKSQVFLKMNSLQTDD TAVYYCAKQRTLWGYDLYGM DYWGQGTSVTSS |
| 18F4.2C8 VH | SEQ ID NO: 91 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| LINKER | SEQ ID NO: 80 | <u>ASTKGPSVFPLAP</u> |
| 1B12.4H4 VH | SEQ ID NO: 97 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV |
| | | LDSDGSFFLYSKLTVDKSRW QQGNVFSCSVMHEALHNHYT QKSLSLSPGK |
| DVD-Ig LIGHT VARIABLE HIL-1α/β DVD4a-Ig | SEQ ID NO: 132 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR<u>TVAAPSVFIFPPP</u> ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| 18F4.2C8 VL | SEQ ID NO: 92 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| LINKER | SEQ ID NO: 72 | <u>TVAAPSVFIFPPP</u> |
| 1B12.4H4 VL | SEQ ID NO: 98 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD4b-Ig | SEQ ID NO: 133 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS<u>ASTKGPSVFPLAP</u>EVQLQ QSGAELVKPGASVKLSCTAS GLNIKDTYMHWLKQRPEQGL EWIGRIDPANGNAKYDPRFL GKATITADTSSNTAYLQLSS LTSEDTAVYYCARGDGNFHF DYWGQGTTLTVSS |
| 1B12.4H4 VH | SEQ ID NO: 97 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| LINKER | SEQ ID NO: 80 | <u>ASTKGPSVFPLAP</u> |
| 18F4.2C8 VH | SEQ ID NO: 91 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |

TABLE 15-continued

Amino Acid Sequence of Heavy Chain and Light Chain of Six DVD-Ig Proteins Capable of Binding IL-1α and IL-1β

| Protein Protein region | Sequence Identifier | Sequence 12345678901234567890 |
|---|---|---|
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD Ig LIGHT VARIABLE HIL-1α/β DVD4b-Ig | SEQ ID NO: 134 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR<u>TVAAPSVFIFPP</u> DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| 1B12.4H4 VL | SEQ ID NO: 98 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| LINKER | SEQ ID NO: 72 | <u>TVAAPSVFIFPP</u> |
| 18F4.2C8 VL | SEQ ID NO: 92 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD5a-Ig | SEQ ID NO: 135 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS<u>ASTKGP</u> EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| 6H3.1A4.3E11 VH | SEQ ID NO: 93 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| LINKER | SEQ ID NO: 79 | ASTKGP |
| 6B12.4F6 VH | SEQ ID NO: 99 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD-Ig LIGHT VARIABLE HIL-1α/β DVD5a-Ig | SEQ ID NO: 136 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR<u>TVAAPQIVLTQSP AIMSASPGEKVTITCSASSS VSYMHWFQQKPGASPKLWIY STSNLASGVPARFSGSGSGT SYSLTVSRMEAEDAATYYCQ QRSTYPYTFGGGTKLEIKR |
| 6H3.1A4.3E11 VL | SEQ ID NO: 94 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| LINKER | SEQ ID NO: 71 | <u>TVAAP</u> |
| 6B12.4F6 VL | SEQ ID NO: 100 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD5b-Ig | SEQ ID NO: 137 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS<u>AS TKGPQVQLQQPGAELVRPGA |

TABLE 15-continued

Amino Acid Sequence of Heavy Chain and Light Chain of Six DVD-Ig Proteins Capable of Binding IL-1α and IL-1β

| Protein Protein region | Sequence Identifier | Sequence 12345678901234567890 |
|---|---|---|
| | | SVKLSCKASGYTFTTYWMNW VKQRPEQGLEWIGRIDPYDS ETLYSQKFKDTAILTVDKSS STAYMQLSSLTSEDSAVYYC ARYGFDYWGQGTTLTVSS |
| 6B12.4F6 VH | SEQ ID NO: 99 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| LINKER | SEQ ID NO: 79 | ASTKGP |
| 6H3.1A4.3E11 VH | SEQ ID NO: 93 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKEVEP KSCDKTHTCPPCPAPELLGG PSVFLFPPEPEDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD Ig LIGHT VARIABLE HIL-1α/β DVD5b-Ig | SEQ ID NO: 138 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKRTVAAPQIVLTQSP ALMSASPGEKVTMTCSASSS VNYMYWYQQKPRSSPKPWIY LTSNLASGVPARFSGSGSGT SYSLTISSMEAEDAATYYCQ QWNSNPYTFGGGTKLEMKR |
| 6B12.4F6 VL | SEQ ID NO: 100 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| LINKER | SEQ ID NO: 71 | TVAAP |
| 6H3.1A4.3E11 VL | SEQ ID NO: 94 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD-Ig HEAVY VARIABLE hIL-1α/β DVD6a-Ig | SEQ ID NO: 139 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSSASTKGP SVFPLAPEVQLQQSGPELVK TGTSVKISCKASGYSFTGYY MHWVRQSHGKSLEWIGYISC YNGFTSYNPKFKGKATFTVD TSSSTAYIQFSRLTSEDSAV YYCARSDYYGTNDYWGQGTT LTVSS |
| 6H3.1A4.3E11 VH | SEQ ID NO: 93 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| LINKER | SEQ ID NO: 80 | ASTKGPSVFPLAP |
| 6B12.4F6 VH | SEQ ID NO: 99 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD-Ig LIGHT VARIABLE HIL-1α/β DVD 6a-Ig | SEQ ID NO: 140 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKRTVAAPSVFIFPPQ IVLTQSPAIMSASPGEKVTI TCSASSSVSYMHWFQQKPGA SPKLWIYSTSNLASGVPARF SGSGSGTSYSLTVSRMEAED AATYYCQQRSTYPYTFGGGT KLEIKRR |
| 6H3.1A4.3E11 VL | SEQ ID NO: 94 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |

TABLE 15-continued

Amino Acid Sequence of Heavy Chain and Light Chain of Six DVD-Ig Proteins Capable of Binding IL-1α and IL-1β

| Protein Protein region | Sequence Identifier | Sequence 12345678901234567890 |
|---|---|---|
| LINKER | SEQ ID NO: 72 | TVAAPSVFIFPP |
| 6B12.4F6 VL | SEQ ID NO: 100 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| CL | SEQ ID NO: 124 | RTVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGEC |
| DVD-Ig HEAVY VARIABLE hIL-1α/β DVD6b-Ig | SEQ ID NO: 141 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSSAS TKGPSVFPLAPQVQLQQPGA ELVRPGASVKLSCKASGYTF TTYWMNWVKQRPEQGLEWIG RIDPYDSETLYSQKFKDTAI LTVDKSSTAYMQLSSLTSE DSAVYYCARYGFDYWGQGTT LTVSS |
| 6B12.4F6 VH | SEQ ID NO: 99 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| LINKER | SEQ ID NO: 80 | ASTKGPSVFPLAP |
| 6H3.1A4.3E11 VH | SEQ ID NO: 93 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| CH | SEQ ID NO: 122 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD-Ig LIGHT VARIABLE HIL-1α/β DVD6b-Ig | SEQ ID NO: 142 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKRTVAAPSVFIFPPQ IVLTQSPALMSASPGEKVTM TCSASSSVNYMYWYQQKPRS SPKPWIYLTSNLASGVPARF SGSGSGTSYSLTISSMEAED AATYYCQQWNSNPYTFGGGT KLEMKRR |
| 6B12.4F6 VL | SEQ ID NO: 100 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| LINKER | SEQ ID NO: 72 | TVAAPSVFIFPP |
| 6H3.1A4.3E11 VL | SEQ ID NO: 94 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| CL | SEQ ID NO: 124 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

Characteristics of the new DVD-Ig constructs are summarized in Table 16. Affinity (Kd) and biological activity (IC50) were determined by Biacore and MRC-5 bioassay, respectively. SDS-PAGE analysis of all new DVD-Ig proteins showed normal migration patterns in both reduced and non-reduced conditions, similar to a regular antibody and DVD1/2-Ig.

TABLE 16

Characterization of New DVD-Ig Molecules Derived from New mAb Pairs

| mAb | Specif. | $K_d$ (M) | $IC_{50}$ (M) | DVD | Orient. | Linker | Affinity ($K_d$) M IL-1α | IL-1β | Potency ($IC_{50}$) M IL-1α | IL-1β |
|---|---|---|---|---|---|---|---|---|---|---|
| 18F4.2C8 | rhIL-1α | $5.95 \times 10^{-10}$ | $3.30 \times 10^{-10}$ | DVD3a | a-b-C | short | $8.37 \times 10^{-10}$ | $6.37 \times 10^{-8}$ | $7.50 \times 10^{-10}$ | NA |
| 1B12.4H4 | rhIL-1β | $2.61 \times 10^{-10}$ | $6.00 \times 10^{-10}$ | DVD4a | a-b-C | long | $7.01 \times 10^{-10}$ | $9.30 \times 10^{-10}$ | $3.50 \times 10^{-10}$ | $1.00 \times 10^{-8}$ |
| | | | | DVD3b | b-a-C | short | $1.24 \times 10^{-9}$ | $1.90 \times 10^{-10}$ | $7.00 \times 10^{-10}$ | $4.00 \times 10^{-10}$ |
| | | | | DVD4b | b-a-C | long | $5.60 \times 10^{-10}$ | $1.28 \times 10^{-10}$ | $3.50 \times 10^{-10}$ | $5.00 \times 10^{-10}$ |
| 6H3.1A4 | rhIL-1α | $3.54 \times 10^{-10}$ | $2.40 \times 10^{-10}$ | DVD5a | a-b-C | short | $5.08 \times 10^{-10}$ | $1.25 \times 10^{-8}$ | $2.60 \times 10^{-9}$ | $1.90 \times 10^{-8}$ |

TABLE 16-continued

Characterization of New DVD-Ig Molecules Derived from New mAb Pairs

| mAb | Specif. | $K_d$ (M) | $IC_{50}$ (M) | DVD | Orient. | Linker | Affinity ($K_d$) M | | Potency ($IC_{50}$) M | |
|---|---|---|---|---|---|---|---|---|---|---|
| | | | | | | | IL-1α | IL-1β | IL-1α | IL-1β |
| 6B12.4F6 | rhIL-1β | $5.54 \times 10^{-10}$ | $4.00 \times 10^{-10}$ | DVD6a | a-b-C | long | $1.06 \times 10^{-9}$ | $2.09 \times 10^{-9}$ | $2.30 \times 10^{-9}$ | $7.00 \times 10^{-8}$ |
| | | | | DVD5b | b-a-C | short | $1.32 \times 10^{-8}$ | $6.71 \times 10^{-10}$ | $3.30 \times 10^{-9}$ | $2.50 \times 10^{-10}$ |
| | | | | DVD6b | b-a-C | long | $8.20 \times 10^{-10}$ | $6.97 \times 10^{-10}$ | $1.00 \times 10^{-9}$ | $7.50 \times 10^{-10}$ | mAb = monoclonal antibody;
NA = no neutralization activity detected.

The functional characterization of the new DVD-Ig molecules revealed that with either orientation, DVD-Ig molecules with the long linker performed better than the ones with the short linker in terms of binding and neutralizing of both antigens. With respect to DVD-Ig molecules with the long linkers, those with the b-a-C orientation showed good binding to and neutralization of both antigens, while the DVD-Ig molecules with an a-b-C orientation showed good binding to and neutralization of IL-1α and reduced binding to and neutralization of IL-1β (e.g., DVD4b vs. DVD4a). The DVD-Ig molecule, DVD4b, bound and neutralized both IL-1α and IL-1β with sub-nM and fully retained the binding and neutralizing characteristics of the parent mAbs.

Example 3

Generation of mIL-1α/β DVD-Ig Molecules

To study key issues concerning pharmacokinetics, in vivo efficacy, tissue penetration, and immunogenicity of DVD-Ig molecules, mouse-anti-mouse IL-1α/β DVD-Ig molecules were constructed as described below.

Example 3.1

Construction of mIL-1α/β DVD-Ig Molecules

Mouse anti-mouse IL-1α/β DVD-Ig molecules were constructed using two mouse anti-mouse IL-1α/β monoclonal antibodies (9H10 and 10G11) generated from IL-1αβ double KO mice. Mouse anti-mouse IL-1α, and mouse anti-mouse IL-1β, monoclonal antibodies (mAbs) were generated by immunizing IL-1α/β double KO mice with mouse IL-1α, or mouse IL-1β, respectively. One mouse anti-mouse IL-1α (Clone 9H10) and one mouse anti-mouse IL-1β mAb (clone 10G11), were selected and used to generate mIL-1α/β DVD-Ig molecules. Various linker sizes and different domain orientations were tested. The final functional mIL-1α/β DVD-Ig molecule was constructed in an orientation of V(anti-mIL-1β)-linker-V(anti-mIL-1α)-murine constant region (Cγ2a and Cκ). The cloning, expression, and purification procedures were similar to that of the hIL-1α/β DVD-Ig binding protein. The cloning of mIL-1α/β DVD-Ig binding protein was carried out using similar overlapping PCR and homologous recombination as described for hIL-1α/β DVD3-Ig. The sequences of mIL-1α/β DVD-Ig binding proteins are shown below in Table 17.

TABLE 17

Amino Acid Sequence of mIL-1α/β DVD-Ig Binding Protein

| Protein region | Sequence Identifier | Sequence 12345678901234567890 |
|---|---|---|
| mIL-1α/β DVD-Ig HEAVY VARIABLE | SEQ ID NO: 143 | EVQLQQSGPELVKPGTSVKM SCKTSGYTFTSYVMHWVKQK PGQGLEWIGYIIPYNDNTKY NEKFKGKATLTSDKSSSTAY MELSSLTSEDSAVYYCARRN EYYGSSFFDYWGQGTTLTVS SAKTTAPSVYPLAPQVILKE SGPGILQPSQTLSLTCSFSG FSLSTYGTAVNWIRQPSGKG LEWLAQIGSDDRKLYNPFLK SRITLSEDTSNSQVFLKITS VDTEDSATYYCANGVMEYWG LGTSVTVSS |
| 10G11 VH | SEQ ID NO: 144 | EVQLQQSGPELVKPGTSVKM SCKTSGYTFTSYVMHWVKQK PGQGLEWIGYIIPYNDNTKY NEKFKGKATLTSDKSSSTAY MELSSLTSEDSAVYYCARRN EYYGSSFFDYWGQGTTLTVS S |
| LINKER | SEQ ID NO: 78 | AKTTAPSVYPLAP |
| 9H10 VH | SEQ ID NO: 145 | QVILKESGPGILQPSQTLSL TCSFSGFSLSTYGTAVNWIR QPSGKGLEWLAQIGSDDRKL YNPFLKSRITLSEDTSNSQV FLKITSVDTEDSATYYCANG VMEYWGLGTSVTVSS |
| CH | SEQ ID NO: 146 | AKTTAPSVYPLAPVCGDTTG SSVTLGCLVKGYFPEPVTLT WNSGSLSSGVHTFPAVLQSD LYTLSSSVTVTSSTWPSQSI TCNVAHPASSTKVDKKIEPR GPTIKPCPPCKCPAPNLLGG PSVFIFPPKIKDVLMISLSP IVTCVVVDVSEDDPDVQISW FVNNVEVHTAQTQTHREDYN STLRVVSALPIQHQDWMSGK EFKCKVNNKDLPAPIERTIS KPKGSVRAPQVYVLPPPEEE MTKKQVTLTCMVTDFMPEDI YVEWTNNGKTELNYKNTEPV LDSDGSYFMYSKLRVEKKNW VERNSYSCSVVHEGLHNHHT TKSFSRTPGK |
| mIL-1α/β DVD-Ig LIGHT VARIABLE | SEQ ID NO: 147 | DIQMTQSPASLSASVGETVT ITCRGSGILHNYLVWYQQKQ GKSPQLLVYSAKILADGVPS RFSGSGSGTQYSLKINSLQP EDFGSYYCQHFWSTPFTFGS GTKLEIKRADAAPTVSIFPP |

TABLE 17-continued

Amino Acid Sequence of mIL-1α/β DVD-Ig Binding Protein

| Protein region | Protein Sequence Identifier | Sequence 12345678901234567890 |
|---|---|---|
| | | SIVMTQTPKFLLVSAGDRVT<br>ITCKASQSVNHDVAWYQQMP<br>GQSPKLLIYFASNRYTGVPD<br>RFTGSGYGTDFTFTISTVQA<br>EDLAVYFCQQDYSSPYTFGG<br>GTKLEIKR |
| 10G11 VL | SEQ ID NO: 148 | DIQMTQSPASLSASVGETVT<br>ITCRGSGILHNYLVWYQQKQ<br>GKSPQLLVYSAKILADGVPS<br>RFSGSGSGTQYSLKINSLQP<br>EDFGSYYCQHFWSTPFTFGS<br>GTKLEIKR |
| LINKER | SEQ ID NO: 70 | ADAAPTVSIFPP |
| 9H10 VL | SEQ ID NO: 149 | SIVMTQTPKFLLVSAGDRVT<br>ITCKASQSVNHDVAWYQQMP<br>GQSPKLLIYFASNRYTGVPD<br>RFTGSGYGTDFTFTISTVQA<br>EDLAVYFCQQDYSSPYTFGG<br>GTKLEIKR |
| CL | SEQ ID NO: 150 | ADAAPTVSIFPPSSEQLTSG<br>GASVVCFLNNFYPKDINVKW<br>KIDGSERQNGVLNSWTDQDS<br>KDSTYSMSSTLTLTKDEYER<br>HNSYTCEATHKTSTSPIVKS<br>FNRNEC |

Murine mIL-1α/β DVD-Ig binding proteins retained affinity/in vitro potency against both murine IL-1α (mIL-1α) and murine IL-1β (mIL-1β). Table 18 shows the characterization of mAbs 9H10 (anti-mIL-1α), 10G11 (anti-mIL-1β), and mIL-1α/β DVD-Ig binding proteins.

TABLE 18

Characterization of mDVD4-Ig

| | Antigen | $K_D$ (M) | $IC_{50}$ (M) |
|---|---|---|---|
| 9H10 | mIL-1α | $1.73 \times 10^{-10}$ | $2.00 \times 10^{-10}$ |
| 10G11 | mIL-1β | $2.30 \times 10^{-10}$ | $3.70 \times 10^{-10}$ |
| mIL-1α/βDVD-Ig | mIL-1α | $7.66 \times 10^{-10}$ | $2.00 \times 10^{-9}$ |
| | mIL-1β | $6.94 \times 10^{-10}$ | $8.00 \times 10^{-10}$ |

Example 3.2

In Vivo Activity of mIL-1α/βDVD-Ig Binding Proteins in Rheumatoid Arthritis Model The therapeutic effects of anti-IL-1α, anti-IL-1β, combined anti-IL-1α/anti-IL-1β, and murine IL-1α/β DVD4-Ig, were evaluated in a collagen-induced arthritis mouse model well known in the art. Briefly, male DBA-1 mice were immunized with bovine type II collagen in CFA at the base of the tail. The mice were boosted with Zymosan intraperitoneally (i.p) at day 21. After disease onset at day 24-27, mice were selected and divided into separate groups of 10 mice each. The mean arthritis score of the control group, and anti-cytokine groups was comparable at the start of treatment. To neutralize IL-1, mice were injected every other day with 1-3 mg/kg of anti-IL-1α mAb, anti-IL-1βmAb, combination of anti-IL-1α and anti-IL-1β mAbs, or murine IL-1α/β DVD4-Ig intraperitoneally. Mice were carefully examined three times a week for the visual appearance of arthritis in peripheral joints, and scores for disease activity determined.

Blockade of IL-1 in the therapeutic mode effectively reduced the severity of arthritis, with anti-IL-1β showing greater efficacy (24% reduction in mean arthritis score compared to control group) than anti-IL-1α (10% reduction). An additive effect was observed between anti-IL-1α and anti-IL-1β, with a 40% reduction in mean arthritis score in mice treated with both anti-IL-1α and anti-IL-1β mAbs. Surprisingly, at the same dose level, the treatment of mDVD-Ig binding protein exhibited 47% reduction in mean arthritis score, demonstrating the in vivo therapeutic efficacy of mDVD-Ig binding protein. Similar efficacy was also observed in the measurements of joint swelling in this animal model.

Example 3.3

In Vivo Activity of a Murine IL-1α/β DVD-Ig Binding Protein in Osteoarthritis Models The above study showed that the blockade of both IL-1α and IL-1β with a combination of anti-mouse IL-1α and IL-1β antibodies as well as a murine anti-mouse IL-1α/β DVD-Ig binding proteins was significantly more efficacious than either single antibody alone in the mouse collagen-induced arthritis (CIA) model for rheumatoid arthritis (see, also, Wu et al., Nature Biotech., 25(11): 12901297 (2007)). The efficacy of anti-IL-1 therapy in osteoarthritis (OA) was studied two animal models of OA, i.e., the joint instability model ("JIM") and the destabilization of medial meniscus ("DMM") in mice.

Example 3.3.1

In Vivo Activity of Mouse Anti-Murine IL-1α and Anti-Murine IL-1β Monoclonal Antibodies in Joint Instability Model (JIM) of Osteoarthritis in Mice Example 3.3.1.A Study Design The design of study of the in vivo activity of a mIL-1α/β DVD-Ig molecule in the joint instability model (JIM) of osteoarthritis in mice is shown in Table 19. All groups contained 25 mice (n=25), weighing approximately 30 grams (BW=30 g). The study was terminated after 21 days. Two and a half month old, male Swiss Webster mice (25/group/time point), housed 5/cage, were anesthetized with isoflurane anesthesia. Anterior cruciate ligament (ACL) trauma was administered on the right and left knees on day 0 in an attempt to induce OA lesions. Intraperitoneal (ip) treatments with IL-1 inhibitory antibodies IL-1α (9H10) and IL-1β (10G11), alone and in combination, were initiated the day of ACL trauma and continued every 4th day (q4d) for 20 days. The vehicle for the non-treatment control was PBS. Right and left knees were harvested on day 21, and histopathologic alterations were scored and characterized. Data were analyzed using only joints that had proliferative responses indicative of successful instability induction. The proliferative response/instability was scored 0-3, and only unstable joints (scores of 1, 2, or 3) were used in the final analysis. Medial and lateral femoral and tibial cartilage degeneration was scored for severity of cartilage degeneration on a scale 0-5. Four days after the last antibody dose, blood was drawn from all animals from each group for serum harvest. Body weights were recorded weekly. On the final day, animals (10 animals in Groups 1, 2, 3, 4) were dosed with Zymosan A and blood drawn 4 hours later (at termination) for serum analysis of IL-6 (IL-1/TNF dependent). Animals were killed on day 21 and right and left knee joints collected into formalin.

TABLE 19

Design of Study in Joint Instability Animal Model for Osteoarthritis

| Treatment Group | Compound | Route | Dosing Regimen |
|---|---|---|---|
| Group 1 | Vehicle 1 (PBS) | ip | Q4D (2 times per week) |
| Group 2 | anti-IL-1α (9H10) | ip | Q4D (2 times per week) |
| Group 3 | anti-IL-1β (10G11) | ip | Q4D (2 times per week) |
| Group 4 | anti-IL-1α (9H10) and anti-IL-1β (10G11) | ip | Q4D (2 times per week) |

Example 3.3.1.B

Tissue Preparation and Analysis

Tissue Preparation:

Following 2-3 days in a decalcifying fixative (Surgipath Decalifier, Surgipath Medical Ind., Inc., Richmond Va.), both knee joints were trimmed of extraneous tissue, embedded in the frontal plane and sectioned. One section was taken from each animal (2 joints/block) at the approximate mid point of the frontal plane. All sections were 8 μm and were stained with Toluidine blue. Slides were examined by a board-certified veterinary pathologist blinded to study group designation, and were scored according to the method below. Statistical analysis was performed using Microsoft Excel, and included a 2-tailed t-test comparing all treatment groups to the control group using a confidence level of 95%.

Histopathologic Scoring of Joints:

Medial and lateral femoral and tibial cartilage degeneration were scored for severity of cartilage degeneration using the following system: Depth/extent of chondrocyte and proteoglycan loss with fibrillation:

1=superficial damage, tangential layer of collagen absent over 50% or greater of the zone surface or up to 10% loss of proteoglycan and/or chondrocytes in focal or diffuse distribution in zone 2=matrix loss extends into upper ¼ of 50% or greater area of the zone or up to 25% loss of proteoglycan and/or chondrocytes in focal or diffuse distribution in zone 3=matrix loss extends through ½ of cartilage thickness over 50% or greater of the zone or up to 50% loss of proteoglycan and/or chondrocytes in focal or diffuse distribution in zone 4=matrix loss extends through ¾ of cartilage thickness over 50% or greater of the zone or up to 75% loss of proteoglycan and/or chondrocytes in focal or diffuse distribution in zone 5=matrix loss extends through entire cartilage thickness over 50% or greater of the zone or up to 100% loss of proteoglycan and/or chondrocytes in focal or diffuse distribution in zone Scores were assigned with attention to zonal (inside, middle and outside) distribution of lesions, and the scores (0-5) for each third were summed for each area of the joint and then for the whole joint.

Osteophytes (largest on tibial or femoral surface under evaluation) were measured using digital software (NIS-Elements version 3.0).

Osteophyte Evaluation=1, 2, or 3 for small, medium or large depending on size

Small osteophytes=1 (up to 150 μm)
Medium osteophytes=2 (151-300 μm)
Large osteophytes=3 (>301 μm)

Synovial reaction was described and characterized with respect to inflammation type and degree if present was not included in the score.

The mean±SE for each of the various parameters for each animal was determined and summed to arrive at a total joint score.

Joints with histologic evidence of instability induction were identified by the presence of proliferative changes in the medial synovium and collateral ligaments. In addition, an instability score was recorded for each joint according to the following criteria.

0=No instability
1=Mild instability (minimal to mild proliferative changes in ligaments and marginal zones)
2=Moderate instability (moderate proliferative changes in ligaments and marginal zones)
3=Severe instability (severe proliferative changes in ligaments and marginal zones)

Figure 2:
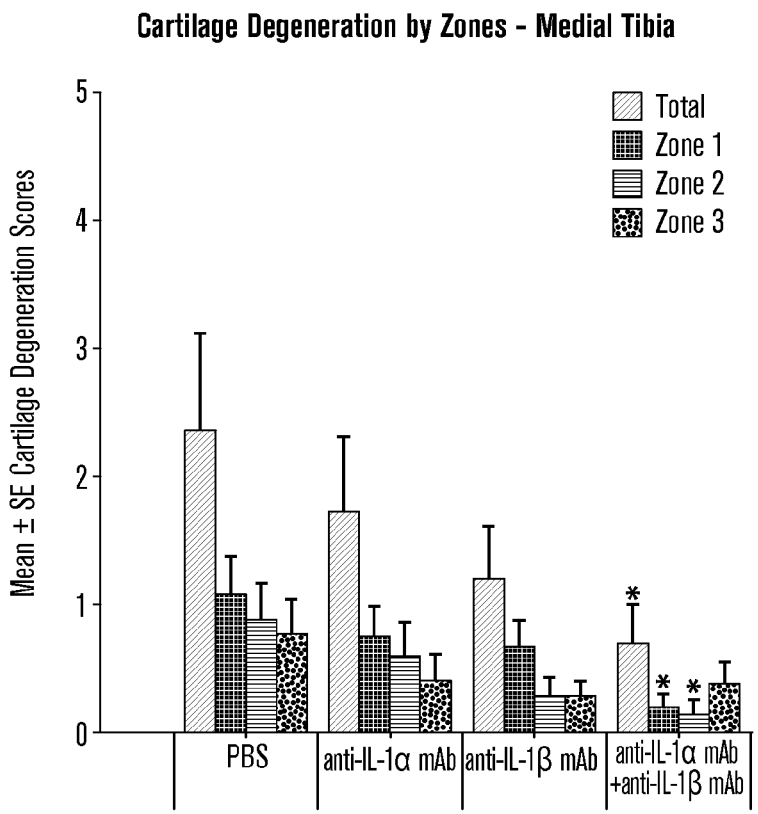
FIG. 2 shows bar graphs of histology scoring of articular cartilage of mice in a joint instability model (JIM) of osteoarthritis. Each set of bar graphs provides scoring for articular cartilage in knees of mice in four treatment groups: treatment with phosphate buffered saline (PBS) vehicle only ("PBS"), treatment with an anti-IL-1α monoclonal antibody ("anti-IL-1α mAb"), treatment with an anti-IL-1β monoclonal antibody ("anti-IL-1β mAb"), and treatment with a combination of anti-IL-1α and anti-IL-1β monoclonal antibodies ("anti-IL-1α mAb+anti-IL-1β mAb"). Individual bar graphs within each set show a total histology score and scores for three separate zones, wherein each zone is one-third of the area of the medial tibia cartilage (zone 1: inside zone, zone 2: middle zone, and zone 3: outside zone). From left to right: bar graph of total score for medial tibia zones 1, 2, and 3; bar graph of score for medial tibia zone 1; bar graph of score for medial tibia zone 2; and bar graph of score for medial tibia zone 3. See Example 3.3.1.

Results:

Only unstable joints with scores of 1, 2, or 3 (or 2, 3) were used in the final data analysis. Data were ultimately analyzed on a total affected joint basis rather than affected animal basis. The results of this study indicated that joints of animals treated with either anti-IL-1α or IL-1β monoclonal antibodies exhibited cartilage degeneration similar to that seen in vehicle-treated control joints. However, a combination therapy with both a mouse anti-mouse IL-1α mAb (9H10) and a mouse anti-mouse IL-1β mAb (10G11) significantly decreased medial tibial cartilage degeneration scores. FIG. 2 shows bar graphs of cartilage degeneration scores in the joints of the animals in the various treatment groups.

Example 3.3.2

In Vivo Activity of mIL-1α/β DVD-Ig Binding Protein in Joint Instability Model (JIM) of Osteoarthritis in Mice The joint instability model for osteoarthritis as described above in Example 3.3.1, was also used to compare the efficacy of anti-IL-1 therapy as provided by a combination of a mouse anti-mIL-1α monoclonal antibody (9H10) and a mouse anti-mIL-1β monoclonal antibody (10G11) with that provided by a mIL-1α/β DVD-Ig binding protein generated from the two monoclonal antibodies.

Example 3.3.2.A

Study Design

The design of this study was similar to that described above in Example 3.3.1. Two and a half month old, male Swiss Webster mice (25/group/time point), housed 5/cage, were anesthetized with isoflurane anesthesia and the right and left knee area clipped and prepared for intra-articular trauma to the cruciate ligaments on day 0. Dosing (initiated on day 0, ip) was carried out once every 4 days (Q4D) with animals terminated on day 21 (for Group 2). Dosing (initiated on day 0, ip) was carried out three times weekly with animals terminated on day 21 (for Groups 1, 3 and 4). Four days after the last antibody dose, all animals from each group had blood drawn for serum harvest. Body weights were recorded weekly. On the final day, animals (10 animals in Groups 1, 2, 3, 4) were dosed with Zymosan A and blood drawn 4 hours later (at termination) for serum analysis of IL-6 (IL-1/TNF dependent). Animals were euthanized on day 21 and right and left knee joints collected into formalin. See the study design table below.

TABLE 20

Design of Study of Joint Instability Animal Model for Osteoarthritis

| Treatment Group | Compound | Route | Dosing Regimen | Dose Level (mg/kg) |
|---|---|---|---|---|
| Group 1 | Vehicle 1 (PBS) | ip | 3 times per week | 6.7 ml/kg |
| Group 2 | anti-IL-1α (9H10) and anti-IL-1β (10G11) | ip | Q4D (3 times per week) | anti-IL-1α at 6 mg/kg (180 μg/mouse) and anti-IL-1β at 6 mg/kg (180 μg/mouse) |
| Group 3 | mIL-1α/β DVD-Ig | ip | 3 times per week | 12 mg/kg (500 μg/mouse) |
| Group 4 | mIL-1α/β DVD-Ig | ip | 3 times per week | 6 mg/kg (250 μg/mouse) |

Example 3.3.2.B

Tissue Preparation and Analysis

Figure 3:
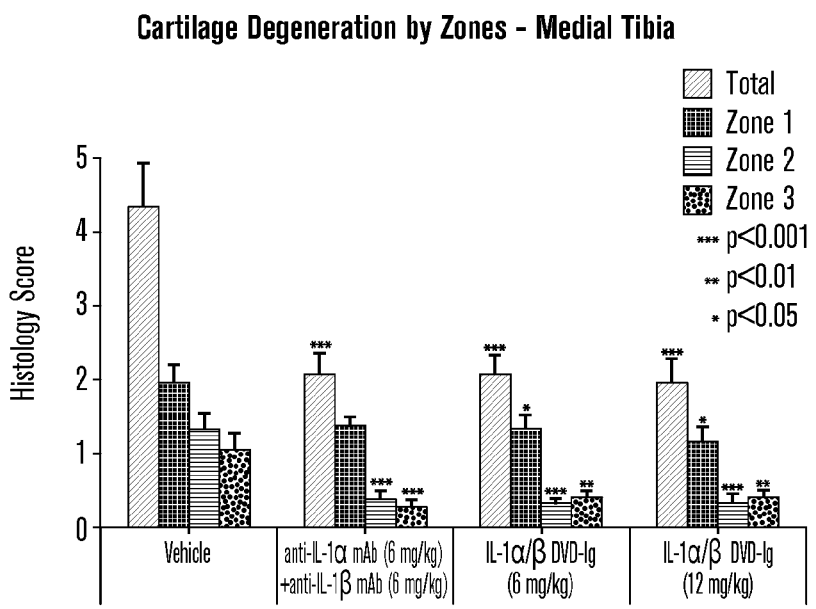
FIG. 3 shows bar graphs of histology scoring of articular cartilage of mice in a joint instability model (JIM) of osteoarthritis. Each set of bar graphs provides scoring for articular cartilage in knees of mice in four treatment groups: treatment with PBS vehicle only ("Vehicle"), treatment with a combination of anti-IL-1α monoclonal antibody and anti-IL-1β monoclonal antibody ("anti-IL-1α mAb (6 mg/kg)+anti-IL-1β mAb (6 mg/kg)"), treatment with mIL-1α/β DVD-Ig binding protein at 6 mg/kg ("IL-1α/β DVD-Ig (6 mg/kg)"), and treatment with mIL-1α/β DVD-Ig binding protein at 12 mg/kg ("IL-1α/β DVD-Ig (12 mg/kg)"). Individual bar graphs within each set show a total histology score and scores for three separate zones, wherein each zone is one-third of the area of the medial tibia cartilage (zone 1: inside zone, zone 2: middle zone, and zone 3: outside zone). From left to right: bar graph of total score for medial tibia zones 1, 2, and 3; bar graph of score for medial tibia zone 1; bar graph of score for medial tibia zone 2; and bar graph of score for medial tibia zone 3. See Example 3.3.2.

Tissue preparation and histological scoring of articular cartilage from joints of animals in the various treatments groups were carried out as described above in Example 3.3.1.
Results:
The results indicated that treatment of mice with the mIL-1α/β 10G11-9H10 DVD-Ig binding protein significantly inhibited the progression of osteoarthritis (P<0.05 vs. vehicle) with comparable efficacy to the combination of the parental mAbs 9H10 and 10G11. FIG. 3 shows bar graphs of cartilage degeneration scores in the joints of the animals in the various treatment groups. As shown in FIG. 3, results of treatment with 6 or 12 mg/kg the DVD-Ig binding protein were similar in their efficacy in terms of preventing osteoarthritic lesions. (A treatment using 3 mg/kg DVD-Ig binding protein had not effect on cartilage degeneration and results were similar to vehicle treated joints. See, Example 3.3.3, below.) The results of this study indicated that treatment with a combination of anti-IL-1α and anti-IL-1β monoclonal antibodies or with an IL-1α/β DVD-Ig binding protein had significant beneficial effects on histopathological parameters in the mouse model of osteoarthritis.

Example 3.3.3

Follow Up Study in Joint Instability Model of Osteoarthritis to Compare Treatment with Anti-IL-1β Monoclonal Antibody and Other Binding Proteins A follow up study was performed using the joint instability model of osteoarthritis to more closely determine whether or not there may be any significant effect on medial tibial cartilage degeneration scores in animals treated with an anti-IL-1β monoclonal antibody alone compared to other treatments. The effect of treatment with an anti-IL-1β monoclonal antibody was evaluated in a 21 day study.

Example 3.3.3.A

Study Design

The design of this study was similar to that described above in Example 3.3.1.

TABLE 21

Design Of 21 Day Joint Instability Animal Model For Osteoarthritis

| Treatment Group | Compound | Route | Dosing Regimen | Dose Level (mg/kg) |
|---|---|---|---|---|
| Group 1 | Vehicle 1 (PBS) | ip | Q4D | 6.7 ml/kg |
| Group 2 | anti-IL-1α (9H10) and anti-IL-1β (10G11) | ip | Q4D | anti-IL-1α at 6 mg/kg (180 μg/mouse) and anti-IL-1β at 6 mg/kg (180 μg/mouse) |
| Group 3 | anti-IL-1β (10G11) | ip | Q4D | 12 mg/kg (360 μg/mouse) |
| Group 4 | anti-IL-1β (10G11) | ip | Q4D | 6 mg/kg (180 μg/mouse) |
| Group 5 | anti-IL-1β (10G11) | ip | Q4D | 3 mg/kg (90 μg/mouse) |

Example 3.3.3.B

Tissue Preparation and Analysis

Figure 4:
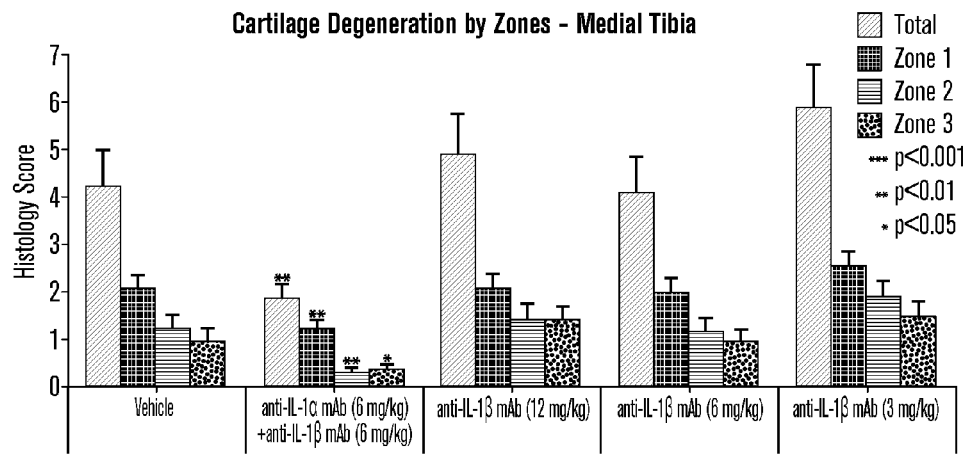
FIG. 4 shows bar graphs of histology scoring of articular cartilage of mice in a joint instability model (JIM) of osteoarthritis. Each set of bar graphs provides scoring for articular cartilage in knees of mice in four treatment groups: treatment with PBS vehicle only ("Vehicle"), treatment with a combination of anti-IL-1α monoclonal antibody (6 mg/kg) and anti-IL-1β monoclonal antibody (6 mg/kg) ("anti-IL-1α mAb (6 mg/kg)+anti-IL-1β mAb (6 mg/kg)"), treatment with an anti-IL-1β monoclonal antibody (12 mg/kg) ("anti-IL-1β mAb (12 mg/kg)"), treatment with an anti-IL-1β monoclonal antibody (6 mg/kg) ("anti-IL-1β mAb (6 mg/kg)"), and treatment with an anti-IL-1β monoclonal antibody (3 mg/kg) ("anti-IL-1β mAb (3 mg/kg)"). Individual bar graphs within each set show a total histology score and scores for three separate zones, wherein each zone is one-third of the area of the medial tibia cartilage (zone 1: inside zone, zone 2: middle zone, and zone 3: outside zone). From left to right: bar graph of total score for medial tibia zones 1, 2, and 3; bar graph of score for medial tibia zone 1; bar graph of score for medial tibia zone 2; and bar graph of score for medial tibia zone 3. See Example 3.3.3.

Tissue preparation and histological scoring of articular cartilage from joints of animals in the various treatments groups were carried out as described above in Example 3.3.1.
Results:
As shown in the FIG. 4, the results confirmed those of previous studies where similar positive treatment effects were noted using a combination of anti-IL-1α and anti-IL-1β monoclonal antibodies and that treatment with an anti-IL-1β monoclonal antibody alone was not effective in preventing cartilage degradation at any dose tested.

Example 3.3.4

Figure 5:
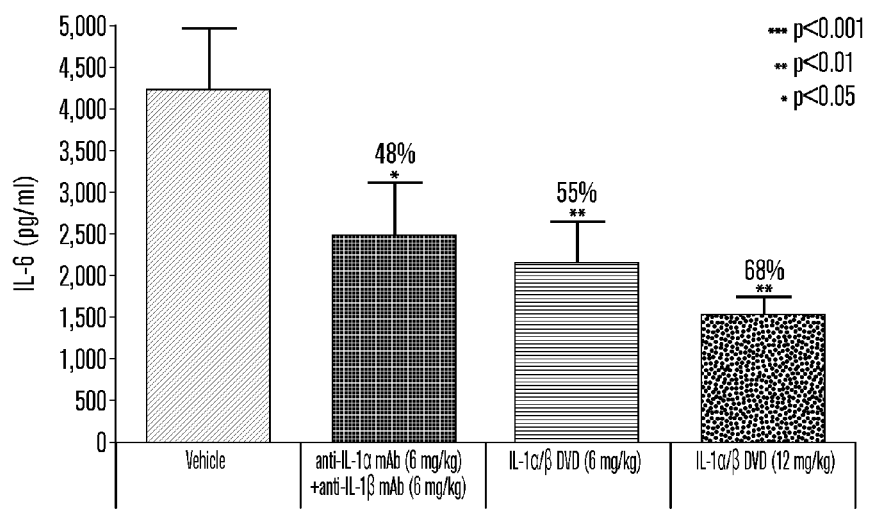
FIG. 5 shows the level of zymosan-induced IL-6 production (pg/ml) in animals in a joint instability model of osteoarthritis when treated with PBS vehicle only ("Vehicle"), with a combination of anti-IL-1α monoclonal antibody (6 mg/kg) and anti-IL-1β monoclonal antibody (6 mg/kg) ("anti-IL-1α mAb (6 mg/kg)+anti-IL-1β mAb (6 mg/kg)"), with mIL-1α/β DVD-Ig binding protein at 6 mg/kg ("IL-1α/β DVD (6 mg/kg)"), and treatment with mIL-1α/β DVD-Ig binding protein at 12 mg/kg ("IL-1α/β DVD (12 mg/kg)"). See Example 3.3.4.

Zymosan-Induced Interleukin-6 (IL-6) Production in a Joint Instability Model Study As a pharmacodynamic readout to determine if anti-IL-1α and anti-IL-1β monoclonal antibodies as well as mIL-1α/β DVD-Ig binding protein were functional and capable of neutralizing IL-1α and IL-1β in vivo, zymosan-induced (IL-1α and IL-1β dependent) production of interleukin 6 (IL-6) was measured in a joint instability model study of OA.
Briefly, on day 21 in the model, zymosan was suspended in PBS vehicle and placed in boiling water for half an hour, then allowed to cool before using. The mice were then injected ip with 50 mg/kg zymosan in suspension (mixed well before injection) in 0.5 ml PBS. The mice were then bled 4 hours after zymosan injection. Serum was collected for IL-6 measurements.
Results:
As shown in FIG. 5, a combination of anti-IL-1α monoclonal antibody (6 mg/kg) and anti-IL-1β monoclonal antibody (6 mg/kg) monoclonal antibodies as well as mIL-1α/β DVD-Ig binding protein (at 6 mg/kg or at 12 mg/kg) significantly neutralized zymosan-induced IL-6 production as compared to vehicle-treated control animals. Accordingly, the antibodies exhibited functional activity in vivo.

Example 3.3.5

Effect of Cytokine Inhibitory Antibody Treatments on Osteoarthritis Induced by Destabilization of Medial Meniscus (DMM) Model in SV129 Mice An alternative animal model was also employed to study the affect of anti-IL-1α and anti-IL-1β activity on slowing progression of cartilage degeneration in osteoarthritis. The mouse destabilization of medial meniscus (DMM) model for osteoarthritis is less invasive and inflammatory than the JIM procedure (see, above) and results in lesions primarily on the central weight-bearing region of the medial tibial plateau and medial femoral condyle. The severity and location of lesions following DMM are more consistent when compared to JIM.

Example 3.3.5.A

Study Design

Male SV129 mice weighing approximately 30 grams, housed 5/cage, were anesthetized on Day 0 with ketamine/xylazine cocktail, administered intraperitoneally (ip), and then the medial collateral ligament was exposed by blunt dissection, and transected to reflect the meniscus toward the femur. The joint space was closed with 8-0 vicryl suture. The skin was closed with wound glue. For sham surgeries, a vertical skin incision was made over the medial aspect of the knee and the joint capsule was opened. The capsule was closed with 8-0 vicryl suture and the skin was closed with wound glue. Groups of animals were then treated with intraperitoneal (ip) injections of antibody or vehicle according to the study design table below. Two sex-matched, age-matched, and strain-matched naïve mice were also included in the study. Animals were euthanized after 8 weeks of treatment, and knee joints were harvested in 10% neutral buffered formalin.

TABLE 22

Design of Study Using Destabilization of Medial Meniscus (DMM) Model of Osteoarthritis

| Treatment Group | Compound | Number of Animals (n) | Dose, Route, and Regimen | Sacrifice Time Point |
|---|---|---|---|---|
| A | sham (none) | 5 | none | 8 weeks |
| B | vehicle (PBS) | 10 | ip, 3x/week | 8 weeks |
| C | anti-IL-1α mAb and anti-IL-1β mAb | 11 | 180 µg/mouse for each antibody, ip, every 4th day | 8 weeks |
| D | mIL-1α/β DVD-Ig | 10 | 250 µg/mouse, ip, 3x/week | 8 weeks |

Example 3.3.5.B

Examination of Tissues

Formalin-fixed samples were decalcified, and specimens were sectioned in the frontal plane into 15 step sections each. Each section was approximately 6 µm thick, and step sections were separated by 70 µm. All slides were stained with toluidine blue (T. Blue). Slides were assessed according to the Chambers method (Chambers et al. (2001) Arthritis Rheum 44:1455-65) for cartilage degeneration (see below) by a board-certified veterinary pathologist. Each of the four cartilage surfaces, the medial femoral condyle (MFC), the medial tibial plateau (MTP), the lateral femoral condyle (LFC), and the lateral tibial plateau (LTP), was scored from 0-6 according to the scale in the table below.

TABLE 23

Chambers Scoring System for Cartilage Degeneration

| Grade | Osteoarthritic Damage |
|---|---|
| 0 | No damage |
| 1 | Roughened articular surface and small fibrillations |
| 2 | Fibrillation down to the layer immediately below the superficial layer (zone 2) and some loss of surface lamina |
| 3 | Loss of surface lamina and fibrillations extending down to the calcified cartilage |
| 4 | Major fibrillations and cartilage erosion down to the subchondral bone |
| 5 | Major fibrillations and erosion of up to 80% of the cartilage |
| 6 | More than 80% loss of cartilage |

Statistical analysis was performed using GraphPad Prism software version 4.03 using Mann-Whitney U test.

Example 3.3.5.C

Results

Figure 6:
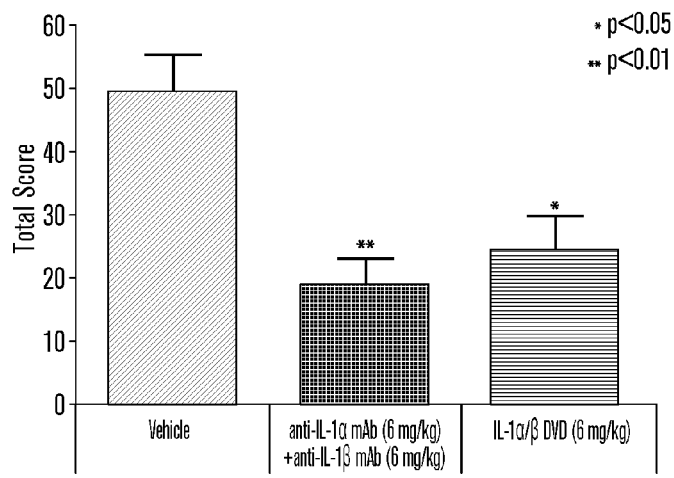
FIG. 6 shows total sum score for cartilage degeneration in animals in a destabilization of medial meniscus (DMM) model of osteoarthritis treated the PBS vehicle ("Vehicle"), with a combination of anti-IL-1α monoclonal antibody (6 mg/kg) and anti-IL-1β monoclonal antibody (6 mg/kg) ("anti-IL-1α mAb (6 mg/kg)+anti-IL-1β mAb (6 mg/kg)"), and with mIL-1α/β DVD-Ig binding protein at 6 mg/kg ("IL-1α/β DVD (6 mg/kg)"). See Example 3.3.5.

As shown in FIG. 6, a combination therapy with both anti-mouse IL-1α monoclonal antibody (9H10, 6 mg/kg) and anti-mouse IL-1β monoclonal antibody (10G11, 6 mg/kg) or with IL-1α/β DVD-Ig binding protein (6 mg/kg) significantly reduced cartilage degeneration in the mouse DMM model of osteoarthritis.

Example 3.3.6

Titration of Anti-IL-1α and Anti-IL-1β Activities in Mice in a Destabilization of Medial Meniscus (DMM) Model for Osteoarthritis (8 Week Study)

An 8 week study was conducted on the effects on cartilage degeneration in response to various doses of anti-mIL-1α monoclonal antibody (9H10 mAb) and anti-mIL-1β monoclonal antibody (10G11 mAb), alone or in combination, and of mIL-1α/β 10G11-9H10 DVD-Ig binding protein in the DMM model of osteoarthritis.

Example 3.3.6.A

Study Design

Male SV129 mice weighing approximately 30 grams, housed 5/cage, were anesthetized on Day 0 with ketamine/xylazine cocktail, administered intraperitoneally (ip), and then the medial collateral ligament was exposed by blunt dissection, and transected to reflect the meniscus toward the femur. The joint space was closed with 8-0 vicryl suture. The skin was closed with wound glue. For sham surgeries, a vertical skin incision was made over the medial aspect of the knee and the joint capsule was opened. The capsule was closed with 8-0 vicryl suture, and the skin was closed with wound glue. Groups of animals were then treated with intraperitoneal (ip) injections of anti-mIL-1α monoclonal antibody, anti-mIL-1β (alone or in combination), mIL-1α/βDVD-Ig binding protein, or vehicle according to the study design table below (Table 24). Animals were euthanized after 8 weeks of treatment and knee joints were harvested in 10% neutral buffered formalin.

TABLE 24

Design of Study to Test Various Treatments in DMM Model of Osteoarthritis

| Treatment Group | Compound | Number of Animals (n) | Dose, Route and Regimen | Sacrifice Time Point |
|---|---|---|---|---|
| A | Sham (None) | 5 | None | 8 weeks |
| B | Vehicle (PBS) | 10 (9) | ip, 3x/week | 8 weeks |
| C | anti-IL-1α (9H10) | 10 (5) | 180 µg/mouse, ip, every 4th day | 8 weeks |
| D | anti-IL-1β (10G11) | 10 (8) | 180 µg/mouse, ip, every 4th day | 8 weeks |
| E | anti-IL-1α (9H10) + anti-IL-1β (10G11) | 10 (8) | 180 µg/mouse for each antibody, ip, every 4th day | 8 weeks |
| F | mIL-1αβ DVD-Ig | 10 (9) | 62.5 µg/mouse, ip, 3x/week | 8 weeks |
| G | mIL-1αβ DVD-Ig | 10 | 125 µg/mouse, ip, 3x/week | 8 weeks |
| H | mIL-1αβ DVD-Ig | 10 | 250 µg/mouse, ip, 3x/week | 8 weeks |

The numbers in parentheses in column 3 of the above table (Number of Animals) are the actual numbers of animals included in the data set. A brief description of exclusions follows:

Group B: Only 9 animals were included in Group B. One animal was excluded from the data set because at histologic examination the medial meniscus appeared intact and there was essentially no osteoarthritic change.

Group C: Only 5 animals were included in Group C. Five animals were excluded from the data set because at histologic examination the medial meniscus appeared mostly intact and there was little osteoarthritic change.

Group D: Only 8 animals were included in Group D. Slides for one animal were not present. Another animal was excluded from the data set because at histologic examination the medial meniscus appeared mostly intact and there was little osteoarthritic change.

Group E: Only 8 animals were included in Group E. Two animals were excluded because they were considered outliers.

Group F: Only 9 animals were included in Group F. One animal was excluded from the data set because at histologic examination the medial meniscus appeared intact and there was essentially no osteoarthritic change.

Example 3.3.6.B

Tissue Preparation and Examination

Tissues were prepared and scored as described above in Example 3.3.5.

Example 3.3.6.C

Results

Figure 7:
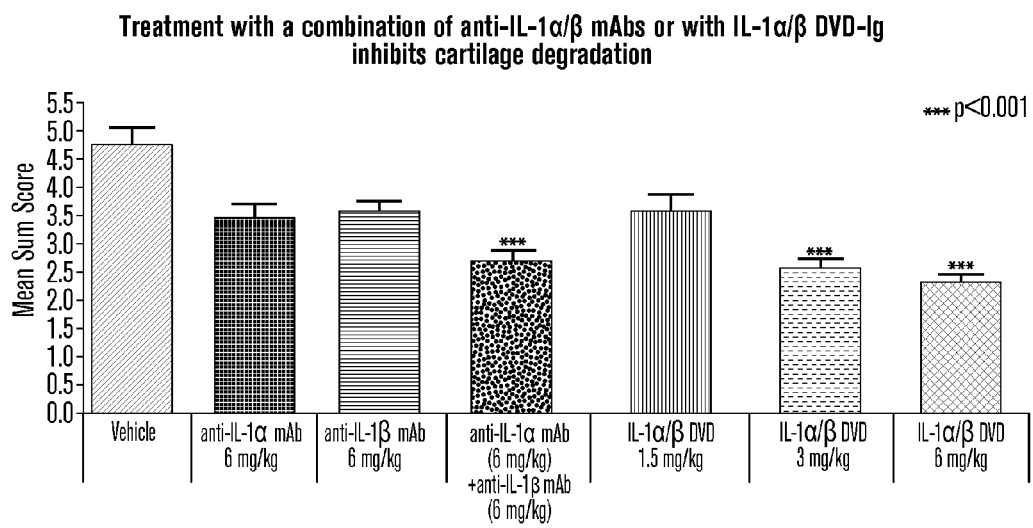
FIG. 7 shows the results of an 8 week study of various treatments on cartilage degeneration in animals in a destabilization of medial meniscus (DMM) model of osteoarthritis. Each bar graph indicates the mean sum score for cartilage degeneration in animals treated with PBS vehicle only ("Vehicle"), with anti-IL-1α monoclonal antibody (6 mg/kg) ("anti-IL-1α mAb 6 mg/kg"), with anti-IL-1β monoclonal antibody (6 mg/kg) ("anti-IL-1β 6 mg/kg"), with a combination of anti-IL-1α monoclonal antibody (6 mg/kg) and anti-IL-1β monoclonal antibody (6 mg/kg) ("anti-IL-1α mAb (6 mg/kg)+anti-IL-1β mAb (6 mg/kg)"), with mIL-1α/β DVD-Ig binding protein at 1.5 mg/kg ("IL-1α/β DVD 1.5 mg/kg"), with mIL-1α/β DVD-Ig binding protein at 3 mg/kg ("IL-1α/β DVD 3 mg/kg"), or with mIL-1α/β DVD-Ig binding protein at 6 mg/kg ("IL-1α/β DVD 6 mg/kg"). See Example 3.3.6.

The results are shown in FIG. 7. Similar to the results obtained in the joint instability model (JIM) for osteoarthritis (above), treatment with either anti-IL-1α monoclonal antibody (9H10) or anti-IL-1β monoclonal antibody (10G11) alone resulted in a decrease in cartilage degeneration that was not statistically significant from that observed in vehicle control joints. However, a combination therapy with both monoclonal antibodies or with IL-1α/β DVD-Ig binding protein (except for IL-1α/β DVD at 1.5 mg/kg) significantly reduced the mean sum Chambers scores (indicating overall cartilage degeneration) and mean maximum Chambers scores (most affected area in the joint). A statistically significant dose effect was observed for mean sum Chambers scores in the mIL-1α/β DVD-Ig treatment groups. Accordingly, in this study, 8 weeks of treatment with both anti-mIL-1α monoclonal antibody and anti-mIL-1β monoclonal antibody (6 mg/kg, each) and with mIL-1α/βDVD-Ig binding protein (at 3 and 6 mg/kg) ameliorated progression of cartilage degeneration induced in the DMM model of osteoarthritis.

Example 3.3.7

Effects of Anti-IL-1α and Anti-IL-1β Activities and Small Molecule Treatment on Cartilage Degeneration in Animals in Destabilization of Medial Meniscus (DMM) Model of Osteoarthritis Doxycycline has been shown to prevent cartilage degradation in the DMM model of osteoarthritis (Effects of Disease-modifying Osteoarthritis Drugs in an in-vivo Animal Model 1 Silva et al., Univ. Mass. Med. School, Worcester, Mass., USA, Trans ORS 2009—need full citation) and also in a human clinical trial (Brandt et al. (2005) Arthrit. Rheum. 52(7):2015-2025). In this study, the effect of treating animals in the DMM model with doxycycline was compared to the effect of treating animals with a combination of anti-IL-1α and anti-IL-1β monoclonal antibodies.

Example 3.3.7.A

Study Design

Male SV129 mice weighing approximately 30 grams had the medial collateral ligament exposed by blunt dissection, and transected to reflect the meniscus toward the femur. The joint space was closed with 8-0 vicryl suture. The skin was closed with wound glue. For sham surgeries, a vertical skin incision was made over the medial aspect of the knee and the joint capsule was opened. The capsule was closed with 8-0 vicryl suture, and the skin was closed with wound glue. Groups of animals were then treated per os (po) or via intraperitoneal (ip) injections of vehicle or treatments according to the study design table below. Three sex-matched, age-matched, and strain-matched naïve mice were also included in the study. Animals were euthanized after 4 weeks of treatment, and knee joints were harvested in 10% neutral buffered formalin.

TABLE 25

Design of Study to Test Various Anti-IL-1 Antibodies and Doxycycline Treatments in DMM Model of Osteoarthritis

| Group | Compound | Number of Animals (n) | Dose, Route and Regimen | Sacrifice Time Point |
|---|---|---|---|---|
| A | Sham (None) | 3 | None | 4 weeks |
| B | Vehicle (0.02% Tween80/ 0.5% HPMC) | 10 | po, BID | 4 weeks |

TABLE 25-continued

Design of Study to Test Various Anti-IL-1 Antibodies and Doxycycline Treatments in DMM Model of Osteoarthritis

| Group | Compound | Number of Animals (n) | Dose, Route and Regimen | Sacrifice Time Point |
|---|---|---|---|---|
| C | Doxycycline | 10 | 30 mg/kg, po, BID | 4 weeks |
| D | anti-IL-1α (9H10) + anti-IL-1β (10G11) | 10 | 180 µg/mouse each, ip, every 4th day | 4 weeks |

Example 3.3.7.B

Tissue Preparation And Examination

Tissues were prepared and scored as described above in Example 3.3.5.

Example 3.3.7.C

Results

Figure 8:
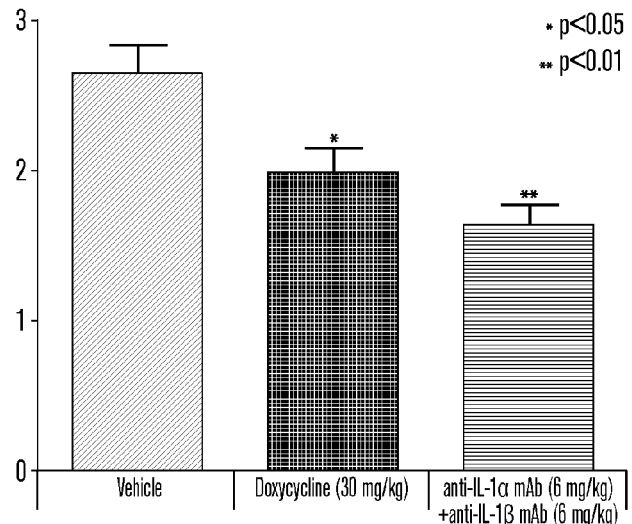
FIG. 8 shows the results of a 4 week study of treating animals in a destabilization of medial meniscus (DMM) model of osteoarthritis with vehicle alone ("Vehicle"), doxycycline (30 mg/kg) ("Doxycycline (30 mg/kg)"), or a combination of an anti-IL-1α monoclonal antibody (6 mg/kg) and an anti-IL-1β monoclonal antibody (6 mg/kg) ("anti-IL-1α mAb (6 mg/kg)+anti-IL-1β mAb (6 mg/kg)"). See Example 3.3.7.

The results are shown in FIG. 8. Under the conditions of the study, 4 weeks of treatment with a combination of anti-IL-1α and anti-IL-1β monoclonal antibodies, dosed at 180 µg/mouse each, resulted in significant amelioration of the osteoarthritic changes induced by destabilization of the medial meniscus in male SV129 mice. Mean sum Chambers scores and mean maximum Chambers scores were significantly reduced, and mean total summed Chambers scores were notably reduced by this combination treatment compared to the vehicle control group. Doxycycline treatment at 30 mg/kg also resulted in a similar treatment effect, but the antibody combination therapy was more effective.

Example 4

Pain Efficacy of Anti-IL-1α/β Therapy

The DMM model also generates measurable pain in the mice. Recently, Malfait et al. (see, Malfait et al. (2010) Osteoarthritis Cartilage, 18: 572-580) showed robust decrease in paw withdrawal threshold (mechanical allodynia indication of pain) in hind paws after DMM but not sham surgery. The efficacy of anti-IL-1α/β therapy was studied in the DMM animal model. As shown in this series of studies, mice with DMM surgery were allodynic as early as day 7 after the surgery and exhibited a decrease in paw withdrawal threshold till day 35.

Figure 9:
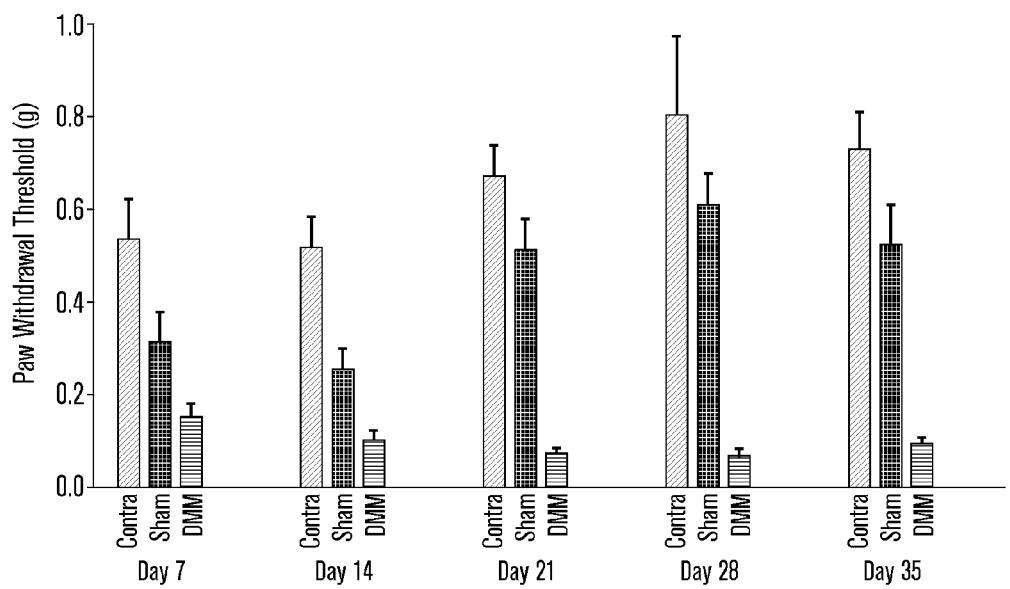
FIG. 9 shows bar graphs of paw withdrawal threshold (grams, "g") in paws of mice with DMM surgery on Days 7, 14, 21, 28, and 35. Paw withdrawal threshold of DMM paw ("DMM") was significantly decreased as compared to paws from contralateral (non-surgical) paw ("Contra") and sham surgery ("Sham"). DMM paws were allodynic as early as day 7 and exhibited this pain behavior through day 35. See Example 4.
Figure 10:
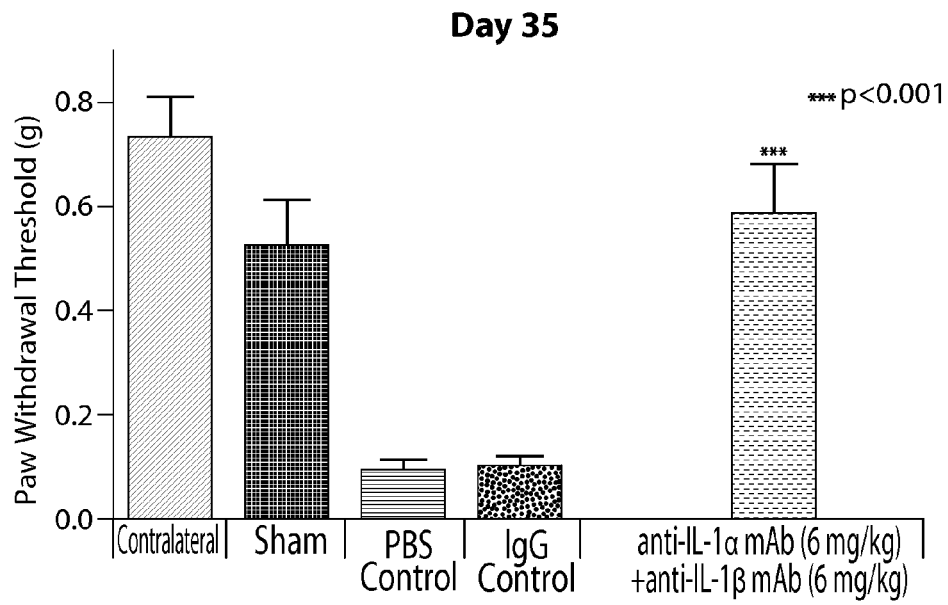
FIG. 10 shows bar graphs of paw withdrawal threshold (grams, "g") in DMM mice following treatment vehicle alone ("PBS Control"), with IgG isotype control (positive control for established disease and pain "IgG Control"), or with a combination of anti-IL-1α and anti-IL-1β monoclonal antibodies ("anti-IL-1α mAb (6 mg/kg)+anti-IL-1β mAb (6 mg/kg)") after 5 weeks (day 35) compared to paws from contralateral (non-surgical) paw ("Contralateral") and sham surgery ("Sham"). The data indicate that neutralization of both IL-1α and IL-1β significantly prevented the development of allodynia. Similar efficacy was observed in animals treated after one week (not shown). See Example 4.

The potential of anti-IL-1 therapy to ameliorate pain was tested in the DMM mouse model of OA in terms of mechanical allodynia. Dosing of the combination of IL-1α and IL-1β mAbs was initiated on the day of the surgery and was repeated twice a week for 5 weeks. Animals were treated with PBS vehicle alone, with an IgG isotype control, or with a combination of anti-IL-1α and anti-IL-1β mAbs (at a dose of 6 mg/kg for each mAb). Animals were tested weekly for paw withdrawal threshold. The ipsilateral (surgical) limb of groups treated with PBS or IgG isotype control was allodynic (painful) compared to the contra lateral (non-surgical) limb or compared to animals that had undergone sham surgery. See FIG. 9. In contrast, the group treated with the combination of anti-IL-1α and anti-IL-1β mAbs demonstrated a significantly higher paw withdrawal threshold indicating reduction in development of allodynia (pain) as compared to PBS vehicle or IgG isotype treated groups at week 5 (day 35). See FIG. 10. This reduction in pain was seen as early as week 1 following treatment (data not shown).

Figure 11:
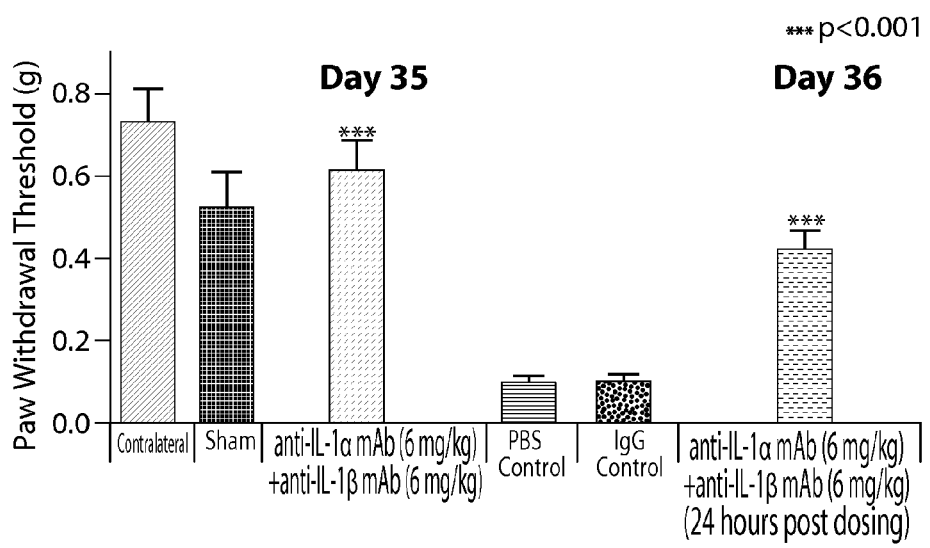
FIG. 11 shows bar graphs of paw withdrawal threshold (grams, "g") in DMM mice previously treated with IgG isotype control (positive control for established disease and pain) for 35 days and then dosed with a combination of anti-IL-1α or anti-IL-1β monoclonal antibodies and tested for paw withdrawal threshold 24 hours later at day 36 ("anti-IL-1α mAb (6 mg/kg)+anti-IL-1β (6 mg/kg) (24 hours post dosing)"). For comparison, paw withdrawal threshold values at day 35 are provided for contralateral (non-surgical) paw ("Contralateral"), sham surgery paw ("Sham"), vehicle only treatment ("PBS Control"), IgG isotype treatment ("IgG Control"), and surgical paw treated with a combination of anti-IL-1α and anti-IL-1β monoclonal antibodies ("anti-IL-1α mAb (6 mg/kg)+anti-IL-1β mAb (6 mg/kg)") after 5 weeks (day 35). The data indicate that the neutralization of both IL-1α and IL-1β significantly reversed allodynia in mice with established pain. See Example 4.

To evaluate the effect of IL-1 therapy in established pain, animals in the IgG control group with established OA and mechanical allodynia were treated on day 35 with the combination of anti-IL-1α and anti-IL-1β monoclonal antibodies and the paw withdrawal threshold was tested 24 hours later (day 36). The data demonstrated that combination therapy with anti-IL-1α and anti-IL-1β mAbs reversed allodynia (reduced OA pain) in animals with established disease. These data indicate that anti-IL-1 therapy provides an analgesic effect independent of a potential disease modifying effect. See FIG. 11.

Example 5

Further Study of Pain Efficacy of Anti-IL-1α/β Combination Therapy

Figure 12:
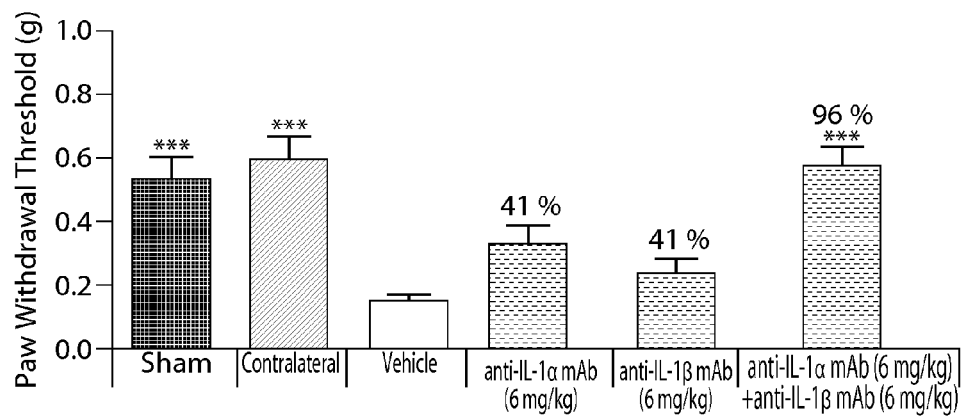
FIG. 12 shows bar graphs of paw withdrawal threshold (grams, "g") in DMM mice treated with PBS vehicle only ("Vehicle"), with anti-IL-1α monoclonal antibody (6 mg/kg)

The potential of anti-IL-1 therapy to ameliorate pain in the DMM mouse model of OA (see, above) in terms of mechanical allodynia was further evaluated. Dosing of the combination of IL-1α and IL-1β mAbs was initiated on the day of the surgery and was repeated twice a week for 4 weeks. DMM animals were treated with PBS vehicle only, with anti-IL-1α mAb (6 mg/kg), with anti-IL-1β mAb (6 mg/kg), or with a combination of anti-IL-1α mAb (6 mg/kg) and anti-IL-1β mAb (6 mg/kg), administered intraperitoneally (ip) twice per week for four weeks. Animals were tested for allodynia on day 28. The ipsilateral (surgical) limb of groups treated with vehicle was allodynic (painful) compared to the contra lateral (non-surgical) limb or compared to animals that had undergone sham surgery. See FIG. 12. Similarly, a group treated with either anti-IL-1α or anti-IL-1β mAbs alone was allodynic (painful). In contrast, a group treated with the combination of anti-IL-1α and anti-IL-1β mAbs demonstrated a significantly higher pain withdrawal threshold indicating reduction in development of allodynia (pain) as compared to vehicle treated groups (FIG. 12).

Example 6

Dose-Dependent Pain Efficacy of Anti-IL-1α/β Combination Therapy

Dosing of the combination of anti-IL-1α and anti-IL-1β mAbs was initiated on the day on which surgery was performed on animals in the DMM mouse model and was repeated twice a week for four weeks. Animals were treated with PBS vehicle only or with a combination of anti-IL-1α mAb and anti-IL-1β mAb, both administered intraperitoneally (ip) every four days for four weeks at 1 mg/kg, at 3 mg/kg, or at 6 mg/kg. Animals were tested on Day 28 for paw withdrawal threshold. The ipsilateral (surgical) limb of groups treated with vehicle showed significant reduction in the paw withdrawal threshold indicating allodynia (pain) compared to the contra lateral (non-surgical) limb or compared to animals that had undergone sham surgery (FIG. 13). In contrast, the group treated with the combination of anti-IL-1α and anti-IL-1β mAbs demonstrated a dose-dependent increase in paw withdrawal threshold indicating reduction in development of allodynia (pain) as compared to vehicle treated groups (FIG. 13).

Example 7

Anti-IL-1α/β Combination Therapy in Established Pain

To evaluate the effect of anti-IL-1α/β combination therapy in established pain, animals in the DMM mouse model with established OA and mechanical allodynia were treated at day 27 with a combination of anti-IL-1α mAb and anti-IL-1β mAb, both administered intraperitoneally (ip) at 1 mg/kg, at 3 mg/kg, or at 6 mg/kg at 24 hours prior to testing for allodynia on day 28. Results are shown in FIG. 14. The data demonstrated that combination therapy with anti-IL-1α and anti-IL-1β mAbs reversed mechanical allodynia (reduced OA pain) in animals with established disease in a dose-related manner (FIG. 14).

Example 8

Anti-Hyperalgesic Effect of Anti-IL-1α/β Combination Therapy

To evaluate whether neutralization of IL-1α and IL-1β produces antinociceptive effects in inflammatory pain conditions, anti-IL-1α and anti-IL-1β mAbs were evaluated for the ability to reverse established pain in the mouse carrageenan paw model of nociceptive pain.

The efficacy of the anti-IL-1α and anti-IL-1β mAbs was evaluated when administered alone or in combination in the mouse carrageenan model (FIG. 15). At 30 hours after intraplantar carrageenan injection: 900 μg of either anti-IL-1α mAb, anti-IL-1β mAb, or their combination were administered in different groups of mice. Thermal hyperalgesia testing was performed 48 and 96 hours after carrageenan. As seen in the previous study, the 900 μg dose combination significantly attenuated thermal hyperalgesia (carrageenan paw 8.11±0.62 s compared to 4.98±0.34 s in PBS group at 48 hours, p<0.01, FIG. 15A; carrageenan paw 7.62±0.45 s compared to 4.45±0.55 s in PBS group at 96 hours, p<0.01, FIG. 15B). The antinociceptive effect in 900 μg combination group was 53±7% at 48 hours, and 82±11% at 96 hours. The diclofenac (non-steroidal, anti-inflammatory analgesic) positive control group again exhibited a significant attenuation of thermal hyperalgesia (p<0.01 at both time points). In contrast, no significant antinociceptive effect was seen at both time points when anti-IL-1α and anti-IL-1β mAbs were administered alone indicating that simultaneous neutralization of both IL-1α and IL-1β is required for antinociceptive efficacy in the mouse carrageenan inflammatory pain model.

Example 9

Dose-Dependent Anti-Hyperalgesic Effect of Anti-IL-1α/β Combination Therapy As shown in FIG. 16, intraplantar carrageenan injection in mice (female BALB/c) produces a long lasting thermal hyperalgesia as evidenced by a decrease in paw withdrawal latency to a radiant heat stimulus (testing performed 48 and 96 hours after carrageenan injection; p<0.01 for control uninjured versus carrageenan paws in PBS vehicle group at both time points). Different groups of animals were treated either with vehicle or a combination of anti-IL-1α and anti-IL-1β mAbs (100, 300, or 900 μg/mouse of each mAb) 30 hours after carrageenan injection. A dose-related effect was seen, with the 900 μg dose combination of anti-IL-1α and anti-IL-1β mAbs significantly attenuating thermal hyperalgesia (carrageenan paw 3.23±0.34 s in PBS compared to 7.88±0.93 s in 900 μg groups at 48 hours, p<0.01, FIG. 16A; carrageenan paw 4.45±0.55 s in PBS compared to 7.62±0.45 s in 900 μg groups at 96 hours, p<0.01, FIG. 16B). The antinociceptive effect in 900 μg treatment group was 70±9% at 48 hours, and 62±4% at 96 hours. Diclofenac (30 mg/kg), a non-steroidal, anti-inflammatory analgesic, was included as positive control in the study, and it increased the mean paw withdrawal latency of the injured paw to 7.01±0.58 s at 48 hours and 7.48±0.34 s at 96 hours when administered p.o. 60 minutes before testing (p<0.01 at both time points). The IgG control and low dose 100 μg mAb groups did not attenuate thermal hyperalgesia at either time point. The mAbs and diclofenac did not significantly change the paw withdrawal latency values in the control uninjured paw.

Example 10

Efficacy of Anti-IL-1α/β Combination Therapy in CFA Pain Model

The CFA (Complete Freund's Adjuvant) inflammatory pain model was used to test whether the anti-IL-1α and anti-IL-1β mAb combination would produce efficacy against a mechanical endpoint. Therefore, mechanical allodynia was assessed using von Frey monofilaments in animals (female BALB/c mice) 48 hours after they were injected intraplantar with CFA. As seen in FIG. 17A, intraplantar CFA produced robust mechanical allodynia as evidenced by a decreased paw withdrawal threshold in the CFA injected paw treated with PBS vehicle only (0.052±0.028 g versus 0.860±0.090 g in contralateral uninjured paw, p<0.01). Separate groups of animals were treated either with IgG isotype control or a combination of anti-IL-1α and anti-IL-1β mAbs (900 μg/mouse of each mAb) 30 hours after CFA injection. The mAb treated group showed a significant attenuation of mechanical allodynia (0.419±0.101 g, p<0.01 versus PBS vehicle, FIG. 17A). The magnitude of efficacy (% MPE) was 65.51±12.35% (FIG. 17B). The anti-inflammatory, analgesic positive control diclofenac (30 mg/kg, 1 hour pretreatment) also attenuated mechanical allodynia by increasing paw withdrawal thresholds (0.359±0.088 g, p<0.01 versus PBS vehicle) with % MPE of 64.51±10.20%.

Example 11

Efficacy of Anti-IL-1α/β Combination Therapy in Neuropathic Pain

Whether an anti-IL-1α and anti-IL-1β mAb combination therapy would produce efficacy in neuropathic pain conditions was examined in an L5/L6 spinal nerve ligation (SNL) model in mice (male CD1). Testing was performed six days after SNL surgery, 24 and 72 hours after animals were treated with mAb combination (900 μg/mouse of each mAb). Mechanical allodynia was observed in mice treated with PBS vehicle only after SNL surgery as evidenced by a decreased paw withdrawal threshold to von Frey monofilament stimulation (0.073±0.032 g versus 0.735±0.109 g for contralateral paw at 24 hours, FIG. 18A; 0.128±0.048 g versus 0.732±0.132 g for contralateral paw at 72 hours, FIG. 18B; p<0.01 at both time points). The mAb treated group showed a significant attenuation of mechanical allodynia at both time points (0.477±0.131 g, p<0.01 versus PBS vehicle at 24 hours, FIG. 18A; 0.527±0.111 g, p<0.01 versus PBS vehicle at 72 hours, FIG. 18B). The magnitude of efficacy (% MPE) was 72.20±14.39% at 24 hours and 80.62±12.33% at 72 hours (FIG. 19). The positive control gabapentin (100 mg/kg, 1 hour pretreatment) was fully efficacious in attenuating mechanical allodynia by significantly increasing paw withdrawal thresholds (0.858±0.077 g at 24 hours and 1.138±0.096 g at 72 hours, p<0.01 versus PBS vehicle at both time points). In contrast, the IgG control group did not produce any effect on mechanical allodynia at both time points.

Conclusion of Pain Treatment Studies

The results of the pain studies described herein indicate that an anti-IL-1α/β combination therapy according to the invention is effective as a treatment for any form of pain and not just pain associated with osteoarthritis. Such anti-IL-1α/β combination therapy can be used to treat pain in an individual suffering from any type of pain condition including, but not limited to, the pain conditions allodynia, hyperalgesia, and a combination of allodynia and hyperalgesia. Anti-IL-1α/β combination therapy can be provided to an individual by administering to the individual a combination (for example, a mixture, concurrent administration, or successive administration) of IL-1α and IL-1β binding proteins, such as a combination of anti-IL-1α and anti-IL-1β monoclonal antibodies, or by administering to the individual a protein that binds both IL-α and IL-1β, such as a bispecific antibody or an IL-1α/β DVD-Ig binding protein that binds both IL-α and IL-1β.

INCORPORATION BY REFERENCE

The contents of all cited references (including literature references, patents, patent applications, and websites) that maybe cited throughout this application are hereby expressly incorporated by reference in their entirety, as are the references cited therein. The practice of the present invention will employ, unless otherwise indicated, conventional techniques of pharmaceutical science, immunology, molecular biology, and cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

What is claimed is:

1. A method for treating osteoarthritis in an individual suffering from the osteoarthritis, the method comprising the step of administering to the individual:
   a Dual Variable Domain Immunoglobulin (DVD-Ig) binding protein that binds both IL-1α and IL-1β,
   thereby treating the osteoarthritis in the individual.

2. The method according to claim 1, wherein said binding protein that binds both IL-1α and IL-1β is formulated in a pharmaceutical composition comprising a pharmaceutically acceptable carrier.

3. The method according to 3, wherein said binding protein that binds both IL-1α and IL-1β is crystallized.

4. The method according to claim 3, wherein said crystallized binding protein is formulated in a composition comprising an ingredient and a polymeric carrier.

5. The method according to claim 1, wherein the method further comprises administering to the individual a second agent, wherein said second agent is one or more compounds in the group consisting of budenoside, epidermal growth factor, corticosteroids, cyclosporin, sulfasalazine, amino salicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies of TNF, LT, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13, and TGFβ.

6. The method according to claim 4, wherein said polymeric carrier is a polymer selected from one or more of the group consisting of: a poly (acrylic acid), a poly (cyanoacrylate), a poly (amino acid), a poly (anhydride), a poly (depsipeptide), a poly (ester), a poly (lactic acid), a poly (lactic-co-glycolic acid) or PLGA, a poly (b-hydroxybutryate), a poly (caprolactone), a poly (dioxanone); a poly (ethylene glycol), a poly ((hydroxypropyl)methacrylamide, a poly [(organo)phosphazene], a poly (ortho ester), a poly (vinyl alcohol), a poly (vinylpyrrolidone), a maleic anhydride-alkyl vinyl ether copolymer, a pluronic polyol, an albumin, an alginate, a cellulose and a cellulose derivative, a collagen, a fibrin, a gelatin, a hyaluronic acid, an oligosaccharide, a glycaminoglycan, a sulfated polysaccharide, a blend, and a copolymer thereof.

7. The method according to claim 4, wherein said ingredient, when present, is selected from the group consisting of albumin, sucrose, trehalose, lactitol, gelatin, hydroxypropyl-β-cyclodextrin, methoxypolyethylene glycol and polyethylene glycol.

8. The method according to claim 1, wherein the osteoarthritis comprises an osteoarthritis lesion.

9. The method according to claim 1, wherein the osteoarthritis comprises an injury to an anterior cruciate ligament.

10. The method according to claim 1, wherein osteoarthritis comprises cartilage degeneration and expression of IL-6.

11. The method according to claim 10, wherein the cartilage degeneration comprises femoral cartilage degeneration or tibial cartilage degeneration.

12. The method according to claim 1, wherein administering the binding protein produces an antinociceptive effect.

13. The method according to claim 1, wherein the binding protein further treats pain.

14. The method according to claim 13, wherein the pain is selected from the group consisting of allodynia, hyperalgesia, and a combination of allodynia and hyperalgesia.

* * * * *

UNITED STATES PATENT AND TRADEMARK OFFICE
CERTIFICATE OF CORRECTION

| | | |
|---|---|---|
| PATENT NO. | : 8,889,130 B2 | Page 1 of 1 |
| APPLICATION NO. | : 13/369177 | |
| DATED | : November 18, 2014 | |
| INVENTOR(S) | : Rajesh V. Kamath | |

It is certified that error appears in the above-identified patent and that said Letters Patent is hereby corrected as shown below:

In the Claims

At column 193, line 44 delete "3. The method according to 3,"

and insert -- 3. The method according to claim 1, -- in place of the deleted language.

Signed and Sealed this
Fourteenth Day of April, 2015

Michelle K. Lee
*Director of the United States Patent and Trademark Office*